United States Patent [19]
Cochrane et al.

[11] Patent Number: 6,013,619
[45] Date of Patent: Jan. 11, 2000

[54] PULMONARY SURFACTANTS AND THERAPEUTIC USES, INCLUDING PULMONARY LAVAGE

[75] Inventors: Charles G. Cochrane, La Jolla; Susan D. Revak, San Diego, both of Calif.

[73] Assignee: The Scripps Research Institute, La Jolla, Calif.

[21] Appl. No.: 08/848,580

[22] Filed: Apr. 28, 1997

Related U.S. Application Data

[63] Continuation-in-part of application No. 08/488,123, Jun. 7, 1995, which is a continuation-in-part of application No. 08/419,824, Apr. 11, 1995, Pat. No. 5,789,381, which is a continuation of application No. 08/060,833, May 12, 1993, Pat. No. 5,407,914, which is a continuation-in-part of application No. 07/715,397, Jun. 14, 1991, Pat. No. 5,260,273, which is a continuation-in-part of application No. 07/293,201, Jan. 4, 1989, Pat. No. 5,164,369, which is a continuation-in-part of application No. 07/141,200, Jan. 6, 1988, abandoned.

[51] Int. Cl.[7] .................................................. A61M 31/00
[52] U.S. Cl. .................................. 514/2; 514/10; 514/11; 514/12; 514/13; 514/14; 604/27; 604/54
[58] Field of Search .................................. 514/10, 11, 12, 514/13, 14, 2; 604/27, 28, 35, 54

[56] References Cited

U.S. PATENT DOCUMENTS

| | | | |
|---|---|---|---|
| 4,861,756 | 8/1989 | Jackson | 514/11 |
| 4,973,582 | 11/1990 | Yoshida et al. | 514/23 |
| 5,164,369 | 11/1992 | Cochrane et al. | 514/12 |
| 5,260,273 | 11/1993 | Cochrane et al. | 514/12 |
| 5,407,914 | 4/1995 | Cochrane et al. | 514/12 |
| 5,562,608 | 10/1996 | Sekins et al. | |
| 5,789,381 | 8/1998 | Cochrane et al. | 514/13 |
| 5,803,078 | 9/1998 | Brauner | 124/207.14 |

*Primary Examiner*—Cecilia J. Tsang
*Assistant Examiner*—Patrick R. Delaney
*Attorney, Agent, or Firm*—Thomas Fitting; Emily Holmes

[57] ABSTRACT

The present invention discloses useful surfactant molecules including polypeptides, proteins, and a variety of other organic molecules, as well as methods of making and using same. Surfactant compositions, including liposomal surfactant compositions, are also disclosed. Use of the surfactant molecules of the present invention in pulmonary lavage procedures for a variety of therapeutic applications is also disclosed, including the treatment of respiratory distress syndrome; the removal of inflammatory exudate from inflamed lung tissues; and the treament of meconium aspiration syndrome in infants.

57 Claims, 16 Drawing Sheets

PULMONARY SURFACTANTS AND THERAPEUTIC USES, INCLUDING PULMONARY LAVAGE

CROSS REFERENCE TO RELATED APPLICATIONS

This is a continuation-in-part of application Ser. No. 08/488,123, filed Jun. 7, 1995, which is a continuation-in-part of application Ser. No. 08/419,824, filed Apr. 11, 1995, (now U.S. Pat. No. 5,789,381 which is a continuation of application Ser. No. 08/060,833, filed May 12, 1993 (now U.S. Pat. No. 5,407,914), which is a continuation-in-part of application Ser. No. 07/715,397, filed Jun. 14, 1991 (now U.S. Pat. No. 5,260,273), which is a continuation-in-part of application Ser. No. 07/293,201, filed Jan. 4, 1989 (now U.S. Pat. No. 5,164,369), which is a continuation-in-part of application Ser. No. 07/141,200, filed Jan. 6, 1988 (now abandoned). The disclosures of the foregoing applications are hereby incorporated by reference herein.

This invention was made with government support under Contract No. HL23584 by the National Institutes of Health. The government has certain rights in the invention.

TECHNICAL FIELD

The present invention relates to surfactant molecules, including polypeptides, proteins, and a variety of other organic molecules, which are suitable for a variety of therapeutic uses, including the treatment of respiratory distress syndrome; the removal of inflammatory exudate from inflamed lung tissues; and the treatment of meconium aspiration syndrome in infants.

BACKGROUND

1. Meconium Aspiration Syndrome

Meconium-stained amniotic fluid is present in 5–20% of all births in the U.S. Each year, approximately 26,000 newborn infants in the U.S. develop Meconium Aspiration Syndrome (MAS) (Wiswell et al, *Pediatr. Clin. North Am.*, 40:955–981, 1993; Gregory et al, *J. Pediatrics*, 85:848–852, 1974), involving progressive respiratory distress, hypoxia, hypercapnea, and acidosis requiring long-term ventilatory treatment. Severe cases require extracorporeal membrane oxygenation (ECMO) for survival (Bascik, *Pediatr. Clin. North Am.*, 24:463–479, 1977; Moront et al, *J. Thorac. Cardiovasc. Surg.*, 97:706–714, 1990; Toomasian et al, *ASAID Trans.*, 34:140–147, 1988). Mortality rates vary between 4–12%. (See, e.g., Wiswell et al, Id., 1993; Coltar et al, *Br. J. Obstet. Gynecol.*, 96:411–414, 1989; Davis et al, *Am. J. Obstet. Gynecol.*, 151:731–736, 1985; Faleiglia, *Obstet. Gynecol.*, 71:349–353, 1988).

Meconium aspiration can result in hypoxemia, vascular shunting and decreased compliance (Tyler et al, *Pediatrics* 62:454–459, 1978; Chen et al, *Crit. Care. Med.*, 13:233–236, 1985). Experimental studies have shown that after inhalation of meconium, collapse of subpleural alveoli takes place (Nieman et al, *J. Appl. Physiol.*, 58:129–136, 1985; Clark et al, *Pediatr. Res.*, 13:532, 1979) and gross and microscopic atelectasis develops (Clark et al, *J. Pediatr.*, 110:765–770, 1987; Sun et al, *J. Appl. Physiol.*, 77:1961–1971, 1994; Sun et al, *Acta Paediatr.*, 82:182–189, 1993; Sun et al, *Biol. Neonate*, 63:96–104, 1993; Seo et al, *Pediatr. Pathol.*, 10:539–548, 1990).

Atelectasis may result from mechanical obstruction (Tyler et al, *Pediatrics*, 62:454–459, 1978; Gooding et al, *Radiology*, 100:131–135, 1971; Tran et al, *Pediatr. Res.*, 14:34–38, 1980) caused by the particulate meconium, a so-called chemical pneumonitis and meconium-induced dysfunction of surfactant. While mechanical obstruction may play a role in meconium-induced pulmonary injury, the use of filtered meconium, obviating mechanical obstruction, led to loss of pulmonary function and alveolar collapse (Chen et al, *Crit. Care. Med.*, 13:233–236, 1985). This indicated a direct effect in vivo of the meconium on surfactant in the lung tissue. Surfactant extracts of atelectatic lung taken after meconium aspiration revealed poor surface tension in the Wilhelmy balance assay compared to those taken from expanded lung (Clark et al, *J. Pediatr.* 110:765–770, 1987), and in studies of adult rats and piglets, surfactant removed by lavage 60 min. after meconium aspiration showed poor surface tension properties (Sun et al, *Acta Paediatr.*, 82:182–189, 1993; Davey et al, *Ped. Res.*, 16:101–108, 1993).

A direct action of meconium on surfactant has been shown in vitro. A dose-dependent loss of surface activity of surfactant was produced by human meconium (Davey et al, Id., 1993; Moses et al, *Am J Obstet Gynecol.*, 164:477–481, 1991). Both chloroform and aqueous extracts of meconium have been found active (Sun et al, *Acta Paediatr.*, 82:182–189, 1993; Moses et al, *Am J Obstet Gynecol.*, 164:477–481, 1991), although in a separate study (Clark et al, *J. Pediatr.*, 110:765–770, 1987), only the organic extract was stated to be active.

Constituents of meconium that may contribute to alteration of the physical properties of surfactant include fatty acids, cholesterol, bile salts, bilirubin, and proteolytic enzymes (Clark et al, *J. Pediatr.*, 110:765–770, 1987; Sun et al, *Acta Paediatr.*, 82:182–189, 1993; Moses et al, *Am J Obstet Gynecol*, 164:477–481, 1991; Henderson et al, *Can. J. Surg.*, 18:64–69, 1975; Lieberman, *Gastroenterology*, 50:183–190, 1966).

Another factor in the development of pulmonary dysfunction has been stated to be a "chemical pneumonitis" (Gregory et al, *J. Pediatrics*, 85:848–852, 1974; Bascik, *Pediatr. Clin. North Am.*, 24:463–479, 1977; Tyler et al, *Pediatrics*, 62:454–459, 1978). While this dysfunction has not been clearly defined, it is presumed to follow interaction of components of meconium and the lung tissues. It is also difficult to distinguish a "chemical pneumonitis" from the inflammatory reaction that is stimulated by meconium aspiration (Tyler et al, *Pediatrics*, 62:454–459, 1978; Sun et al, *J. Appl. Physiol.*, 77:1961–1971, 1994; Davey et al, *Ped. Res.*, 16:101–108, 1993). Such an inflammatory reaction is characterized by edema, leukocyte accumulation and hemorrhage, developing 2–5 hours after exposure of the lungs to meconium and, according to a single report, increasing in severity over a 48 hour period (Tyler et al, *Pediatrics*, 62:454–459, 1978).

The components of meconium that initiate the inflammatory response, and the molecular mediating systems involved are poorly understood. Further, the effect of the inflammatory response on pulmonary function has not been determined.

With the evidence that surfactant function is impaired by meconium aspiration, some efforts have been directed toward therapeutic intervention with exogenous surfactant. Auten et al. treated 14 neonatal infants—seven with MAS and seven with Respiratory Distress Syndrome (RDS) associated with pneumonia—with calf lung surfactant extract and observed some improvement in lung function, but only minimal clearing of chest radiographs (Auten et al, *Pediatrics*, 87:101–107, 1991). A majority of the patients required additional surfactant treatment. (Also see Davis et al, *Pediatr. Pulmonol.*, 13:108–112, 1992).

Lotze et al. compared the response in 28 neonatal infants with MAS, pneumonia, hyaline membrane disease and idiopathic pulmonary hypertension of the newborn to four bolus doses of bovine surfactant, with 28 similar infants in a control group, who were treated with air alone (*J. Pediatr.*, 122:261–268, 1993). All the infant patients in that study, including those receiving boluses of bovine surfactant, required ECMO, although the surfactant treatment was found to improve pulmonary mechanics and reduce time on ECMO. When the initial study was expanded to include 167 patients in the surfactant group and 161 patients in the air-placebo group, a decreased need for ECMO in the surfactant group was observed in a statistically significant manner, but only in those patients with the least severe disease. No difference was found in time on ventilation, oxygen requirements, time to discharge, or incidence of pneumothorax, pulmonary interstitial emphysema and chronic lung disease (Lotze, *Ped. Research*, 39:#4 226A, 1996).

In a separate study, bolus administration of bovine surfactant to full-term neonates with either severe MAS (n=20) or severe RDS (n=29) produced increases in a/A ratio and a fall in Oxygen Index over a 6 hour period (Khammash et al, *Pediatrics*, 92:135–139, 1993). Most of the infants in both groups required additional doses of the surfactant, however.

Results from studies addressing the efficacy of bolus surfactant treatment in animal models of MAS have been mixed. Sun et al. observed that intratracheal instillation of a slurry of human meconium in adult rats and newborn rabbits resulted in pulmonary injury that was diminished by bolus administration of porcine lung surfactant extract (Sun et al, *J. Appl. Physiol.*, 77:1961–1971, 1994; Sun et al, *Biol. Neonate*, 63:96–104, 1993; Sun et al, *Am. J. Crit. Care Med.*, 154:764–770, 1996). Similarly, Smith claimed that bolus administration of surfactant brought about an improvement in lung function in animal models of MAS. (See Smith et al, "Exogenous surfactant in the treatment of the meconium aspiration syndrome (MAS)," presented at the 9th Annual High Frequency Ventilation of the Newborn meeting, Snowbird, Utah, Apr. 2, 1992).

However, when Wiswell et al. studied two different surfactants in a piglet model of MAS, they failed to observe differences from controls in mean airway pressures and a/A ratio over a 6 hour period (Wiswell et al, *Pediatrics Res*, 36:494–500, 1994). Histologic observations were also similar in treated and control groups. Therefore, studies to date suggest that the results are equivocal when bovine- or porcine-derived surfactant preparations are administered, particularly when administered as a bolus.

In view of the variable and limited efficacy of bolus surfactant strategies in the treatment of MAS, attention has recently been focused on approaches employing pulmonary lavage. Limited studies using piglets or rabbits as MAS models, wherein the animals' meconium-injured lungs were treated with lavage solutions. The investigators claimed that lung function improved when surfactant was administered, but not when saline lavages alone were used (Paranka et al, *Pediatr Res*, 31:625–628, 1992; and Ohama et al, *Acta Paediatr Japonica*, 33:236–238, 1994). (See also Balaraman et al, *Am. J. Respir. Crit. Care Med.*, 153:1838–1843, 1996). Similarly, two human infants with severe MAS, both destined for ECMO, were treated with repeated saline lavage, 10 ml/kg, followed by instillation of bovine surfactant. Both infants responded rapidly with an increase in a/A and clearing of chest radiographs in 4–5 hours (Ibara et al, *Acta. Paed. Japonica*, 37: 64–67, 1995).

2. Acute Respiratory Distress Syndrome (ARDS)

ARDS is an inflammatory disease of the lung, occurring in all ages of human beings, involving approximately 50,000–100,000 people in the United States per year. As the disease progresses, pulmonary function fails, requiring mechanical ventilation, and approximately 40–50% of patients die with the disease.

Many initiating factors lead to the development of ARDS, including aspiration of injurious substances such as gastric contents, inhalation of noxious fumes, including smoke or $NO_2$, pneumonia, pulmonary contusion, trauma, multiple transfusions, burns, sepsis, pancreatitis, etc. The early disease is marked by an edematous response in the lung, with accumulation of neutrophils, leading to the development of chronicity in a week with fibrin deposits and collagen production. Injury to epithelial cells is observed in the early phase together with interstitial edema.

During the development of injury, intrinsic surfactant is degraded, losing function, and atelectatic collapse of the alveoli is prominent.

Complications are prominent: failure of peripheral organs, including kidneys, liver, gastrointestinal tract and the arterial system is common. Mortality rises in proportion to the number of systems undergoing failure. There is no specific therapy for this disease.

In view of the variability in efficacy achieved by using exogenous surfactants—particularly when the surfactant is derived from non-human sources or when the surfactant is given as a bolus—and in view of the somewhat equivocal results achieved when standard lavage methods are used, alternative therapeutic modalities and formulations are clearly needed. Therefore, the compositions and methods disclosed herein provide a very real improvement over therapies and compositions described in the art.

BRIEF DESCRIPTION OF THE INVENTION

It has now been discovered that in treating the inflamed lung with pulmonary surfactant, a combination of three conditions provides superior therapy for a variety of medical diseases marked by respiratory distress as follows:

(1) dilute surfactant is administered to the lung by a lavage technique to remove injurious material and/or inflammatory exudate, to expand the lung and to improve pulmonary function;

(2) the dilute surfactant administration and monitoring of the course of pulmonary function is followed under regulated positive end-expiratory pressure; and (3) the dilute surfactant lavage fluid is removed from the lung using timed short intervals of suctioning.

The present invention discloses a wide variety of surfactant molecules which may be formulated, prepared and utilized as surfactant compositions, particularly as dilute surfactant in a lavage composition, as disclosed herein.

In particular, the present invention discloses compositions and methods useful in the treatment of respiratory distress, such as Acute Respiratory Distress Syndrome (ARDS), in general, or Meconium Aspiration Syndrome (MAS) suffered by many newborn infants, in particular. The dilute surfactant lavage can also be conducted to treat respiratory distress (e.g., RDS) in a mammal which may be associated with pulmonary inflammation, pulmonary infection, sepsis, pulmonary trauma, cranial or body trauma, pancreatitis, aspiration of gastric contents, heated vapor inhalation, noxious vapor inhalation, acute hypoxemia, fetal circulation, congenital diaphramatic hernia, pneumonia, multiple transfusions, and the like conditions.

In one embodiment, the invention contemplates a method for pulmonary lavage of a mammal comprising the steps of:

a) applying gas positive end-expiratory pressure (PEEP) with a ventilator into a lung section of the mammal at a regulated pressure, preferably from about 4 to 20 cm water;

b) instilling a lavage composition containing dilute surfactant in a pharmaceutically acceptable aqueous medium into one or more lobes or sections of the lung; and c) removing the resulting pulmonary fluid from the lung using short intervals of tracheo-bronchial suction, preferably using a negative pressure of about 20 to 100 mm mercury.

Typically, the PEEP is applied for a preselected time period prior to instilling step (b), preferably up to about 30 minutes, and in addition PEEP is typically applied continuously during steps (b) and (c) and for a preselected time period after removing step (c), preferably up to about 6 hours.

The invention can be practiced on newborn infants, infants, juveniles and adults, and is suitable for treating respiratory distress in any mammal, although it is a particularly important procedure in humans due to the extent of ARDS in human populations.

In preferred embodiments, ventilator PEEP levels are maintained at 4–15 cm water, preferably 6–9 cm water when treating newborn infants, and preferably about 6–12 cm water when treating babies, juveniles and adults. These levels have been found to facilitate lung expansion during the treatment, increasing therapeutic surfactant contact onto the alveoli and in particular to increase the rate of removal of fluids and inhibitors of surfactant function from the lung during the recovery phase. The gas applied may optionally be enriched in oxygen, i.e, from about 21 to 100% $O_2$.

A dilute surfactant is typically present in the lavage composition at 0.1–50 mg per ml, preferably about 0.5–20 mg per ml. The lavage composition is typically instilled in a volume of about 4–60 ml per kilogram, preferably about 8–30 ml per kilogram.

The short interval of suction to remove pulmonary fluids, including the instilled lavage composition, is important to minimize the drop in arterial oxygen that occurs during the suction step. A typical suctioning interval is about 2 to 120 seconds, and preferably is 5 to 20 seconds. The short suction removal step can be repeated as needed, typically 2–3 times, usually with an interval between removal steps of from about 5 seconds to 5 minutes, depending upon the condition of the patient.

In addition, the combination of instilling and removing steps can be repeated, as multiple "washes", up to 1 to 5 times, as needed.

Any of a variety of compounds, agents and molecules can be utilized as the active ingredient having surfactant activity in the lavage composition, so long as the composition is formulated as a dilute surfactant as described herein. The surfactant can comprise a substantially isolated natural pulmonary surfactant (SP) protein, or fragments thereof, a synthetic pulmonary surfactant, including peptide, organic mimetics and the like. Alternatively, the surfactant can be protein or peptide-free.

A preferred synthetic pulmonary surfactant comprises one or more phospholipids and a protein or polypeptide, in which the polypeptide, when admixed with a phospholipid, forms a synthetic pulmonary surfactant having a surfactant activity greater than the surfactant activity of the phospholipids alone. An exemplary polypeptide comprises at least 10 amino acid residues and no more than about 60 amino acid residues, including a sequence having alternating hydrophobic and hydrophilic amino acid residue regions represented by the formula $(Z_a U_b)_c Z_d$, wherein:

Z is a hydrophilic amino acid residue independently selected from the group consisting of R, D, E and K;

U is a hydrophobic amino acid residue independently selected from the group consisting of V, I, L, C and F;

a has an average value of about 1 to about 5;

b has an average value of about 3 to about 20;

c is 1 to 10; and d is 0 to 3.

Particularly preferred are surfactant compositions comprising a polypeptide having an amino acid residue sequence represented by the formula:

KLLLLKLLLLKLLLLKLLLLK;

or having an amino acid residue sequence selected from the group consisting of:

KLLLLKLLLLKLLLLKLLLLK,

KLLLLLLLLKLLLLLLLLKLL, and

KKLLLLLLLKKLLLLLLLKKL;

or having an amino acid residue sequence selected from the group consisting of:

DLLLLDLLLLDLLLLDLLLLD,

RLLLLRLLLLRLLLLRLLLLR,

RLLLLLLLLRLLLLLLLLRLL,

RRLLLLLLLRRLLLLLLLRRL,

RLLLLCLLLRLLLLCLLLR,

RLLLLCLLLRLLLLCLLLRLL, and

RLLLLCLLLRLLLLCLLLRLLLLCLLLR.

A synthetic pulmonary surfactant used in the present invention typically contains a polypeptide:phospholipid weight ratio in the range of about 1:7 to about 1:1,000. A preferred phospholipid is selected from the group consisting of:

1,2-dipalmitoyl-sn-glycero-3-phosphocholine (dipalmitoylphosphatidylcholine, DPPC);

phosphatidyl glycerol (PG); and an admixture of DPPC and PG in a weight ratio of about 3:1. In preferred embodiments, the synthetic pulmonary surfactant further contains palmitic acid.

Therefore, in various preferred embodiments of the present invention, a wide variety of surfactant polypeptides, compositions, formulations, and methods of making and using same are disclosed.

BRIEF DESCRIPTION OF THE DRAWINGS

The importance of three treatment conditions for practicing the claimed methods are illustrated in the Figures described below:

(1) Pulmonary lavage with dilute surfactant substantially increases pulmonary function (FIGS. 2, 4, 6, 8, 9, and 12A). This improvement in function follows removal of injurious material (FIG. 5) and of inflammatory exudate (FIG. 10) by the lavage procedure. The surfactant lavage also inhibits return of the inflammatory process in the lungs (FIG. 11).

(2) The important role of positive end-expiratory pressure (PEEP) in surfactant-induced expansion of the lung (FIG. 12) and in diminishing the fall in $O_2$ saturation (FIG. 13) during the lavage procedure.

(3) The importance of timed short intervals of negative-pressure suctioning on diminishing the fall in $O_2$ saturation (FIG. 14).

Figure 1:
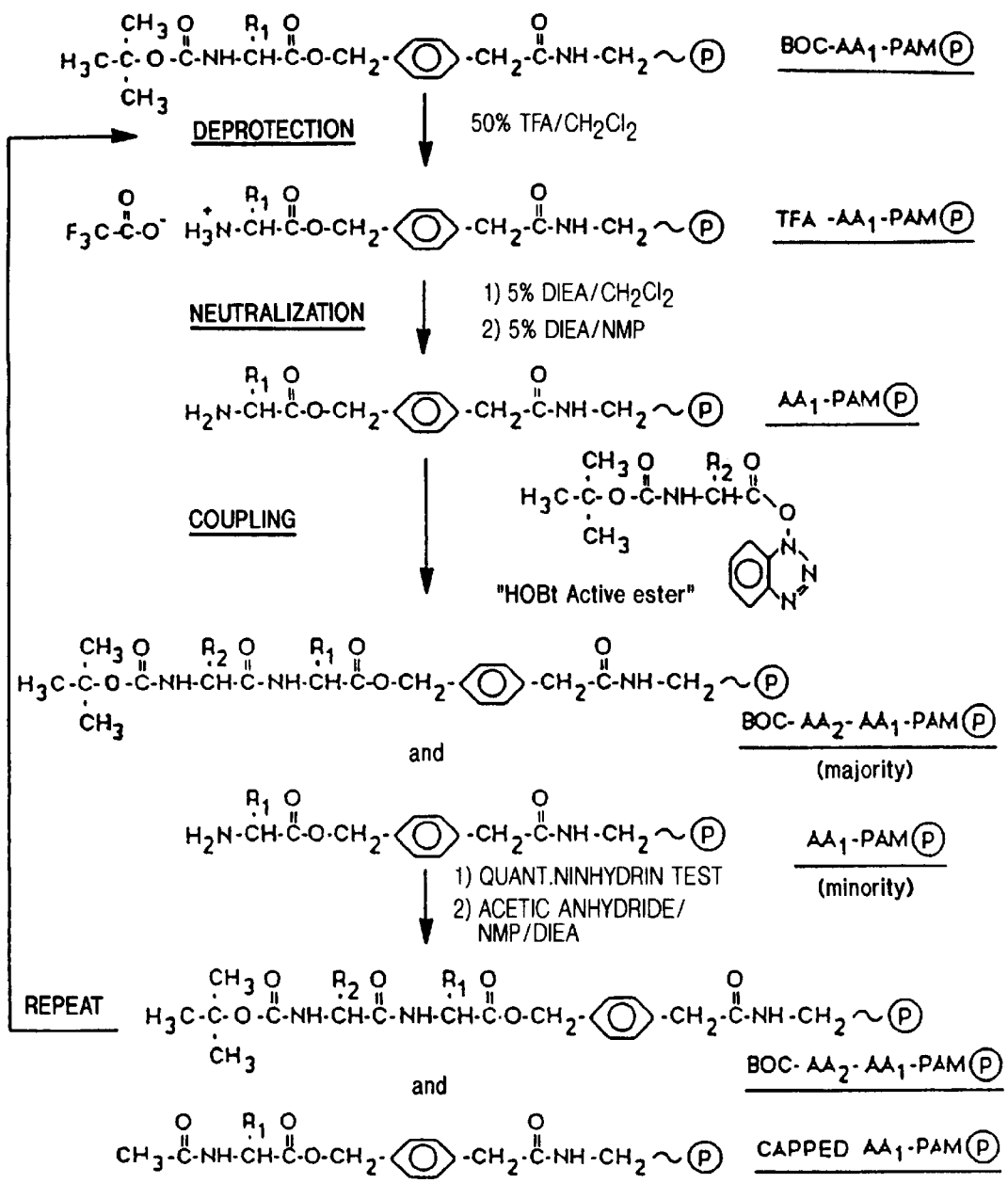

FIG. 1 illustrates the Merrifield method, which method may be used in the synthesis of a surfactant peptide of the present invention as described in Example 1.

Figure 2:
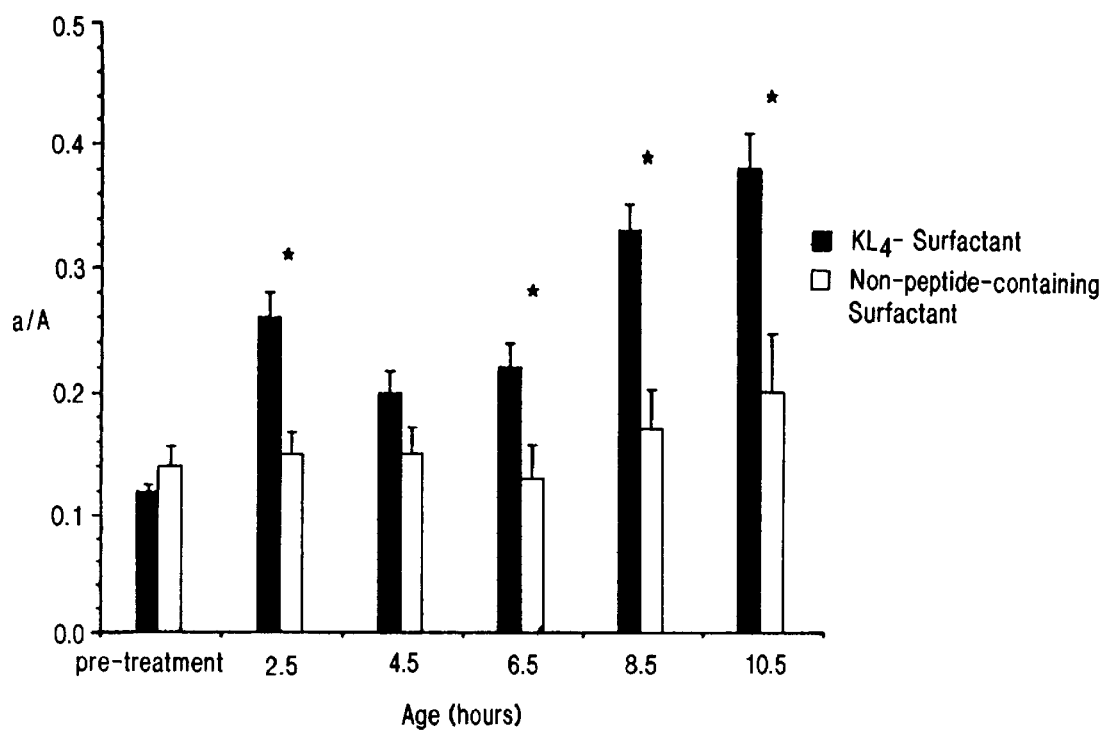

FIG. 2 compares the effect of administration of $KL_4$-containing surfactant versus non-peptide surfactant on lung function in preterm infant monkeys as described in Example 6. The ratio of arterial to alveolar oxygen tension (a/A) was measured in preterm rhesus monkeys treated to a dose of $KL_4$-surfactant (solid bars) or treated with a non-peptide surfactant (hatched bars) periodically over about 11 hours after cesarian delivery. Each bar represents the mean±SEM of all available data points within 0.5 hours of the listed time. Asterisks indicate significant statistical differences between the groups.

Figure 3:
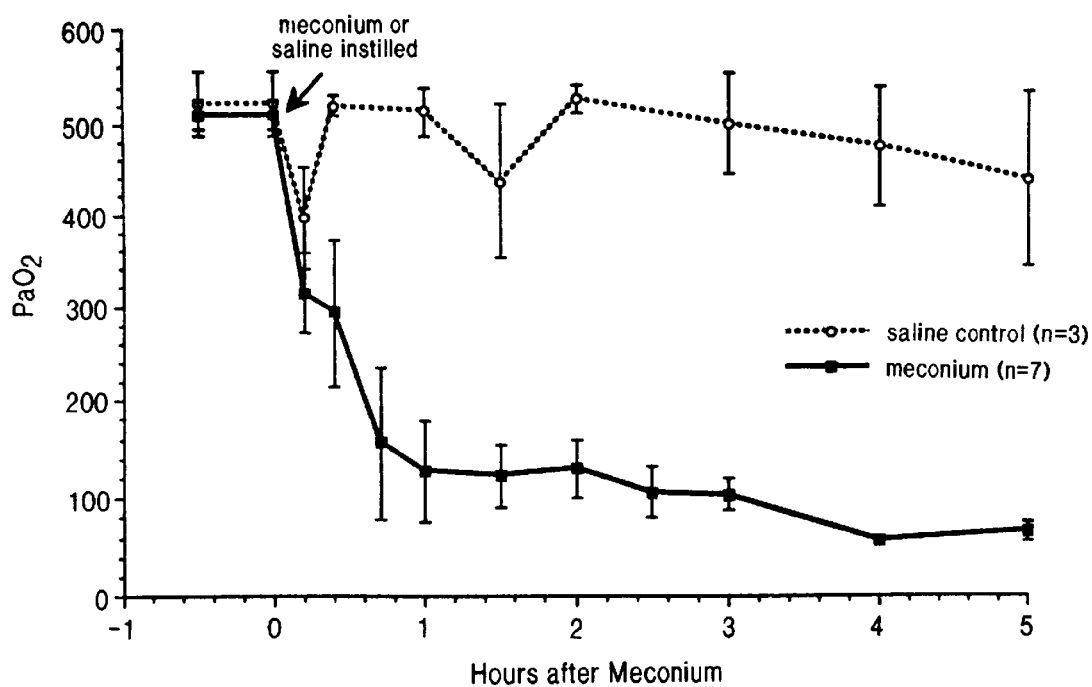

FIG. 3 illustrates the $PaO_2$ response of rabbits receiving intratracheal meconium as described in Example 5. Adult rabbits were given 7.5 ml/kg of saline (open circles, n=3) or a 25 mg/ml slurry of human meconium (closed squares, n=7) at t=0 hours. $PaO_2$ was followed for 5 hours. Data are expressed as mean±SEM. The time points of −0.5 and 0 hours are the mean values obtained pre-dosing at times varying from −0.77 to −0.03 hours; remaining time points are those nearest to the stated times. $p<0.05$ for all time points $\geq 1.0$ hours.

FIG. 4 shows compliance curves, expressed as change in change in air volume (ml/kg) as a function of pressure (cm $H_2O$) as described in Example 5. Compliance curves are shown for four representative rabbits that received 187.5 mg/kg human meconium instilled intratracheally immediately after compliance assessment at t=0 hr. FIG. 4A shows an animal that received no further treatment, while FIG. 4B shows an animal that at t=1.1 hr was lavaged 3 times using 2 mg/ml and once using 15 mg/kg $KL_4$-Surfactant (20 ml/kg each). FIG. 4C shows a meconium-injured animal that was lavaged 3 times with saline (20 ml/kg); and FIG. 4D shows an animal that received a bolus instillation of $KL_4$-Surfactant (100 mg/kg) at 1.1 hrs. For each animal, compliance data are shown for time points immediately before meconium was administered (open circles), approximately 0.9 hrs after meconium (before rescue treatment, open squares), and approximately 5.4 hrs after meconium (4 hrs after rescue treatment, solid triangles). Each animal is representative of animals in its treatment group.

Figure 5:
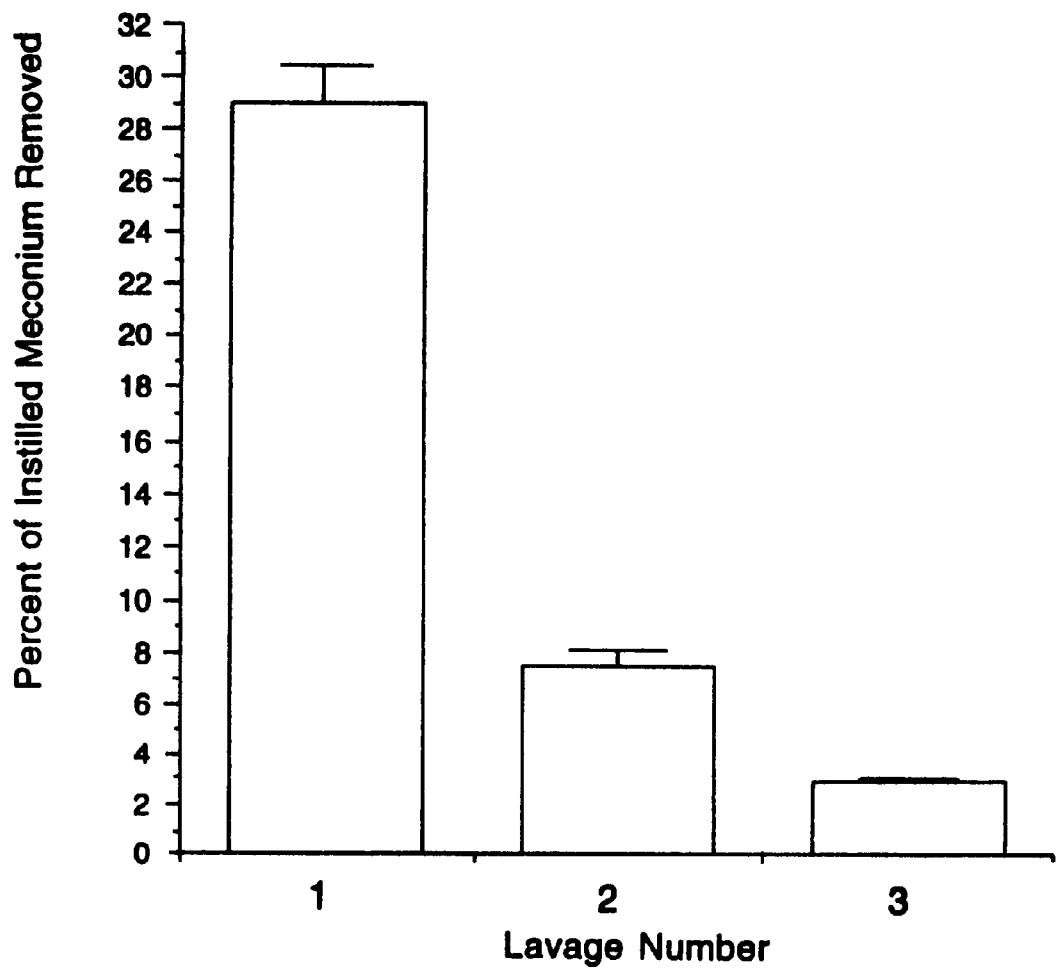

FIG. 5 illustrates the removal of meconium by lavage with $KL_4$-Surfactant as described in Example 5. Human meconium (187.5 mg/kg) was instilled into the lungs of adult rabbits. Approximately 1.1 hours later, each animal was lavaged at least 3 times with 20 ml/kg of $KL_4$-Surfactant at a concentration of 2 mg/ml. Data are shown as the mean±SEM percent of instilled meconium recovered in each lavage for six animals.

Figure 6:
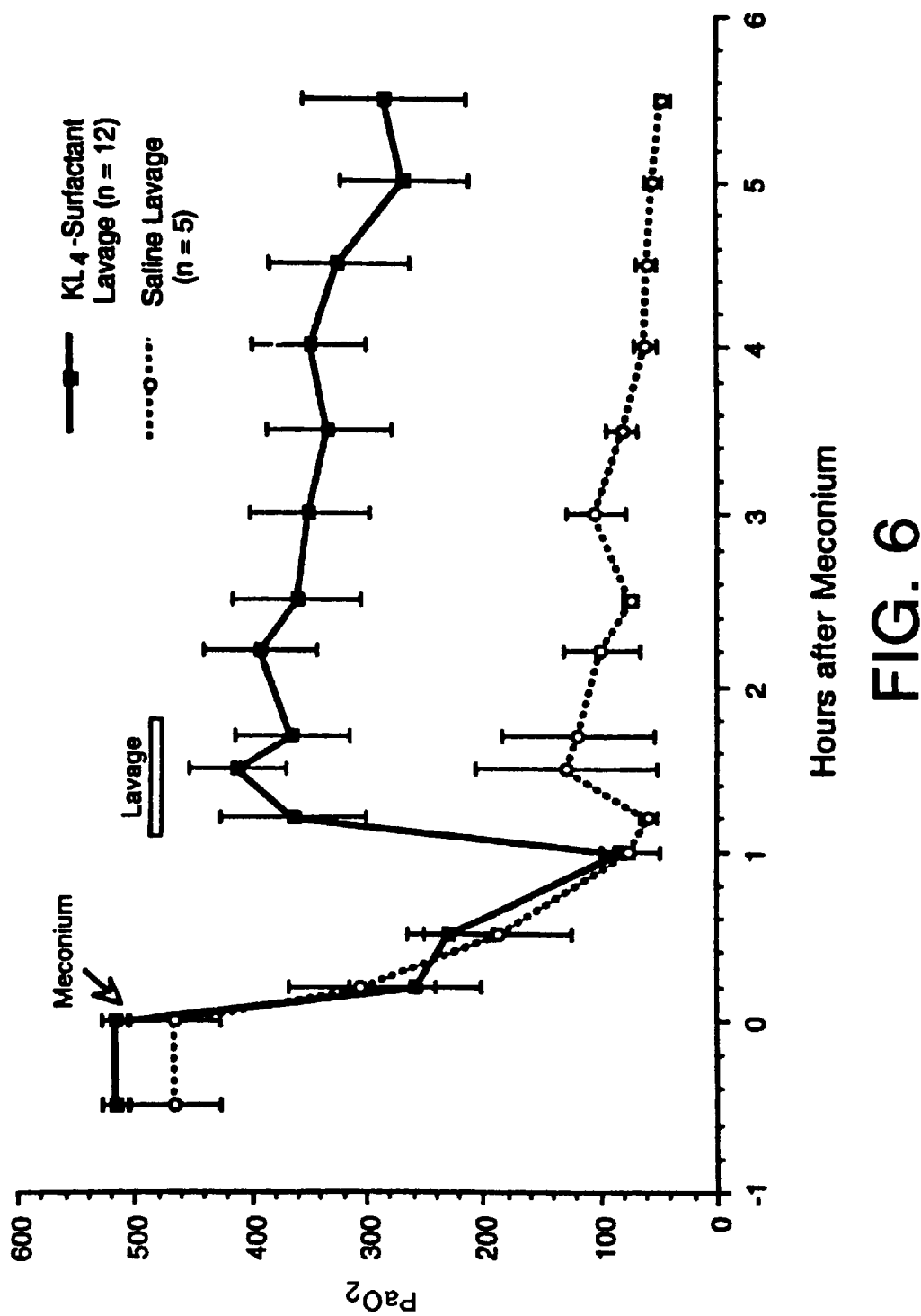

FIG. 6 illustrates changes in pulmonary function in meconium-injured rabbits following lavage with dilute $KL_4$-Surfactant as described in Example 5. Rabbits were injured with 187.5 mg/kg meconium instilled intratracheally at t=0. Approximately 1 hour later, 12 rabbits were lavaged 2–4 times with dilute $KL_4$-Surfactant (2–5 mg/ml) using 20 ml/kg followed by one lavage with a higher concentration (10–15 mg/ml) of the surfactant (solid squares). Five control animals were lavaged 3–4 times with 20 ml/kg of saline (open circles). Data are expressed as mean±SEM. The time points of −0.5 and 0 hours are the mean values obtained pre-dosing at times varying from −1.0 to −0.03 hours; remaining time points are those nearest to the stated time. $p<0.05$ for all time points>1 hour.

Figure 7:
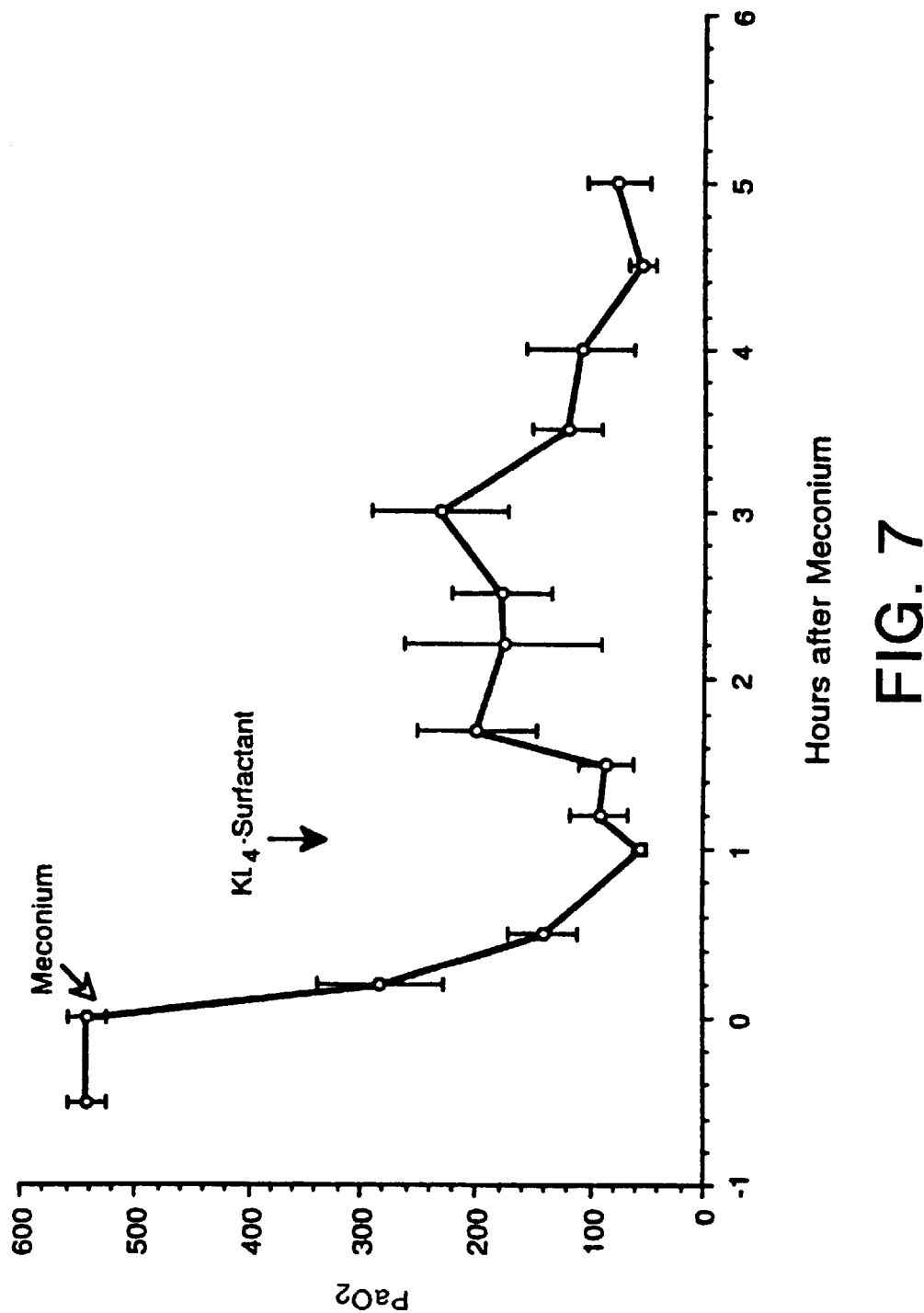

FIG. 7 illustrates changes in pulmonary function in meconium-injured rabbits following a bolus instillation of $KL_4$-Surfactant as described in Example 5. Five rabbits were injured with 187.5 mg/kg meconium instilled intratracheally at t=0. Approximately 1.1 hours later, each animal was given 100 mg/kg $KL_4$-Surfactant in a volume of 3.33 ml/kg. Data are expressed as the mean±SEM. The time points of −0.5 and 0 hours are the mean values obtained pre-dosing at times varying from −0.15 to −0.03 hours; remaining time points are those nearest to the stated time.

Figure 8:
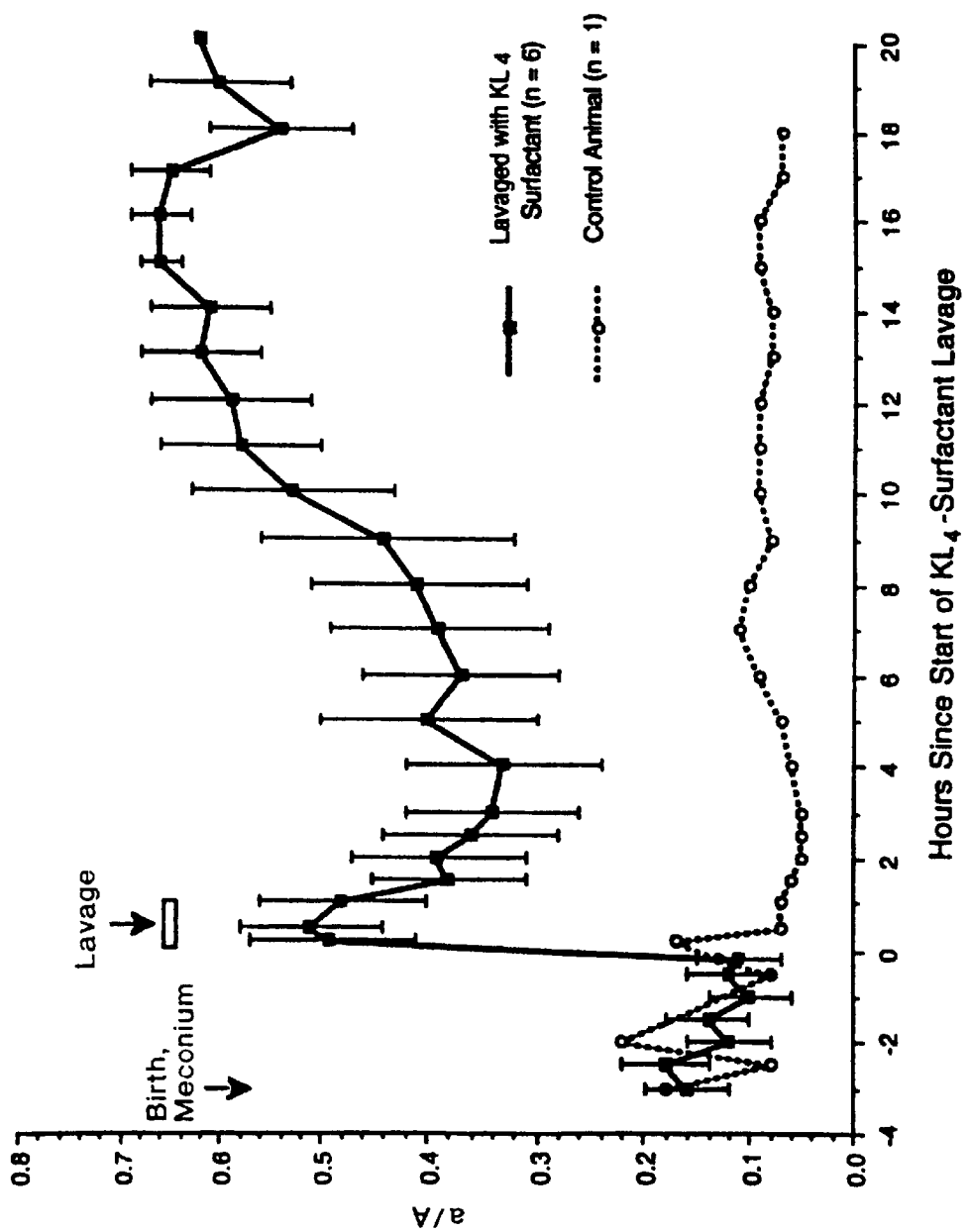

FIG. 8 illustrates the effect of treating meconium-injured newborn rhesus monkeys with $KL_4$-Surfactant lavage as described in Example 5. Seven newborn rhesus monkeys were given meconium (656 mg/kg mean quantity) into the tracheal fluid at birth. Six were treated at a mean time of 2.8 hours with 3 or 4 lavages of $KL_4$-Surfactant diluted to 2 mg/ml, followed by either lavage using $KL_4$-Surfactant at 15 mg/ml or a bolus of 100 mg at 30 mg/ml; one remained untreated and served as a control animal. Data shown are the mean±SEM values for the a/A ratio at the indicated time points. Time 0 is defined as the start of the lavage procedure.

Figure 9:
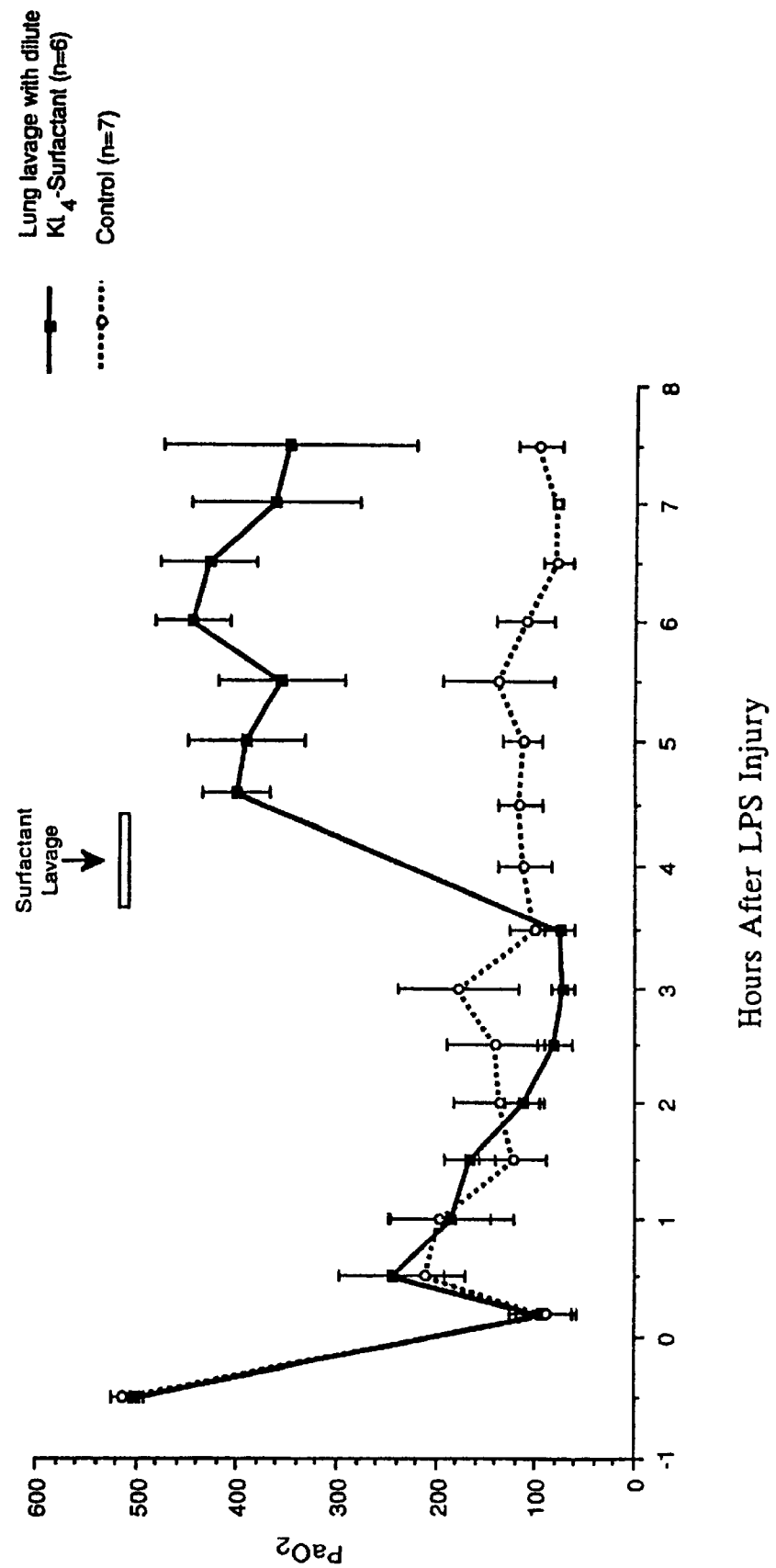
Figure 10A:
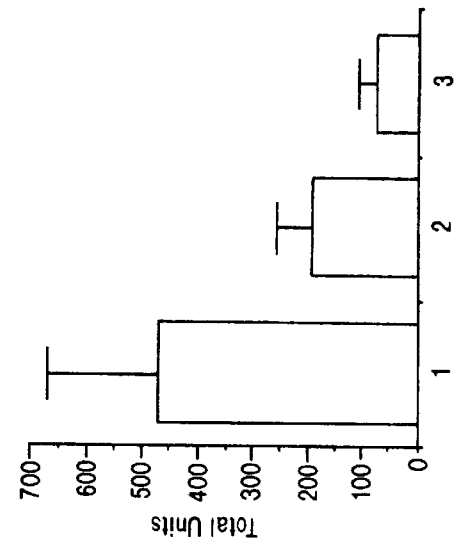
Figure 10B:
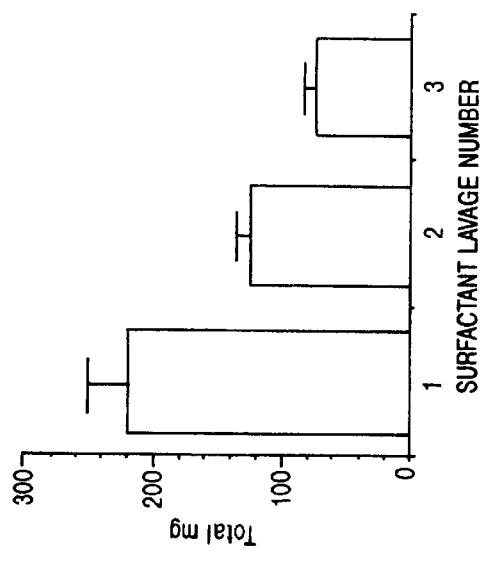
Figure 10C:
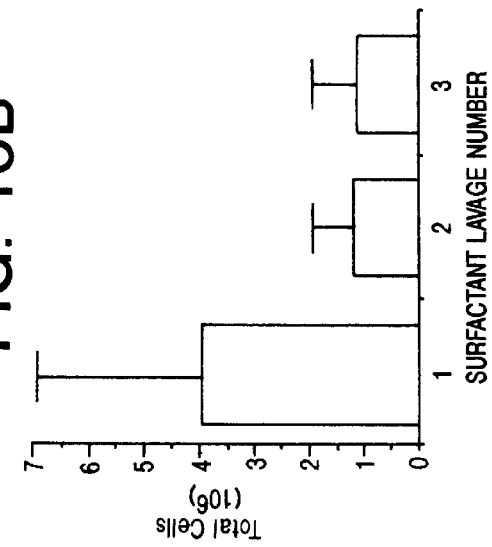
Figure 10D:
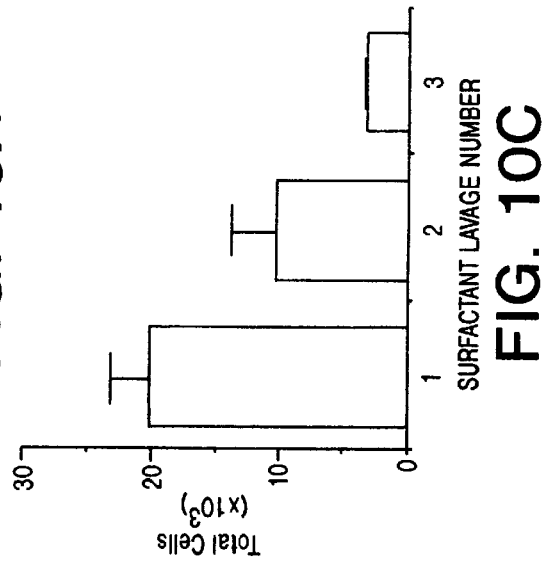
Figure 11A:
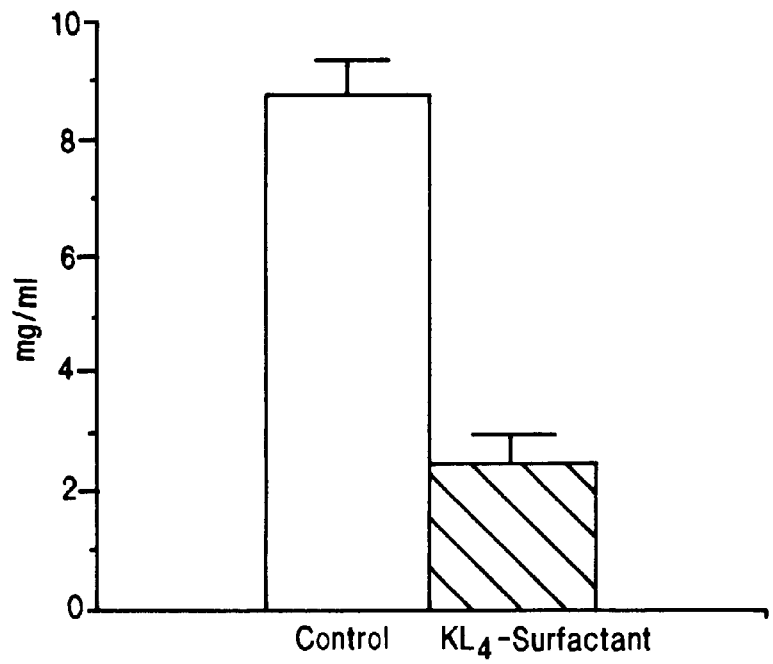
Figure 11B:
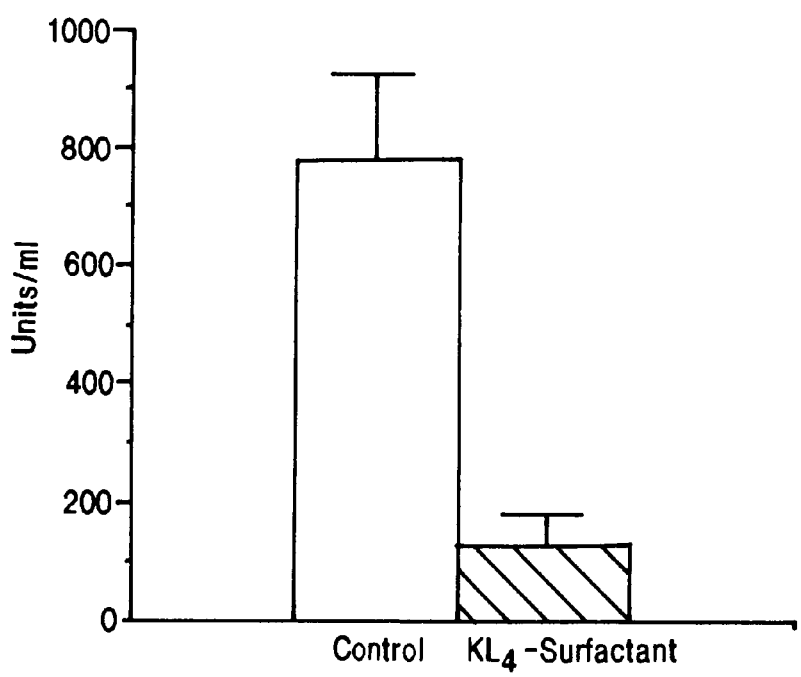
Figure 11C:
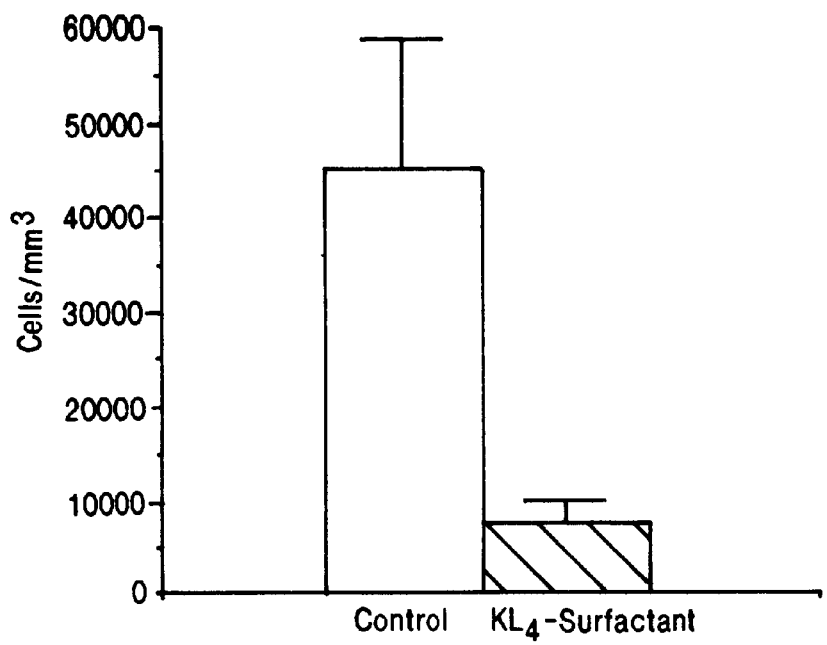
Figure 11D:
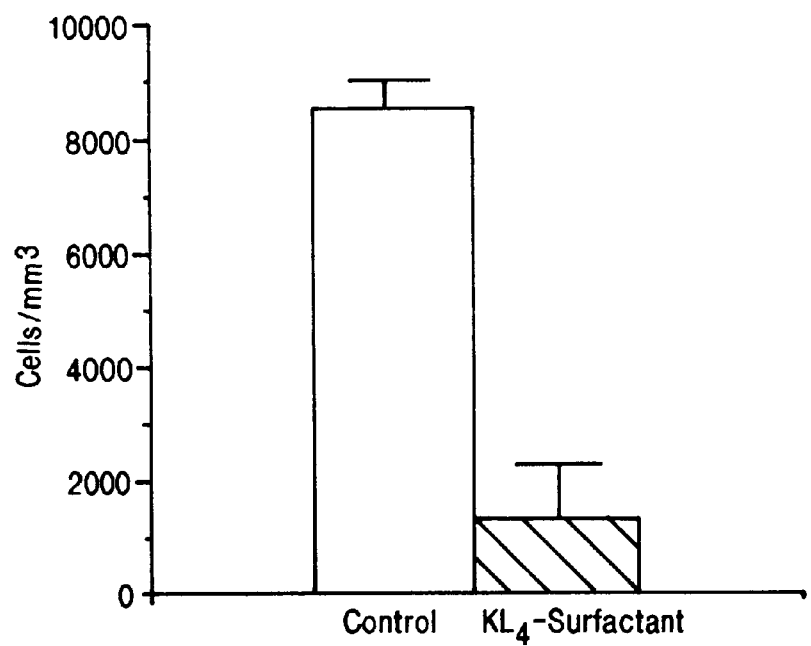

FIG. 9 illustrates the pulmonary function measured as $PaO_2$ in adult rabbits partially depleted of intrinsic surfactant by treatment with bacterial LPS-induced lung injury as a model of ARDS as described in Example 7. Following instillation of 0.75 ug/kg bacterial LPS, adult rabbits were given lavage washes containing dilute $KL_4$-surfactant containing 5 mg/ml surfactant or were untreated. $PaO_2$ was followed prior to LPS and thereafter for 8 hours. Data are expressed as mean±SEM.

FIGS. 10A through 10D illustrate a bar graph in four panels showing the amount of four components of inflammatory exudate present in sequential lavage washes following LPS injury in the adult rabbit as described in Example 7. First, second and third lavage washes are shown in each panel indicating the amount of component present in each wash.

FIGS. 11A through 11D illustrate a bar graph in four panels showing the amount of four components in inflammatory exudate present in pulmonary wash 3 hours after treatment with dilute surfactant following LPS injury in the adult rabbit as described in Example 7. Three hours after the surfactant lavage treatment described in FIG. 10, a pulmonary saline wash was collected from the lung of control and surfactant-treated rabbits. The contents of inflammatory components were analyzed in each, and are shown in each panel indicating the amount of component present in each wash.

Figure 12A:
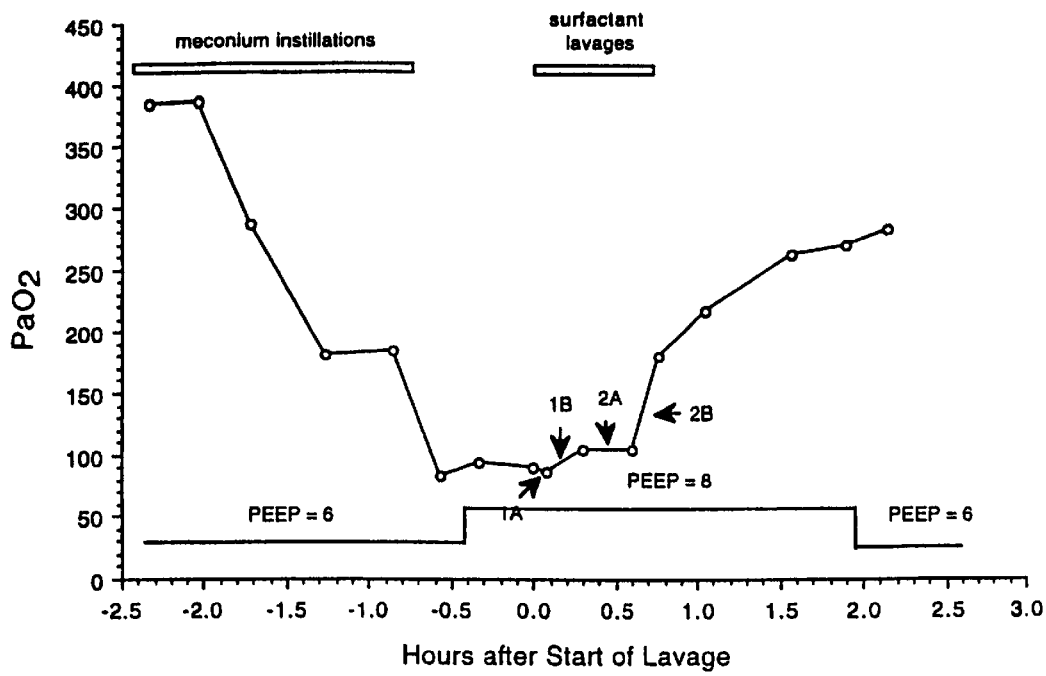
Figure 12B:
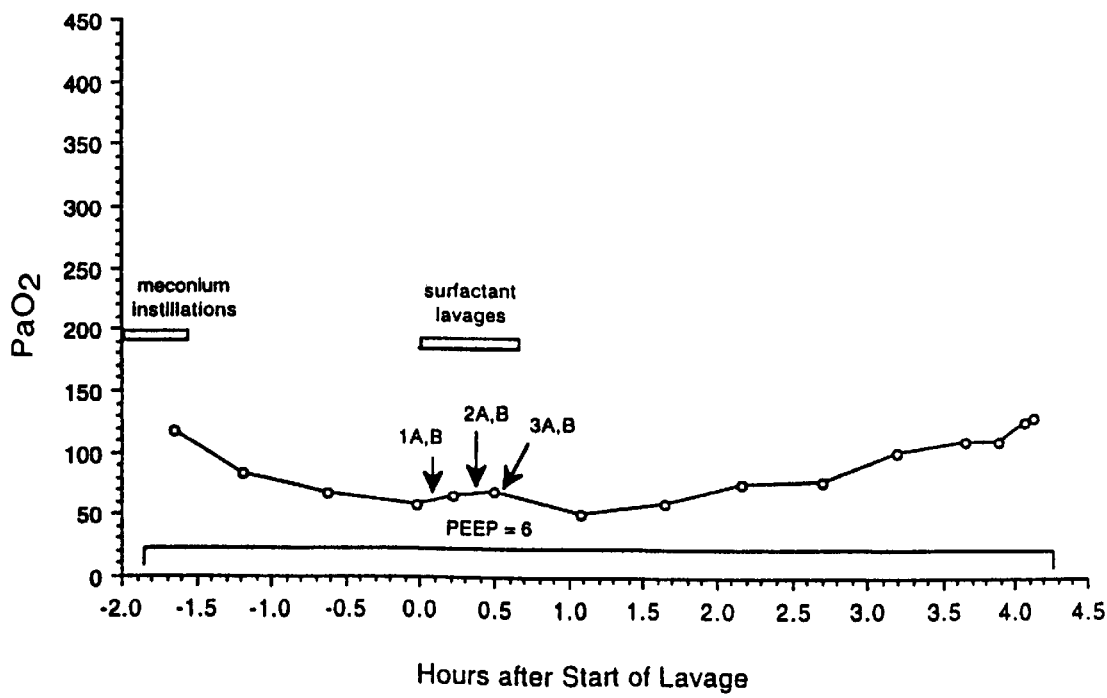

FIG. 12, in two panels FIG. 12A and FIG. 12B, illustrates the effect of elevated PEEP levels on improvement of lung function by dilute surfactant lavage in meconium-injured pigs as described in Example 8. Meconium-injured pigs were treated with surfactant lavages at the time points indicated (arrows) at PEEP of 8 cm water (FIG. 12A) or PEEP of 6 cm water (FIG. 12B). Lung function was measured by following $PaO_2$ over time during meconium installations, during surfactant lavage, and for approximately 2–4 hours after the lavage procedure.

Figure 13:
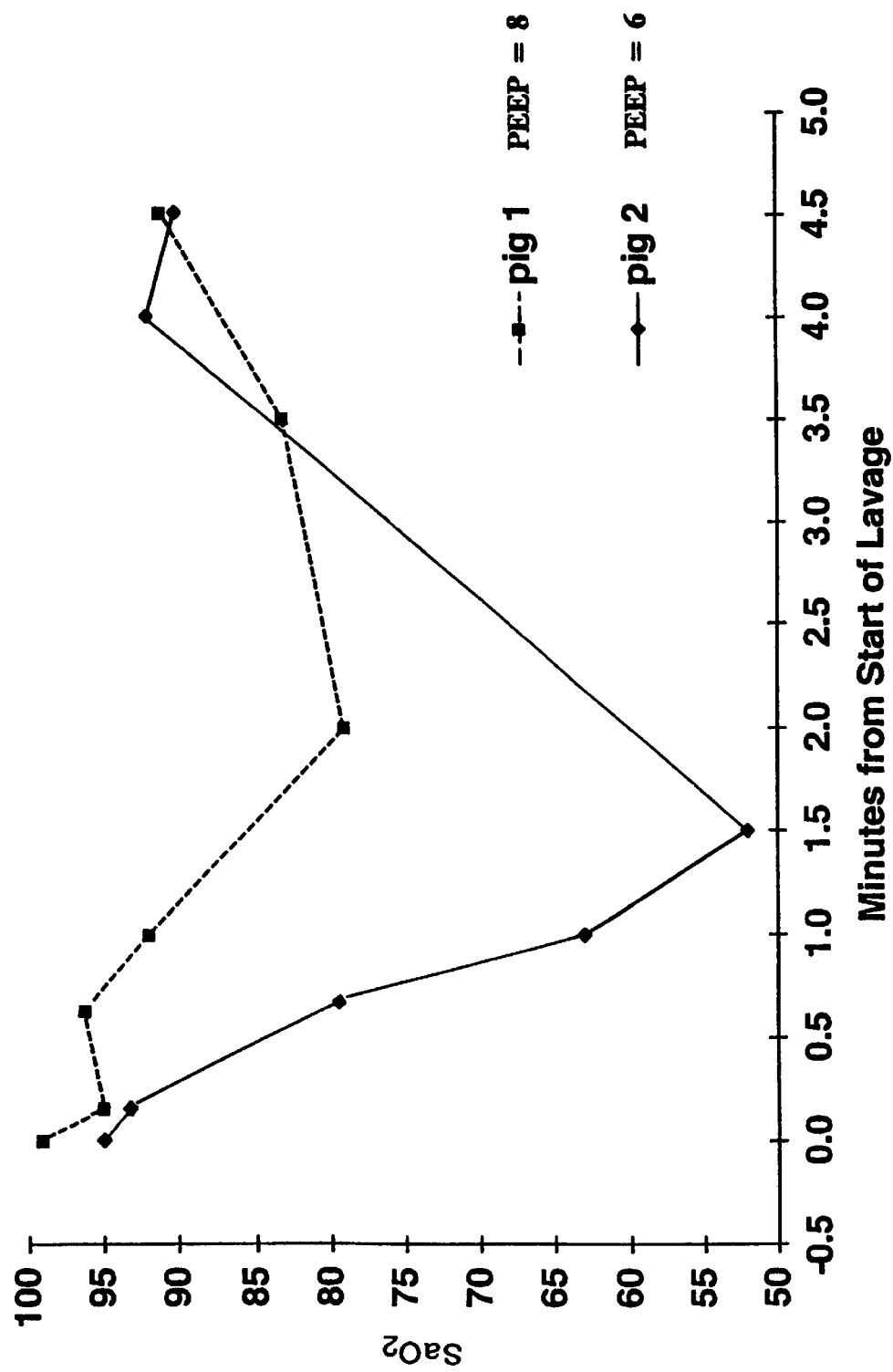

FIG. 13 illustrates the effect of PEEP on $O_2$ saturation ($SaO_2$) over time during the surfactant lavage procedure as described in Example 8. At PEEP of 8 cm water, the loss of $O_2$ saturation is considerably less than the loss that occurs when PEEP is maintained at 6 cm water.

Figure 14A:
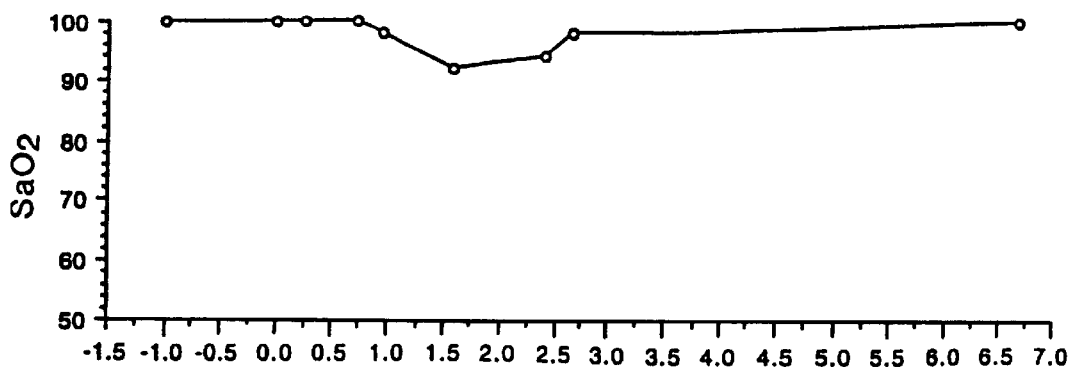
Figure 14B:
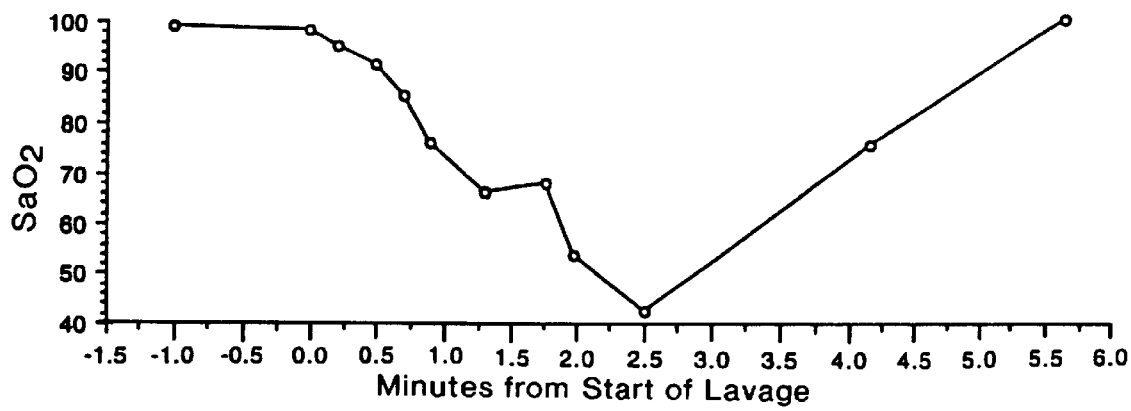

FIG. 14, in two panels FIG. 14A and FIG. 14B, illustrates the effect of the length of time of the suction interval on improvement of lung function by dilute surfactant lavage in meconium-injured pigs as described in Example 8. Meconium-injured pigs were treated as described in Example 8 with a lavage and suction using negative pressure for 10 seconds (FIG. 14A) or about 60 seconds (FIG. 14B). Lung function was measured by following $SaO_2$ (saturated $O_2$) over time during meconium installations, during surfactant lavage, and after the lavage procedure.

DETAILED DESCRIPTION OF THE INVENTION

A. Definitions

Amino Acid: In various preferred embodiments, amino acid residues identified as useful are in the natural L-configuration. As disclosed hereinbelow, however, D-amino acids, substituted amino acids (e.g., amino acids with modified R groups) amino acid metabolites and catabolites, amino acids with "retro" backbones, and amino acid mimics or analogs are also contemplated for use in—and are thus encompassed by—the present invention.

In keeping with standard polypeptide nomenclature, J. Biol. Chem., 243:3557–59, 1969, abbreviations for the more common amino acid residues are as shown in the following Table of Correspondence:

| Table of Correspondence | | |
|---|---|---|
| Symbol | | |
| 1-Letter | 3-Letter | Amino Acid |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |
| X | Xaa | Unknown/other |

It should be noted that, unless otherwise indicated, the amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1.822(b)(4), and incorporated herein by reference. The phrase "amino acid residue" is also broadly defined to include D-amino acids, substituted amino acids (e.g., amino acids with modified R groups), modified amino acids (e.g., amino acid metabolites, catabolites, and amino acids with "designed" side chains), and amino acid mimics or analogs.

Furthermore, it should be noted that a dash at the beginning or end of an amino acid residue sequence generally indicates a bond to a radical such as H and OH (hydrogen and hydroxyl) at the amino- and carboxy-termini, respectively, or a further sequence of one or more amino acid residues. In addition, it should be noted that a virgule (/) at the right-hand end of a residue sequence indicates that the sequence is continued on the next line.

Pharmaceutically acceptable is a term that refers to molecular entities and compositions that do not produce an allergic or similar untoward reaction when administered to a human.

Polypeptide and peptide are terms used interchangeably herein to designate a linear series of no more than about 60 amino acid residues connected one to the other by peptide bonds between the alpha-amino and carboxy groups of adjacent residues.

Protein is a term used herein to designate a linear series of greater than about 60 amino acid residues connected one to the other as in a polypeptide.

Surfactant activity. As used herein, the term refers to the ability of any substance, such as an organic molecule, protein or polypeptide—when combined with lipids, either alone or in combination with other organic molecules, to lower surface tension at an air/water interface. The measurement can be made with a Wilhelmy Balance or pulsating bubble surfactometer by an in vitro assay. See, for example that of King et al, Am. J. Physiol. 223:715–726 (1972), or the assay illustrated herein, which utilizes a measurement of surface tension at an air-water interface when a protein or polypeptide is admixed with a phospholipid. In addition, in vivo measurements of increases of compliance or airflow at a given pressure of air entering the lung can be readily made, such as in the assay of Robertson, Lung, 158:57–68 (1980). In this assay, the sample to be assessed is administered through an endotracheal tube to fetal rabbits or lambs delivered prematurely by Caesarian section. (These "preemies" lack their own PS, and are supported on a ventilator.) Measurements of lung compliance, blood gases and ventilator pressure provide indices of activity. In vitro assays of surfactant activity, which is assessed as the ability to lower the surface tension of a pulsating bubble, and in vivo assays utilizing fetal rabbits, as reported herein, are described in detail by Revak et al, Am. Rev. Respir. Dis., 134:1258–1265 (1986).

B. Pulmonary Surfactants—Overview

Naturally-occurring pulmonary surfactant is a complex mixture of lipids and proteins that promotes the formation of a monolayer at the alveolar air-water interface and, by reducing the surface tension, prevents collapse of the alveolus during expiration. Premature infants, and occasionally full term neonates, may lack sufficient endogenous surfactant for normal lung function. This can give rise to a condition termed respiratory distress syndrome (RDS) which may necessitate mechanical ventilation and administration of hyperbaric oxygen. Such intervention, unfortunately, can produce permanent damage to lung tissue and may cause retinopathy of prematurity (ROP) leading to blindness.

Pulmonary surfactant (PS) lines the alveolar epithelium of mature mammalian lungs. Natural PS has been described as a "lipoprotein complex" because it contains both phospholipids and apoproteins that interact to reduce surface tension at the lung air-liquid interface. Natural surfactant contains several lipid species of which dipalmitoyl phosphatidylcholine (DPPC) is the major component together with phosphatidylglycerol (PG) and palmitic acid (PA). At least three specific proteins are also associated, termed SP-A, SP-B and SP-C. Of these three, SP-B and SP-C are distinct, low molecular weight, relatively hydrophobic proteins that have been shown to enhance the surface-active properties of surfactant phospholipid mixtures. It is believed that they facilitate transfer of lipids from the bulk phase lamellar organization to the air-water interface and also stabilize the lipid monolayer during expiration. The structure of SP-B (which is alternatively referred to as SP18) is unusual in that charged amino acids (predominantly basic) are located at fairly regular intervals within stretches of otherwise hydrophobic residues. For the domain consisting of residues 59–80 of the native SP-B sequence, these charged groups have been shown to be necessary for biological activity. In addition, natural and synthetic peptides which are modeled on this hydrophobic-hydrophilic domain when combined with DPPC and PG exhibit good surfactant activity.

Surfactant is stored in lung epithelial cells in the form of lamellar bodies and, following export, it undergoes a structural transition to form tubular myelin before giving rise to a monolayer at the air-water interface. It has been proposed that surfactant proteins SP-A, -B and -C may facilitate these structural transitions and stabilize the lipid monolayer during expansion and contraction of the alveolus; however, an understanding of lipid-protein interactions at the molecular level is presently lacking. The present invention, therefore, has important implications not only with respect to the treatment of RDS in infants as well as adults, but also because of the insight it may provide into lipid-protein interactions in general.

Several exogenous surfactant formulations are currently used in the treatment of infant RDS. While these have reduced morbidity and mortality, continual improvements are needed. In particular, because of the complications that can arise due to mechanical ventilation and administration of hyperbaric oxygen, the sooner normal lung function can be established in a premature infant the more favorable will be the clinical outcome.

Consistent with the foregoing, important characteristics in an exogenous surfactant include the ability to spread rapidly to the alveoli following administration and the ability to maintain a stable monolayer at the alveolar air-water interface so that repeated treatment is not required. Thus, various compounds and compositions that are useful in the preparation of superior exogenous surfactants are disclosed herein.

C. Surfactant Compositions

A surfactant composition of the present invention can contain any of a variety of pharmaceutically acceptable compounds having surfactant activity to form a pulmonary surfactant (PS) useful in the treatment of respiratory distress syndrome. Typically a surfactant composition has admixed therein one or more phospholipids. Phospholipids useful in forming alveolar surfactants are well known in the art. See, Notter et al, *Clin. Perinatology*, 14:433–79 (1987), for a review of the use of both native and synthetic phospholipids for surfactants.

The surfactant compositions of this invention that are prepared using a protein, a polypeptide, an amino acid residue-containing molecule, or another organic molecule of the present invention having surfactant activity (collectively, "surfactant molecules"), that can include one or more phospholipids, are well suited for the treatment of Respiratory Distress Syndrome (RDS). Such surfactant compositions typically range from dilute to concentrated, depending upon the intended use as described further herein. Thus a surfactant composition can contain from as little as about 0.05 to almost 100 weight percent lipid, so long as the resulting composition has surfactant activity. By weight percent is meant the percentage of a compound by weight in a composition by weight. Thus, a composition having 50 weight percent lipid contains, for example, 50 grams lipid per 100 grams total composition. Typically, a surfactant composition contains 0.1 to 50 weight percent lipid, although higher concentrations of lipid can be used for "bolus" methods and for preparing more dilute surfactant compositions from a concentrated stock. Exemplary surfactant compositions containing both phospholipid and a surfactant molecule can contain, therefore, 0.1, 1, 10, 50, 80, to almost 100 weight percent lipid and about 50, 20, 10, to less than 1 weight percent surfactant molecule.

The surfactant composition is prepared by admixing a solution of a surfactant molecule with a suspension of liposomes, or by admixing the surfactant molecule with a suspension of liposomes, or by admixing the surfactant molecule and phospholipids directly in the presence of organic solvent.

Liposomal surfactant compositions of the present invention are generally sterile liposome suspensions containing a surfactant molecule of the present invention which has been combined with the lipids and a free fatty acid in an organic solvent system, dried, and then rehydrated. Because of the large variety of compounds and substances which have surfactant activity, it is to be understood that a surfactant composition useful in the present invention can be free from detectable protein or polypeptide, and contains only phospholipids, aqueous medium and/or buffers.

In various preferred embodiments of the present invention, pulmonary surfactants effective in treating RDS comprising an effective amount of a surfactant molecule admixed with a pharmaceutically acceptable phospholipid are disclosed. In one preferred embodiment, the surfactant molecule is a polypeptide or protein; in others, the surfactant molecule is an organic molecule displaying surfactant activity which may comprise amino acid residues, modified amino acids, amino acid derivatives, amino acid analogs, and the like molecules, or other organic molecules mimicking that activity.

While methods for determining the optimal polypeptide-:phospholipid weight ratios for a given polypeptide-phospholipid combination are well known, we have determined that therapeutically effective ratios are in the range of about 1:5 to about 1:10,000, preferably about 1:7 to about 1:5,000, more preferably about 1:10 to about 1:1000, and more preferably about 1:15 to about 1:100.

The lipid portion of a surfactant composition of the present invention is preferably about 50 to about 90, more preferably about 50 to about 75, weight percent dipalmitoylphosphatidylcholine (DPPC) with the remainder comprising unsaturated phosphatidyl choline, phosphatidyl glycerol (PG), triacylglycerols, palmitic acid, sphingomyelin or admixtures thereof.

Phospholipids useful in forming the present liposomal surfactant compositions are well known in the art. (See, e.g., Notter et al, *Clin. Perinatology*, 14:433–79, 1987, for a review of the use of both native and synthetic phospholipids for surfactants.) Methods and materials useful in the preparation of preferred surfactant compositions as disclosed herein are also described in the Examples that follow.

A pulmonary surfactant of the present invention is generally prepared by admixing a solution of a subject polypeptide with a suspension of liposomes or by admixing the subject polypeptide (or other organic surfactant molecule) and lipids directly in the presence of organic solvent. The solvent is then removed by dialysis or evaporation under nitrogen and/or exposure to vacuum.

A pulmonary surfactant composition is preferably formulated for endotracheal administration, e.g., typically as a liquid suspension, as a dry powder "dust", or as an aerosol. Those of skill in the art will appreciate that surfactant compositions of the present invention may be formulated for a variety of uses and methods of administration including, without limitation, liquid suspensions or aerosols which may be used for lavage.

For example, a surfactant (surfactant molecule-lipid micelle) may be suspended in a liquid with a pharmaceutically acceptable excipient such as water, saline, dextrose, glycerol and the like. A surfactant-containing therapeutic composition can also contain small amounts of non-toxic auxiliary substances such as pH buffering agents, including sodium acetate, sodium phosphate, and the like. To prepare a surfactant in dust form, a surfactant is prepared as described herein, then lyophilized and recovered as a dry powder.

If it is to be used in aerosol administration, a subject surfactant is supplied in finely divided form along with an additional surfactant and propellant. Typical surfactants which may be administered are phospholipids and esters. However, it is preferred, in the present case, to utilize the other components of the surfactant complex, DPPC and PG. Useful propellants are typically gases at ambient conditions, and are condensed under pressure. Lower alkane and fluorinated alkane, such as Freon, may be used. The aerosol is packaged in a container equipped with a suitable valve so that the ingredients may be maintained under pressure until released.

To prepare a liposomal surfactant composition, the surfactant molecule or polypeptide molecule is dissolved in an organic solvent that maintains the molecule in its monomeric, substantially aggregate-free form. Preferred such solvents can be polar or non-polar and exhibit solubility parameter delta ($\delta$) values in the range of about 9 to about 15 $(cal \cdot cm^3)^{1/2}$ or about 9 Hildebrand units (H) to about 15H.

Particularly preferred solvents are the hydrogen bonded solvents such as the $C_1$ to $C_4$ aliphatic alcohols, i.e., methanol ($\delta$=14.5H), ethanol ($\delta$=12.7H), n-propanol ($\delta$=11.9H), iso-propanol ($\delta$=11.5H), n-butanol ($\delta$=11.4H), iso-butanol ($\delta$=10.8H), etc. Among halogenated solvents particularly preferred are trifluoroethanol (TFE) and chloroform ($\delta$=9.3H). Mixtures or blends of aliphatic alcohols and halogenated solvents can be utilized as well.

In a preferred method for producing a liposomal surfactant composition, the polypeptide or other surfactant molecule is dissolved in the organic solvent together with the phospholipids, and the resulting solution is combined with an aqueous buffer solution. The resulting suspension is then dialyzed to remove the organic solvent. Alternatively, the organic solvent can be removed by evaporation and vacuum. The dried lipid/polypeptide mixture thus produced is rehydrated in an aqueous buffer system to produce the liposomes.

The present invention also contemplates a variety of surfactant compositions, particularly liposomal surfactants. Thus, in one preferred embodiment, the invention discloses a liposomal surfactant composition prepared from a polypeptide comprising about 10 amino acid residues and no more than about 60 amino acid residues and is constituted by alternating groupings of charged amino acid residues and uncharged amino acid residues, and a pharmaceutically acceptable phospholipid, wherein the polypeptide is present in an amount sufficient to increase the surfactant activity of the composition above that of the phospholipid.

In another preferred variation, a surfactant composition of the present invention comprises a surfactant molecule constituted by alternating groupings of charged and uncharged residues; the residues may be amino acids, modified amino acids, amino acid analogs or derivatives, and the like. Molecules having surfactant activity as disclosed herein are especially preferred for use in compositions of the present invention.

In various preferred embodiments of the present invention, as noted previously, surfactant compositions also comprise one or more phospholipids. The polypeptide:phospholipid weight ratio is in the range of about 1:7 to about 1:1,000 in various preferred surfactant compositions of the present invention. Suitable phospholipids are preferably selected from the following group: 1,2-dipalmitoyl-sn-glycero-3-phosphocholine (dipalmitoylphosphatidylcholine, DPPC); phosphatidyl glycerol (PG); and an admixture of DPPC and PG in a weight ratio of about 3:1.

The surfactant compositions (e.g., liposomal surfactants) of the present invention may further comprise palmitic acid, in various preferred embodiments. In one embodiment, the phospholipid comprises about 50–90 weight percent and the palmitic acid comprises the remaining 10–50 weight percent of the lipid portion of the surfactant. As in other preferred embodiments, the phospholipid may be selected from the group consisting of 1,2-dipalmitoyl-sn-glycero-3-phosphocholine (dipalmitoylphosphatidylcholine, DPPC); phosphatidyl glycerol (PG); and an admixture of DPPC and PG. If an admixture of DPPC and PG is selected, it is preferable that DPPC and PG be present in a weight ratio of about 3:1.

For example, in one embodiment of the present invention, a surfactant composition of the present invention comprises, in each ml of composition, 0.80 mg $KL_4$ peptide, 19.95 mg DPPC, 6.65 mg POPG, and 3.99 mg PA. In various embodiments, the surfactant is prepared aseptically and is supplied in vials containing a sufficient volume to deliver either 2 ml or 5 ml of the suspension. Thus, in one exemplary formulation, a preparation having a phospholipid concentration of about 26.6 mg/ml administered at a dosage volume of about 5.0 ml/kg would result in a dose of about 133 mg/kg. Similarly, an exemplary preparation having a phospholipid concentration of about 35 mg/ml administered at a dosage volume of about 5.7 ml/kg would result in a dose of about 200 mg/kg.

One preferred final surfactant composition comprises a sterile liposome suspension containing surfactant polypeptide (or other surfactant molecules according to the present invention). By way of illustration, a drug product/surfactant composition containing $KL_4$ peptide is described as exemplary.

Peptide is preferably combined with lipids and free fatty acid in an organic solvent system which is then removed by evaporation and vacuum. The dried lipid/peptide mixture is rehydrated in an aqueous buffer system, allowing liposomes to form. While in the organic solvents, the drug components are sterile-filtered and all subsequent processing is performed aseptically.

One exemplary composition comprises surfactant peptide and a lipid component. In one embodiment, the lipid component comprises DPPC and/or POPG. In other preferred compositions, the composition also comprises palmitic acid (PA).

For example, a surfactant composition including $KL_4$ peptide may be prepared from an admixture of DPPC and POPG in a 3:1 ratio by weight with palmitic acid (PA), 15% by weight compared with the phospholipids, in an organic solvent. $KL_4$ peptide is prepared in the surfactant dispersion as 3% by weight of the phospholipid concentration. Organic solvents were removed from the lipid/peptide mixture by evaporation under nitrogen and vacuum. A Tris buffer solution was added to form liposomes of the peptide-containing surfactant.

A Tham buffer system may also be included in a surfactant composition of the present invention. (Tham is a buffering agent also known as Tris, tromethamine, and tris (hydroxymethyl)aminomethane.) In various preferred embodiments, the compositions have a pH range of about 6.5–8.0.

Thus, in one preferred embodiment, a surfactant composition of the present invention comprises about 0.80 mg peptide, 19.95 mg DPPC, 6.65 mg POPG, 3.99 mg PA, and 1 ml Tham buffer system, per ml of the composition. In another preferred embodiment, a surfactant composition of the present invention includes the following components per ml of Tham buffer of physiologic pH and osmolality: Peptide, 1.05 mg; DPPC, 26.25 mg; POPG, 8.75 mg; and PA, 5.25 mg. Surfactant compositions are preferably prepared aseptically and are supplied as sterile, non-pyrogenic solutions in vials containing sufficient volume to deliver either 2 ml or 6 ml of the suspension.

A wide variety of surfactant molecules, proteins, and polypeptides which are preferred for use according to the disclosed methods are described above and in the sections that follow. Other preferred components of surfactant compositions used as disclosed herein include a variety of phospholipids and palmitic acid, as further described herein.

For example, currently there are a variety of known surfactants described that have been used in related methods. These surfactants are all suitable for use in the present invention according to the discovery that dilute surfactant lavages are beneficial. These surfactants include natural surfactants derived from aqueous lavages of lungs of mammals, including but not limited to bovine, porcine or ovine species, such as BLES, Infasurf or CLSE (Calf Lung Surfactant, Forest Products), Alveofact (Thomae, Germany); surfactant material extracted from animal lungs by, but not limited to, organic solvents, such as Surfactant TA (Tokyo Tanabe, Japan), Survanta (Beractant, Abbott Laboratories, Abbott Park, Ill.), Curosurf (Chiesi Farmaceutici, Parma, Italy).

In addition, surfactants can comprise various phospholipid or fatty acid molecules such palmitic acid or other factors that induce rapid spreading of the surfactant, either combined with or free of contents of supplemental peptides or proteins. Surfactants may comprise phospholipids, with or without detergents, excluding peptides or proteins, such as Exosurf (colfosceril palmitate, cetyl alcohol and tyloxapol; Burroghs-Wellcome, Research Triangle Park, N.C.), ALEC (Artificial Lung Expanding Compound, Britannia, Ltd.), phospholipid blends, such as DPPC (dipalmitoylphosphatidylcholine) plus DOPE (dioleoylphophatidylethanolamine) and cholesterol, i.e., DOPE-DPPC-cholesterol, (The Liposome Company, Princeton, N.J.).

Surfactants can comprise mixtures of phospholipids, spreading agents and proteins or peptides. The phospholipids can be phosphatidyl choline (e.g., DPPC) or phosphatidylglycerol (e.g., POPG) and the like. The spreading agents increase the rate of spreading along an air-water interface and can include palmitic acid, cholesterol, detergents and the like. The proteins and peptides can be any of those described herein or which otherwise augment surfactant activity of phospholipids, and can be isolated from natural sources, synthesized chemically or produced by recombinant DNA methodologies, such as SP-C.

Details regarding the composition and methods of preparation of these and other surfactants can be found in the following U.S. Pat. Nos. 4,603,124, 5,013,720, 5,024,995, 5,171,737, 5,185,154, 5,238,920, 5,302,581, 5,547,937, 5,552,161, and 5,614,216, the disclosures of which are hereby incorporated by reference.

A surfactant of the present invention is administered, as appropriate to the dosage form, by endotracheal tube, by bronchoscope, by cannula, by aerosol administration, or by nebulization of the suspension or dust into the inspired gas. Amounts of PS between about 1.0 and about 500 mg/kg, and preferably about 50 mg to about 500 mg/kg, and typically a dose of about 50 mg/kg, 100 mg/kg, 133 mg/kg, or 200 mg/kg, measured in terms of total phospholipid content, are administered in one dose. For use in newly born infants, one or two administrations are generally sufficient. For adults, sufficient reconstituted surfactant complex is preferably administered to produce a $PO_2$ within the normal range (see, e.g., Hallman et al, *J. Clinical Investigation*, 70:673–682, 1982). It must be appreciated that the treatment regimen may vary from individual to individual, depending on the severity of the RDS, the symptoms present, and other relevant variables; thus, single or multiple doses may be administered to an individual.

As disclosed herein, the invention contemplates the use of both concentrated and dilute surfactant compositions, depending upon the particular use, as described further herein. Concentrated surfactant compositions are typically used for "bolus" type administrations, whereas dilute surfactant compositions are typically used for "lavage" type administrations.

Typically, a concentrated surfactant has from 20 to 200 milligrams (mg) of active surfactant compound per milliliter (ml), more preferably about 25 to 100 mg/ml. A typical dilute surfactant has active surfactant compound at a concentration of from about 0.1 to 20 mg/ml, and more preferably about 0.5 to 10 mg/ml.

Polypeptides suitable for preparing surfactants in accordance with the present invention are further described in Section D immediately following.

D. Proteins and Polypeptides

A protein or polypeptide of the present invention (subject protein or polypeptide) is characterized by its amino acid residue sequence and novel functional properties. A subject protein or polypeptide when admixed with a pharmaceutically acceptable phospholipid forms a pulmonary surfactant having a surfactant activity greater than the surfactant activity of the phospholipid alone. For example, a protein or polypeptide having a surfactant activity exhibits a lower ΔP when measured in a surfactant as described in the Examples.

It is also to be understood that molecules comprising 60 or more amino acid residues—i.e. protein molecules—may be useful in surfactant compositions according to the present invention. While the present disclosure focuses primarily upon polypeptide molecules and molecules including amino acid residues, analogs, and/or other organic molecules, proteins having alternating hydrophobic and hydrophilic amino acid residue regions and proteins having surfactant ability as described herein are also contemplated by—and encompassed by—the present disclosures.

Molecules demonstrating surfactant activity which comprise 10 or fewer amino acid residues are also contemplated by the present invention. For example, a molecule comprising five amino acid residues linked to five amino acid derivatives or analogs may be useful as disclosed herein, particularly if it has alternating hydrophobic and hydrophilic amino acid residue regions and has surfactant ability, as defined herein. Thus, molecules comprising two to 100 amino acid residues having a configuration that maximizes their interaction with the alveoli are contemplated by the present invention. While larger molecules are somewhat more difficult to synthesize, it should be appreciated by those of skill in the relevant art that, as disclosed herein, even molecules containing 60 or more amino acid residues (or their analogs) may be excellent surfactants, provided they possess the disclosed characteristics.

Polypeptides suitable for preparing liposomal surfactants in accordance with the present invention can be synthesized from amino acids by techniques that are known to those skilled in the polypeptide art. An excellent summary of the many techniques available may be found in J. M. Steward and J. D. Young, "Solid Phase Peptide Synthesis", W. H. Freeman Co., San Francisco, 1969, and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group (e.g., lysine).

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and any solid support) are removed sequentially or concurrently, to afford the final polypeptide. That polypeptide is then washed by dissolving in a lower aliphatic alcohol, and dried. The dried surfactant polypeptide can be further purified by known techniques, if desired. (Various methods of preparing polypeptides of the present invention are also described in the Examples below.) Preferably, the surfactant polypeptides are polypeptides that include amino acid residue sequences having alternating charged and uncharged amino acid residue regions. Polypeptides including amino acid residue sequences having alternating hydrophobic and hydrophilic amino acid residue regions are also preferred according to the present invention. Particularly preferred surfactant polypeptides within these groupings are further characterized as having at least about 4, more preferably at least about 8, and even more preferably at least about 10, amino acid residues, and are generally not more than about 60 amino acid residues in length.

Preferably, surfactant polypeptides of the present invention are constituted by alternating groupings of charged amino acid residues and uncharged amino acid residues as represented by the formula $[(\text{Charged})_a(\text{Uncharged})_b]_c(\text{Charged})_d$, wherein a has an average value of about 1 to about 5; b has an average value of about 3 to about 20; c is 1 to 10; and d is 0 to 3. organic surfactant molecules not comprised solely of amino acid residues alone preferably have a similar structure constituted by alternating groupings of charged and uncharged (or hydrophilic/hydrophobic) constituent molecules.

In one preferred embodiment, surfactant polypeptides include a sequence having alternating groupings of amino acid residues as represented by the formula $(Z_a J_b)_c Z_d$, wherein Z is an amino acid residue independently selected from the group consisting of R, D, E, and K; J is an α-aminoaliphatic carboxylic acid; a has an average value of about 1 to about 5; b has an average value of about 3 to about 20; c is 1 to 10; and d is 0 to 3.

In another embodiment, preferred polypeptides of the present invention have alternating groupings of amino acids residue regions as represented by the formula $(B_a U_b)_c B_d$, wherein B is an amino acid residue independently selected from the group consisting of H, 5-hydroxylysine, 4-hydroxyproline, and 3-hydroxyproline; and U is an amino acid residue independently selected from the group consisting of V, I, L, C, Y, and F. In one preferred variation, B is an amino acid derived from collagen and is preferably selected from the group consisting of 5-hydroxylysine, 4-hydroxyproline, and 3-hydroxyproline; a has an average value of about 1 to about 5; b has an average value of about 3 to about 20; c is 1 to 10; and d is 0 to 3.

In still another preferred embodiment, surfactant polypeptides of the present invention include a sequence having alternating groupings of amino acid residues as represented by the formula $(B_a J_b)_c B_d$, wherein B is an amino acid residue independently selected from the group consisting of H, 5-hydroxylysine, 4-hydroxyproline, and 3-hydroxyproline; and J is an α-aminoaliphatic carboxylic acid; a has an average value of about 1 to about 5; b has an average value of about 3 to about 20; c is 1 to 10; and d is 0 to 3.

In various embodiments including "J" in the relevant formula, J is an α-aminoaliphatic carboxylic acid having four to six carbons, inclusive. In other preferred variations, J is an α-aminoaliphatic carboxylic acid having six or more carbons, inclusive. In yet other variations, J is preferably selected from the group consisting of α-aminobutanoic acid, α-aminopentanoic acid, α-amino-2-methylpropanoic acid, and α-aminohexanoic acid.

Another preferred embodiment discloses surfactant polypeptides including a sequence having alternating groupings of amino acid residues as represented by the formula $(Z_a U_b)_c Z_d$, wherein Z is an amino acid residue independently selected from the group consisting of R, D, E, and K; and U is an amino acid residue independently selected from the group consisting of V, I, L, C, Y and F; from the group consisting of V, I, L, C and F; or from the group consisting of L and C; a has an average value of about 1 to about 5; b has an average value of about 3 to about 20; c is 1 to 10; and d is 0 to 3.

In the foregoing formulae, Z and U, Z and J, B and U, and B and J are amino acid residues that, at each occurrence, are independently selected. In addition, in each of the aforementioned formulae, a generally has an average value of about 1 to about 5; b generally has an average value of about 3 to about 20; c is 1 to 10; and d is 0 to 3.

In one variation of the foregoing embodiments, Z and B are charged amino acid residues. In other preferred embodiments, Z and B are hydrophilic or positively charged amino acid residues. In one variation, Z is preferably selected from the group consisting of R, D, E and K. In a related embodiment, Z is preferably selected from the group consisting of R and K. In yet another preferred embodiment, B is selected from the group consisting of H, 5-hydroxylysine, 4-hydroxyproline, and 3-hydroxyproline. In one preferred embodiment, B is H. In another preferred embodiment, B is a collagen constituent amino acid residue and is selected from the group consisting of 5-hydroxylysine, (δ-hydroxylysine), 4-hydroxyproline, and 3-hydroxyproline.

In various disclosed embodiments, U and J are, preferably, uncharged amino acid residues. In another preferred embodiment, U and J are hydrophobic amino acid residues. In one embodiment, U is preferably selected from the group consisting of V, I, L, C, Y, and F. In another preferred embodiment, U is selected from the group consisting of V, I, L, C, and F. In yet another preferred embodiment, U is selected from the group consisting of L and C. In various preferred embodiments, U is L.

Similarly, in various embodiments, B is an amino acid preferably selected from the group consisting of H, 5-hydroxylysine, 4-hydroxyproline, and 3-hydroxyproline. Alternatively, B may be selected from the group consisting of collagen-derived amino acids, which includes 5-hydroxylysine, 4-hydroxyproline, and 3-hydroxyproline.

In another embodiment of the present invention, charged and uncharged amino acids are selected from groups of modified amino acids. For example, in one preferred embodiment, a charged amino acid is selected from the group consisting of citrulline, homoarginine, or ornithine, to name a few examples. Similarly, in various preferred embodiments, the uncharged amino acid is selected from the group consisting of α-aminobutanoic acid, α-aminopentanoic acid, α-amino-2-methylpropanoic acid, and α-aminohexanoic acid.

In preferred embodiments of the present invention, items "a", "b", "c" and "d" are numbers which indicate the number of charged or uncharged residues (or hydrophilic or hydrophobic residues). In various embodiments, "a" has an average value of about 1 to about 5, preferably about 1 to about 3, more preferably about 1 to about 2, and even more preferably, 1.

In various embodiments, "b" has an average value of about 3 to about 20, preferably about 3 to about 12, more preferably about 3 to about 10, even more preferably in the range of about 4–8. In one preferred embodiment, "b" is about 4.

In various embodiments, "c" is 1 to 10, preferably 2 to 10, more preferably in the range of 3–8 or 4–8, and even more preferably 3 to 6. In one preferred embodiment, "c" is about 4.

In various embodiments, "d" is 0 to 3 or 1 to 3. In one preferred embodiment, "d" is 0 to 2 or 1 to 2; in another preferred embodiment, "d" is 1.

By stating that an amino acid residue—e.g., a residue represented by Z or U—is independently selected, it is meant that at each occurrence, a residue from the specified group is selected. That is, when "a" is 2, for example, each of the hydrophilic residues represented by Z will be independently selected and thus can include RR, RD, RE, RK, DR, DD, DE, DK, etc. By stating that "a" and "b" have average values, it is meant that although the number of residues within the repeating sequence (e.g., $Z_aU_b$) can vary somewhat within the peptide sequence, the average values of "a" and "b" would be about 1 to about 5 and about 3 to about 20, respectively.

For example, using the formula $(Z_aU_b)_cZ_d$ for the peptide designated "KL8" in Table 1 below, the formula can be rewritten as $K_1L_8K_1L_8K_1L_2$, wherein the average value of "b" is six [i.e.,(8+8+2)/3=6], c is three and d is zero.

Exemplary preferred polypeptides of the above formula are shown in Table 1 below:

TABLE 1

| Designation[1] | SEQ ID NO | Amino Acid Residue Sequence |
|---|---|---|
| KL4 | 1 | KLLLLKLLLLKLLLLKLLLLK |
| KL8 | 2 | KLLLLLLLLKLLLLLLLLKLL |
| KL7 | 3 | KKLLLLLLLKKLLLLLLLKKL |

TABLE 1-continued

| Designation[1] | SEQ ID NO | Amino Acid Residue Sequence |
|---|---|---|
| DL4 | 4 | DLLLLDLLLLDLLLLDLLLLD |
| RL4 | 5 | RLLLLRLLLLRLLLLRLLLLR |
| RL8 | 6 | RLLLLLLLLRLLLLLLLLRLL |
| RL7 | 7 | RRLLLLLLLLRRLLLLLLLRRL |
| RCL1 | 8 | RLLLLCLLLRLLLLCLLLR |
| RCL2 | 9 | RLLLLCLLLRLLLLCLLLRLL |
| RCL3 | 10 | RLLLLCLLLRLLLLCLLLRLLLLCLLLR |
| HL4 | 13 | HLLLLHLLLLHLLLLHLLLLH |

[1]The designation is an abbreviation for the indicated amino acid residue sequence.

Also suitable are composite polypeptides of about 4 to 60 amino acid residues having a configuration that maximizes their interaction with the alveoli. A composite polypeptide consists essentially of an amino terminal sequence and a carboxy terminal sequence. The amino terminal sequence has an amino acid sequence of a hydrophobic region polypeptide or a hydrophobic peptide of this invention, preferably hydrophobic polypeptide, as defined in the above formula. The carboxy terminal sequence has the amino acid residue sequence of a subject carboxy terminal peptide.

Proteins and polypeptides derived from or having characteristics similar to those of natural Surfactant Protein (SP) are useful in the present methods. As noted, SP isolated from any mammalian species may be utilized, although bovine, porcine and human surfactants are particularly preferred.

Natural surfactant proteins include SP-A, SP-B, SP-C or SP-D, or fragments thereof, alone or in combination with lipids. A preferred fragment is the amino-terminal residues 1–25 of SP-B.

A related peptide is the WMAP-10 peptide (Marion Merrell Dow Research Institute) having the sequence succinyl-Leu-Leu-Glu-Lys-Leu-Leu-Gln-Trp-Lys-amide. Alternative peptides are polymers of lysine, arginine or histidine that induce a lowering of surface tension in admixtures of phospholipids as described herein.

In addition, human SP18 (SP-B) surfactant protein may be utilized as described herein. See, e.g., U.S. Pat. Nos. 5,407,914; 5,260,273; and 5,164,369, the disclosures of which are incorporated by reference herein.

Thus, in one embodiment, a surfactant molecule of the present invention comprises a polypeptide. In one variation, a surfactant polypeptide comprises about 4, more preferably about 10, amino acid residues. In various embodiments, a surfactant polypeptide preferably comprises 60 or fewer amino acid residues, more usually fewer than about 35, and even more preferably, fewer than about 25 amino acid residues. In various preferred embodiments, subject polypeptides correspond to the sequence of SP18 monomer—e.g., a single group of contiguous residues in the linear sequence of SP18. In other embodiments, subject polypeptides preferably have alternating charged and uncharged amino acid residue regions or have alternating hydrophobic and hydrophilic amino acid residue regions.

Polypeptides of the present invention may also be subject to various changes, such as insertions, deletions and substitutions, either conservative or non-conservative, where such changes provide for certain advantages in their use. Conservative substitutions are those in which one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

Additional residues may be added at either terminus of a polypeptide of the present invention, such as for the purpose of providing a "linker" by which such a polypeptide can be conveniently affixed to a label or solid matrix, or carrier. Labels, solid matrices and carriers that can be used with the polypeptides of this invention are known in the art; some examples are also described herein.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-NH$_2$ acylation, e.g., acetylation, or thioglycolic acid amidation, terminal-carboxlyamidation, e.g., ammonia, methylamine, etc.

In another embodiment, a polypeptide of this invention has amino acid residue sequence that has a composite hydrophobicity of less than zero, preferably less than or equal to $-1$, more preferably less than or equal to $-2$. Determination of the composite hydrophobicity value for a peptide is described in detail in Example 3. These hydrophobic polypeptides perform the function of the hydrophobic region of SP8. Thus, in one preferred embodiment, the amino acid sequence mimics the pattern of charged and uncharged—or hydrophobic and hydrophilic—residues of SP18.

It should be understood, however, that polypeptides and other surfactant molecules of the present invention are not limited to molecules having sequences like that of native SP18. On the contrary, some of the most preferred surfactant molecules of the present invention have little resemblance to SP18 with respect to a specific amino acid residue sequence, except that they have similar surfactant activity and alternating charged/uncharged (or hydrophobic/hydrophilic) residue sequences.

One disclosed embodiment of the present invention comprises a peptide-containing preparation, the 21-residue peptide being a mimic of human SP-B consisting of repeated units of four hydrophobic leucine (L) residues, bounded by basic polar lysine (K) residues. This exemplary peptide, which is abbreviated herein as "KL$_4$," has the following amino acid residue sequence:

KLLLLKLLLLKLLLLKLLLLK (SEQ ID NO 1).

Combined with the phospholipids dipalmitoyl phosphatidylcholine and palmitoyl-, oleoylphosphatidyl glycerol (3:1) and palmitic acid, the phospholipid-peptide aqueous dispersion has been named "KL$_4$-Surfactant," and it is generally referred to herein in that manner. The efficacy of KL$_4$-Surfactant in various experimental and clinical studies has been previously reported. See, e.g., Cochrane et al, *Science*, 254:566–568 (1991); Vincent et al., *Biochemistry*, 30:8395–8401 (1991); Cochrane et al., *Am J Resp & Crit Care Med*, 152:404–410 (1996); and Revak et al., *Ped. Res.*, 39:715–724 (1996).

E. Amino Acids, Natural Metabolites, Derivatives, Designed Analogs, and Other Organic Molecules Surfactant molecules of the present invention also include organic molecules having surfactant activity, as defined above and as further described herein. While polypeptides and proteins are often described as exemplary, it should be understood that surfactant molecules of the present invention are not limited to those having either conventional amino acid side chains or a polyamide backbone structure.

As noted previously, the present invention contemplates a variety of surfactant molecules, including proteins, polypeptides, and molecules including amino acid residues, as well as a variety of surfactant compositions. While one tends to think of the "common" natural amino acids (i.e., those listed in the "Table of Correspondence" in Section A above) as being preferred for use in biological compositions, it is also true that a wide variety of other molecules, including uncommon but naturally occurring amino acids, metabolites and catabolites of natural amino acids, substituted amino acids, and amino acid analogs, as well as amino acids in the "D" configuration, are useful in molecules and compositions of the present invention. In addition, "designed" amino acid derivatives, analogs and mimics are also useful in various compounds, compositions and methods of the present invention, as well as polymers including backbone structures composed of non-amide linkages.

For example, in addition to the L-amino acids listed in the "Table of Correspondence" in Section A above, amino acid metabolites such as homoarginine, citrulline, ornithine, and α-aminobutanoic acid are also useful in molecules and compositions of the present invention. Thus, in the various formulas described above, "Charged", Z, or B may comprise homoarginine, citrulline, or ornithine, as well as a variety of other molecules as identified herein. Similarly, J may comprise α-aminobutanoic acid (also known as α-aminobutyric acid), α-aminopentanoic acid, α-aminohexanoic acid, and a variety of other molecules identified herein.

Further, substituted amino acids which are not generally derived from proteins, but which are known in nature, are useful as disclosed herein, include the following examples: L-canavanine; 1-methyl-L-histidine; 3-methyl-L-histidine; 2-methyl L-histidine; α,ε-diaminopimelic acid (L form, meso form, or both); sarcosine; L-ornithine betaine; betaine of histidine (herzynine); L-citrulline; L-phosphoarginine; D-octopine; o-carbamyl-D-serine; γ-aminobutanoic acid; and β-lysine. D-amino acids and D-amino acid analogs, including the following, are also useful in proteins, peptides and compositions of the present invention: D-alanine, D-serine, D-valine, D-leucine, D-isoleucine, D-alloisoleucine, D-phenylalanine, D-glutamic acid, D-proline, and D-allohydroxyproline, to name some examples. The foregoing may also be used in surfactant molecules according to the present invention; particularly preferred for use accordingly are those corresponding to the formula $\{(\text{Charged})_a(\text{Uncharged})_b\}_c(\text{Charged})_d$.

The present invention also discloses that an extensive variety of amino acids, including metabolites and catabolites thereof, may be incorporated into molecules which display a surfactant activity. For example, molecules such as ornithine, homoarginine, citrulline, and a-aminobutanoic acid are useful components of molecules displaying surfactant activity as described herein. Surfactant molecules according to the present invention may also comprise longer straight-chain molecules; α-aminopentanoic acid and α-aminohexanoic acid are two additional examples of such useful molecules.

It should also be appreciated that the present invention encompasses a wide variety of modified amino acids, including analogs, metabolites, catabolites, and derivatives, irrespective of the time or location at which modification occurs. In essence, one may place modified amino acids into three categories: (1) catabolites and metabolites of amino acids; (2) modified amino acids generated via posttranslational modification (e.g., modification of side chains); and (3) modifications made to amino acids via non-metabolic or non-catabolic processes (e.g., the synthesis of modified amino acids or derivatives in the laboratory).

The present invention also contemplates that one may readily design side chains of the amino acids of residue units that include longer or shortened side chains by adding or subtracting methylene groups in either linear, branched chain, or hydrocarbon or heterocyclic ring arrangements. The linear and branched chain structures may also contain non-carbon atoms such as S, O, or N. Fatty acids may also be useful constituents of surfactant molecules herein. The designed side chains may terminate with (R') or without (R) charged or polar group appendages.

In addition, analogs, including molecules resulting from the use of different linkers, are also useful as disclosed herein. Molecules with side chains linked together via linkages other than the amide linkage—e.g., molecules containing amino acid side chains or other side chains (R- or R'-) wherein the components are linked via carboxy- or phospho-esters, ethylene, methylene, ketone or ether linkages, to name a few examples—are also useful as disclosed herein. In essence, any amino acid side chain, R or R' group-containing molecule may be useful as disclosed herein, as long as the molecule includes alternating hydrophilic and hydrophobic residues (i.e., component molecules) and displays surfactant activity as described herein.

The present invention also contemplates molecules comprising peptide dimers joined by an appropriate linker—e.g., peptide dimers linked by cystine molecules. (As those of skill in the art are aware, two cysteine molecules may be linked together by a disulfide bridge formed by oxidation of their thiol groups.) Such linkers or bridges may thus cross-link different polypeptide chains, dimers, trimers, and the like. Other useful linkers which may be used to connect peptide dimers and/or other peptide multimers include those listed above—e.g., carboxy- or phospho-ester, ethylene, methylene, ketone or ether linkages, to name a few examples.

While it is appreciated that many useful polypeptides disclosed herein—e.g., the KL4 polypeptide (SEQ ID NO 1)—comprise naturally-occurring amino acids in the "L" form which are joined via peptide linkages, it should also be understood that molecules including amino acid side chain analogs, non-amide linkages (e.g., differing backbones) may also display a significant surfactant activity and may possess other advantages, as well. For example, if it is desirable to construct a molecule (e.g., for use in a surfactant composition) that is not readily degraded, one may wish to synthesize a polypeptide molecule comprising a series of D-amino acids. Molecules comprising a series of amino acids linked via a "retro" backbone—i.e., a molecule that has internal amide bonds constructed in the reverse direction of carboxyl terminus to amino terminus—are also more difficult to degrade and may thus be useful in various applications, as described herein. For example, the following illustrates an exemplary molecule with a "retro" bond in the backbone:

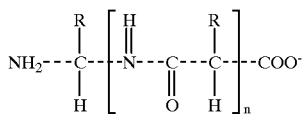

In another variation, one may wish to construct a molecule that adopts a more "rigid" conformation; one means of accomplishing this would be to add methyl or other groups to the a carbon atom of the amino acids.

As noted above, other groups besides a $CH_3$ group may be added to the a carbon atom—that is, surfactant molecules of the present invention are not limited to those incorporating a $CH_3$ at the α carbon alone. For example, any of the side chains and molecules described above may be substituted for the indicated $CH_3$ group at the α carbon component.

As used herein, the terms "analogs" and "derivatives" of polypeptides and amino acid residues are intended to encompass metabolites and catabolites of amino acids, as well as molecules which include linkages, backbones, side-chains or side-groups which differ from those ordinarily found in what are termed "naturally-occurring" L-form amino acids. (The terms "analog" and "derivative" may also conveniently be used interchangeably herein.) Thus, D-amino acids, molecules which mimic amino acids and amino acids with "designed" side chains (i.e., that can substitute for one or more amino acids in a molecule having surfactant activity) are also encompassed by the terms "analogs" and "derivatives" herein.

A wide assortment of useful surfactant molecules, including amino acids having one or more extended or substituted R or R' groups, is also contemplated by the present invention. Again, one of skill in the art should appreciate from the disclosures that one may make a variety of modifications to individual amino acids, to the linkages, and/or to the chain itself—which modifications will produce molecules falling within the scope of the present invention—as long as the resulting molecule possesses surfactant activity as described herein.

F. Therapeutic Methods

The present application also discloses a variety of therapeutic methods that are useful in conjunction with various novel compounds and compositions disclosed herein. While the use of $KL_4$-surfactant is described herein as exemplary, it should be understood that the other compounds and compositions disclosed herein—as well as compounds and compositions having surfactant activity and known to those of skill in the art—are also useful according to the described methods.

The present invention also discloses preferred methods of treating respiratory distress syndrome in patients of any age, including neonates and adults. One such method comprises administering to a patient in need of such treatment a therapeutically effective amount of a surfactant composition—preferably, a liposomal surfactant composition—prepared from a polypeptide (or other surfactant molecule) of the present invention and a pharmaceutically acceptable phospholipid, wherein the polypeptide is combined with the phospholipid in an amount sufficient to increase the surfactant activity of the composition above that of the phospholipid. The present invention also discloses a method of treating respiratory distress syndrome wherein the polypeptide is constituted by about 10–60 amino acid residues and alternating groupings of charged amino acid residues and uncharged amino acid residues as represented by the formula $[(\text{Charged})_a(\text{Uncharged})_b]_c(\text{Charged})_d$, wherein a has an average value of about 1 to about 5; b has an average value of about 3 to about 20; c is 1 to 10; and d is 0 to 3. In various preferred embodiments, such a polypeptide, when admixed with a pharmaceutically acceptable phospholipid, forms a pulmonary surfactant having a surfactant activity greater than the surfactant activity of the phospholipid alone.

As illustrated in the various Examples set forth below, a variety of methods for administering the surfactant compounds and compositions of the present invention are available. Depending on the needs of any individual needing treatment—e.g., an infant or adult with respiratory distress syndrome—different treatment methods may be appropriate.

Thus, in instances in which an infant has aspirated meconium, particular treatment modalities may be recommended. In one such therapeutic method, lavage of the patient's lungs with a surfactant composition of the present invention is performed. A single lavage with surfactant may be all that is required; alternatively, multiple surfactant lavages may be appropriate. Moreover, a saline lavage followed by one or more surfactant lavages may be an appropriate treatment—albeit it will be shown below that dilute surfactant lavage tends to produce better results than a combination of saline and surfactant lavage.

Lavage procedures using surfactant are performed essentially as follows. $KL_4$-surfactant or another surfactant (e.g. one of the present invention) is preferably administered using tools typically used in saline lavage procedures, which include various flexible tube-like apparatus such as endotracheal tubes, cannulas and catheters. Thus, for example, an endotracheal tube apparatus which includes a cannula that may be inserted through the tube—e.g. for suctioning purposes—is appropriate for use according to the disclosed methods. Preferably, any apparatus appropriately used to safely and efficaciously deliver and remove lavage fluids to and from the lung, respectively, is contemplated for use herein.

Exemplary devices for pulmonary lavage are ventilator devices equipped for bronchoalveolar lavage (BAL), which must include a means for applying a positive ene-expiratory pressure (PEEP) to the lung, a means for instilling liquids into the lung and a means for removing pulmonary fluids from the lung using negative pressure suction.

Representative devices are described in U.S. Pat. Nos. 4,895,719, 5,207,220, 5,299,566 and 5,309,903, the disclosures of which are hereby incorporated by reference.

As shown herein, particularly advantageous results were obtained by practicing a method of pulmonary lavage using dilute surfactant that produced sustained recovery of arterial oxygen ($PaO_2$), normal lung compliance and diminished inflammation following pulmonary injury by meconium aspiration or by partial loss of intrinsic surfactant, such as is demonstrated herein in the model using instillation of bacterial LPS. These methods are believed useful for use in treating any of a variety of pulmonary conditions in which there is respiratory distress, particularly acute respiratory distress syndrome (ARDS).

Conditions in which respiratory stress may be present include, but are not limited to, meconium aspiration in newborn infants, pulmonary inflammation, pulmonary infection. Respiratory distress can be associated with a variety of conditions, including sepsis, pulmonary trauma, accumulation of pulmonary exudate, pancreatitis, aspiration of gastric contents, heated gas inhalation, smoke or noxious gas inhalation, acute hypoxemia, fetal circulation, congenital diaphramatic hernia, pneumonia, inflammation arising from infection or multiple transfusions, and the like.

As shown herein, the present dilute surfactant lavage methods remove mediators of inflammation and simultaneously preserve and/or restore pulmonary function, thereby providing effective therapy.

The application of the pulmonary lavage provides several beneficial features. The washing effect of the lavage removes debris, dead cells, loose inflammatory cells and fluids, and the like, cleaning the alveoli of occluding fluid and materials, and removing typically 30 to 95% of the pulmonary and lavage fluids, together with any undesirable materials, such as meconium or inflammatory exudates. The dilute surfactant treats the alveolar membranes, improving the compliance of the tissue. The application of specified amounts of ventilator air pressure in the form of positive end-expiratory pressure (PEEP) before, during and after lavage with surfactant expands the lungs to maximize contact in the wash and treatment phase and thereby improve the dynamics of the lavage process, and in particular improves the oxygen tension and gas exchange in the patient during a process that can precariously burden oxygen exchange in the alveoli. Finally, the use of short intervals of tracheobronchial suction to remove the pulmonary (lavage) fluids are carefully administered in a manner that does not allow the arterial oxygen saturation to be reduced below acceptable and safe levels.

The pulmonary lavage method can be practiced on any mammal, and is particularly suited for humans, including adults, juveniles and infants, both newborn infants and babies experiencing respiratory distress.

The method for pulmonary lavage of a mammal comprises applying vapor phase (gas) positive end-expiratory pressure (PEEP) with a ventilator means to a lung, lung section or lobe of the mammal. Thereafter, a lavage composition containing dilute surfactant in a pharmaceutically acceptable aqueous medium is instilled into the lung or lung section of the mammal. Afterwards, some or all pulmonary fluid, including the lavage composition, present in the lung section is removed by applying short intervals of tracheobronchial suction using negative pressure.

The PEEP is typically administered at a pressure range of 4 to 20 centimeters (cm) water, although the pressure can vary depending on the patient and the pulmonary condition. For adults, juveniles and infants other than newborns, in which the lungs have toughened, the range is preferably from 6 to 12 cm water, and more preferably about 8–10 cm water. For newborn infants in which the lung sacs are more delicate and more fragile to applied pressure, the PEEP can range from about 4 to 15 cm water, preferably about 6 to 9 cm water, and more preferably about 8 cm water.

The administration of gas PEEP is typically applied to the lung prior to instilling dilute surfactant lavage, typically for up to about 30 minutes prior, more preferably about 5 to 30 minutes, in order to stabilize the blood oxygen prior to the procedure. In addition, PEEP is preferably applied continuously throughout the procedure during both the instilling and removing steps. It is to be understood that the combined effect on pressure of applying continuous PEEP and a short interval of suction will result in a brief, transient, drop in net pressure, with a rapid return to the maintained PEEP level when the suction interval is terminated. In addition, PEEP can be applied for a time period after the lavage fluid removal step in order to maintain oxygen tension on the alveoli following the procedure. Preferably, PEEP is maintained for up to about 24 hours after the removing step, preferably up to about 12 hours, and more preferably about 0.5 to 6 hours.

It is also contemplated that the applied gas can contain supplemental oxygen, typically from about 21 to 100% oxygen, preferably about 50 to 100% oxygen.

The suction phase of the method to remove the lavage and pulmonary fluids is administered in short intervals, i.e, 1 to 120 seconds. A typical suctioning interval is less than 30 seconds, preferably less than 20 seconds, and more preferably for about 5 to 20 seconds. A preferred interval is from 2 to 120 seconds, and preferably 5 to 20 seconds. The suction time period is short in order to minimize decreases in and saturated arterial oxygen ($SaO_2$) that may accompany the suction phase of the lavage procedure.

In one permutation of the suction procedure where there is more than one suction required to remove the pulmonary fluid, it is desirable to pause between short suction intervals rather than to follow one suction interval immediately with another in order to provide the opportunity for the $PaO_2$ level to recover. A typical pause period is from about 30 seconds to fifteen minutes, preferably about 1–5 minutes.

The suction applied to remove pulmonary fluids is a negative pressure of from about 10 to 150 millimeters (mm) mercury (Hg), preferably about 20 to 120 mm Hg, and more preferably about 60 to 100 mm Hg. A suction catheter or similar suction means is present in the ventilator device, typically as a cannula extending through the ventilator tube of the apparatus and into the bronchus. The cannula tip is typically guided into a segmental bronchus with the aid of the fiber optic observing means, and the instilling and removing are provided through the cannula tip.

In practicing the dilute lavage method, it is understood that the lavage can be administered repeatedly. Thus, the instilling and removing steps are repeated sequentially while applying PEEP as described herein. Typically, instilling and removing (lavage wash cycles) can be repeated in sequence from 2 to 5 times, although additional repetitions can be conducted if warranted. In addition, the content of the dilute surfactant can be varied over the course of the repeated lavage washes. For example, it is contemplated that a first series of from 1 to 3 wash cycles are conducted using dilute surfactant at a concentration of about 0.1 to 10 mg per ml lavage composition, and a second series of from 1 to 5 wash cycles are conducted using dilute surfactant at a concentration of about 10 to 50 mg per ml.

Depending on the position of the endotracheal tube apparatus in lung, the lavage composition will bathe a lung lobe, a lung segment or an entire side of lung, this being determined by the position in the bronchial tube where the apparatus terminates. Thus, it is understood that the term "lung" connotes alternatively that a lung lobe, a lung segment, a lung half containing two or three lobes, or a whole lung is being referred to in the context of the method, but adjusted for volume based on weight of the patient.

In instilling a lavage composition, it is also understood that the process can be conducted by a variety of methods, such as by cannula, by bronchoscope, by endotracheal tube and the like. In a preferred method, the instilling is typically monitored visually by a means for observing the lung at the apparatus tube terminus, typically by use of a fiber optic bronchoscope and illuminating means for visual display of the bronchial tube and distal lung lobe(s). Thus, although estimates of the appropriate lavage composition volume are stated, it is understood that in practice, the instilled volume may depend on the judgement of the practitioner during the instilling process, aided by the observing means.

The pulmonary lavage process is typically conducted on as many lungs, both left and right, and involved lung lobes, as needed depending on the extent of the condition of the lungs. Typically the procedure is conducted sequentially on 30 to 100% of the bronchial segments of the left and right lungs.

The bronchoscope or endotracheal tube may be fitted with a fixed or expanding collar designed to fit the inner diameter of a bronchial passage, and thereby secure a fit that can withstand the pressure ranges for practicing the method. This feature is particularly desirable insofar as it allows a section of the lung to be lavaged while the remaining lung portions can respire, thereby minimizing the trauma of the procedure to gas exchange in the patient.

$KL_4$-Surfactant solution or other novel surfactant solutions according to the present invention may be administered via lavage in a formulation appropriate for this procedure. While we have found that a formulation of surfactant comprising about 10–20 ml/kg is useful in the treatment of respiratory distress syndrome, formulations for lavage therapy tend to be more dilute, to facilitate efficient delivery and removal via endotracheal tube.

Thus, a "dilute surfactant" when used in the context of a lavage composition indicates that the lavage composition contains one or more substances which provide surfactant activity to the composition as defined herein in an amount sufficient to provide the surfactant activity but present in an amount such that the composition has a liquid viscosity amenable to lavage.

Thus, a surfactant-containing composition useful for administration to a subject (or patient) via lavage is preferably diluted to a concentration of about up to about 50 mg/ml so long as the viscosity is such that the composition is amenable to suction removal in less than 30 seconds following instillation. Dosages in the range of about 0.1–50 mg/ml are typically contemplated for use herein. In addition, the administration of higher dosages may be appropriate in various instances—e.g., when the subject is not fully responsive to lower dosages, or where the formulation lowers viscosity while allowing for increased concentrations of surfactant activity-containing substances.

In general, quantities of surfactant of about 4 to 60 ml per kg of the subject's (or patient's) body weight are given during each administration, typically divided equally between right lung and left lung or divided among lung sections. Depending on the needs of the individual patient—which may readily be determined by the physician or other individual of skill in the relevant art who is administering the treatment—greater or lesser quantities of surfactant may be delivered during each administration. Quantities comprising about 8–30 ml/kg are preferred, with quantities comprising about 10–25 ml/kg being somewhat more preferred. Thus, lavage composition is typically instilled in a volume of about 4 to 60 ml per kilogram (kg), preferably about 8 to 30 ml per kg, and more preferably about 16–25 ml per kg.

In describing the amount of surfactant present in a lavage composition, the weight refers to an amount measured as phospholipid phosphate per total volume of lavage composition, unless otherwise specified.

The amount of surfactant administered via lavage may also be described "per lung" in a particular patient. Thus, an effective amount of surfactant for lavage purposes may comprise about 200–800 ml/lung for a 70 kg adult, preferably about 400 ml/lung, and about 30–60 ml/lung for a 3 kg infant, preferably about 50 ml/lung. As before, depending on the maturity and size of the individual receiving treatment, the amount of surfactant administered—as well as the dosage—may be adjusted as appropriate.

A subject may receive one or more lavages, depending on the severity of the individual's condition and depending on the response of the subject to the first lavage. The dosages and amounts of surfactant administered may likewise vary in subsequent lavages. For example, if a subject receives a typical dose during the first lavage, subsequent lavages may be administered using the same dosage, a lesser dosage, or a higher dosage, depending on the needs and response of the subject.

Similarly, the amounts of surfactant administered during each lavage may vary—or may remain constant—depending on the needs of the individual patient. In appropriate circumstances, the first or subsequent lavage may be followed by a lavage administering a higher dose—e.g., up to 10–50 mg/ml. For example, a subject may receive 1–3 lavages with surfactant at a concentration of 0.1–10 mg/ml followed by 1–5 lavages with surfactant at a concentration of 10–50 mg/ml.

As noted previously, the dosage to be administered varies with the size and maturity of the subject, as well as with the severity of the subject's condition. Those of skill in the relevant art will be readily able to determine these factors and to adjust the dosage administered via lavage, as taught herein.

Bolus administration of surfactant may also be appropriate. Thus, for example, a bolus of 10–300 mg/kg surfactant at 15–100 mg/ml may be administered prior to or subsequent to one or more lavage treatments.

The type of treatment, dosage and amount utilized will understandably vary depending on the nature and seriousness of an individual subject's condition. Thus, for example, if a subject is an infant suffering from meconium aspiration, a treatment regimen comprising one or more surfactant lavages will likely be administered. Bolus administration of surfactant may follow the lavage(s) as well.

As noted previously, one aspect of the present invention was the removal of meconium or inflammatory exudate from the airways via lavage with dilute surfactant, in order to improve pulmonary function and inhibit the inflammatory reaction that usually develops in response to the presence of meconium or other injurious substances in the respiratory pathway. Although many of the examples focus on the use of one preferred embodiment—e.g., a synthetic peptide-containing exogenous surfactant—it is expressly to be understood that other surfactant-containing lavage compositions may be used according to the disclosed methods. Exemplary formulations for, and methods of using, surfactants are also disclosed in the present specification.

The following examples are intended to illustrate, but not limit, the present invention.

EXAMPLES

1. Preparation of Surfactant Compositions

Materials. 1,2-dipalmitoyl phosphatidylcholine (DPPC) and 1-palmitoyl, 2-oleoyl phosphatidylglycerol (POPG), and palmitic acid (PA) were obtained from Avanti Polar Lipids Inc. (Birmingham, Ala.). L-α-Dipalmitoyl-[dipalmitoyl-1-$^{14}$C]-phosphatidylcholine ($^{14}$C-DDC) was obtained from New England Nuclear (Boston, Mass.). $KL_4$ peptide with the amino acid sequence KLLLLKLLLLKLLLLKLLLLK was synthesized as described herein or obtained from the R. W. Johnson Pharmaceutical Research Institute (La Jolla, Calif.). All salts, buffers and organic solvents used were of the highest grade available.

Procedures. Synthesis of a peptide of the present invention—e.g., $KL_4$—may be carried out according to a variety of known methods of synthesis. The following procedure is described as exemplary. $KL_4$ peptide (9 mg), DPPC (225 mg), POPG (75 mg) and PA (45 mg) were dissolved in 2.5 milliliters (ml) of 95% ethanol at 45° C. This solution was then added to 7.5 ml of distilled $H_2O$ at 45° C. with rapid vortexing and 2 ml of 500 mM NaCl, 250 mM Tris-acetate pH 7.2 was subsequently added. The resulting milky suspension was stirred at 37° C. for 15 minutes and the ethanol present was then removed by dialysis (Spectrapor 2; 13,000 mol. wt. cutoff) against 100 volumes of 130 mM NaCl, 20 mM Tris-acetate pH 7.2 buffer at 37° C. Dialysis was continued for 48 hours with two changes of the dialysis solution.

Alternatively, the following procedure is also useful in synthesizing batches of peptide—e.g., $KL_4$ peptide—used as described herein. Chemicals and reagents used in the synthesis of surfactant peptides include the following:

t-Boc-L-lysine(Cl-Z) PAM-resin (t-Boc-L-Lys(Cl-Z); Applied Biosystems, Foster City, Calif.);

a-Boc-∈-(2-Chloro-CBZ)-L-Lysine (Bachem, San Diego, Calif.);

N-Boc-L-Leucine-$H_2O$ (N-Boc-L-Leu; Bachem);

Dichloromethane (DCM; EM Science, Gibbstown, N.J., or Fisher, Pittsburgh, Pa.);

Trifluoroacetic acid (TFA; Halocarbon);

Diisopropylethylamine (DIEA; Aldrich, Aldrich, Mich.);

N,N-Dimethylformamide (DMF; EM Science, Gibbstown, N.J.);

Dimethylsulfoxide (DMSO; Aldrich);

N-Methylpyrrolidone (NMP; Burdick & Jackson, Muskegon, Mich.);

1-Hydroxybenzotriazole hydrate (HOBt; Aldrich);

1,3-Dicyclohexylcarbodiimide (DCC; Aldrich);

Acetic anhydride ($Ac_2O$ ; Mallinckrodt, St. Louis, Mo.); and

Hydrogen fluoride (HF; Air Products, Allentown, Pa.).

One means of synthesizing $KL_4$ peptide is performed on a Coupler 296 Peptide Synthesizer (Vega Biotechnologies, Tucson, Ariz.) using the Merrifield method (see FIG. 1). A "typical" synthesis is described as follows. Chain elongation was carried out on 100 g of lysine PAM-resin by the procedure described in Table 2 below. All steps except steps 7, 10 and 11 were done automatically.

TABLE 2

Program for a Cycle Using the HOBt Active Ester Procedure

| Step | Reagent | Time | Volume |
|---|---|---|---|
| 1 | 50% TFA/$CH_2Cl_2$ | 1 × 2 min | 1.8 liters |
| 2 | 50% TFA/$CH_2Cl_2$ | 1 × 20 min | 1.5 liters |
| 3 | CH2Cl2 | 5 × 20 sec | 1.7 liters |
| 4 | 5% DIEA/$CH_2Cl_2$ | 1 × 2 min | 1.7 liters |
| 5 | 5% DIEA/NMP | 1 × 3 min | 1.7 liters |
| 6 | DMF | 5 × 30 sec | 1.7 liters |
| 7 | BOC AA-HOBt active ester | 1 × 39 min | 1.0 liters |
| 8 | DIEA/DMSO (195 ml/285 ml) | 1 × 21 min | 0.5 liters |
| 9 | DMF | 3 × 30 sec | 1.7 liters |
| 10 | 10% $Ac_2O$/ 5% DIEA/NMP | 1 × 8 min | 2.0 liters |
| 11 | $CH_2Cl_2$ | 3 × 30 sec | 1.7 liters |

While the peptide-resin was being deprotected, the appropriate amino acid derivative was being made. The appropriate amino acid was dissolved in one (1) liter of NMP. After a clear solution was obtained, HOBt was added to the solution. When the HOBt was dissolved, DCC was added to the solution. This solution was left stirring for one (1) hour at room temperature. During this one hour of stirring, a by-product formed, didyclohexylurea (a white precipitate). This by-product was filtered off through a buchner funnel using Whatman's #1 filter paper. The filtrate was then added manually to the contents of the Vega 296 reaction vessel at step No. 7.

The synthesizer was then programmed to stop after the completion of step No. 9. Aliquots of the peptide resin were subjected to the quantitative ninhydrin test of Sarin et al. (Applied Biosystems 431A user manual, Appendix A). The coupling efficiencies were good throughout the entire synthesis. The unreacted peptide resin was acetylated after leucine 12 (cycle 9) and after leucine 5 (cycle 16). After each acetylation, the peptide resin was washed with dichloromethane (see Table 2, step 11).

At the end of the synthesis, the completed peptide resin was deprotected (removal of the Boc group) by completing steps 1–3 of the program (see Table 2). The deprotected peptide resin was then washed with ample volumes of absolute ethanol and dried in vacuo over $P_2O_5$. The weight of the dried, deprotected peptide resin was 256.48 grams. Since the batch was started with 100 g of t-Boc-Lysine (Cl-Z) $OCH_2$ PAM resin at a substitution of 0.64 mmoles/gram, the load corresponded to 64 mmoles. Subtracting out the initial 100 grams of resin, the weight gain was 156.48 grams. The molecular weight of the nascent protected peptide (excluding the C-terminal lysine anchored onto the resin) was 3011.604 g/mole.

HF Cleavage. The 256.48 gram lot of peptide resin was treated with hydrogen fluoride (HF) in three large aliquots. A Type V HF-Reaction Apparatus from Peninsula Laboratories (Belmont, Calif.) was used for the cleavage of the peptide resin using liquid hydrogen fluoride. the anisole was distilled before use. HF was used without any treatment. Dry ice, isopropanol and liquid nitrogen are required for cooling purposes.

For the first HF, approximately 88 g of the $KL_4$ peptide resin was placed into the one-liter reaction vessel with a magnetic stir bar. Twenty-five ml of distilled anisole was added to the peptide resin. After the entire system was assembled and leak-tested, HF was condensed into the reaction vessel until the overall level reached about 300 ml. Cleavage of the peptide from the resin was allowed to proceed for one hour at −4° C. Partial removal of HF was done by water aspirator for 1–2 hours. After the 1–2 hours, the rest of the HF was removed by high vacuum (mechanical vacuum pump) for 1–2 hours. The temperature of the reaction vessel remained at −4° C. throughout the HF removal process.

The HF apparatus was then equilibrated to atmospheric pressure and an oily sludge was found at the bottom of the reaction vessel. Cold anhydrous ether (700 ml, prechilled to −20° C.) was added to the contents of the reaction vessel. The resin clumps were triturated with ether using a glass rod. The ether was decanted after the resin settled. The resin was then washed with 500 ml of room temperature anhydrous ether and allowed to stir for about 5 min. The ether was decanted after the resin settled. The resin was washed until it became free-flowing (4–5 total washes). The resin was left in the fume hood to dry overnight.

The resulting dried HF-treated resin was then weighed and stored in the freezer. 1.021 grams of the dried HF-treated resin was removed and extracted with 50 ml of 50% acetic acid/water and allowed to stir for 30 min. The resin was filtered through a coarse sintered glass funnel, and the filtrate was collected in a lyophilizing jar. The filtrate was diluted with approximately 200 ml of water, shell frozen, and placed on the lyophilizer. The one (1) gram of extracted HF-treated resin yielded 569 mg of crude peptide. The following table summarizes the large scale HF treatments of the remaining $KL_4$ peptide resin.

| HF# | Wt. of Resin | Amt. of Anisole | Total Volume (HF + Anisole + Resin) |
| --- | --- | --- | --- |
| 1 | 88.07 g | 25 ml | 300 ml |
| 2 | 85.99 g | 25 ml | 300 ml |
| 3 | 79.35 g | 25 ml | 300 ml |

All of the HF-treated resins were stored in the freezer.

Purification. The peptide was purified using a Dorr-Oliver Model B preparative HPLC (Dorr-Oliver, Inc., Milford, Conn.). This unit was connected to a Linear Model 204 spectrophotometer and Kipp and Zonen dual channel recorder. This preparative HPLC was interfaced with a Waters KIL250 Column Module (Waters Associates, Milford, Mass.) containing a radially compressed 10×60 cm cartridge filled with Vydac $C_4$ support, 15–20 microns, and 300 A pore size (Vydac, Hesperia, Calif.). Solvent "A" consisted of 0.1% HOAc in water, and solvent "B" consisted of 0.1% HOAc in acetonitrile. The flow rate was set at 400 ml/min, the cartridge was compressed to 150–200 psi, and the preparative HPLC system back pressure was at 550–600 psi.

For the first Dorr-Oliver run, 20 g of the HF treated resin from HF#1 was extracted in 500 ml of glacial acetic acid for five minutes. Water (500 ml) was added to the resin/acetic acid mixture. This 50% acetic acid/water solution was stirred for an additional 25 minutes. The resin was filtered off with a coarse sintered glass funnel. The peptide-containing filtrate was saved and loaded onto the Dorr-Oliver. The HPLC gradient used was 1–40% "B" in 45 minutes, then held isocratically for seven minutes. At this point, the percent "B" was increased 1% per minute to a final percentage of 44% (not shown).

Fractions were collected manually and were analyzed by HPLC. All fractions that met a purity of $\geq 95\%$ were pooled together and stored in a large glass container. This material was subsequently referred to as "BPS #1." All fractions that had the desired component, but did not meet the 95% or better purity, were collected and later recycled. At least 10 additional preparative HPLC runs were performed on the Dorr-Oliver unit (data not shown).

Reverse Osmosis, Lyophilization. The total volume of BPS #1 was approximately 60 liters. Reverse osmosis was used to concentrate the peptide solution to a final volume of two liters. A Millipore Model 6015 Reverse Osmosis Unit with an R74A membrane to retain the peptide was used. The resulting two liters of BPS #1 were filtered through a buchner funnel using two pieces of Whatman #1 filter paper, divided into approximately 11 lyophilizing jars and diluted with equal volumes of water. The lyophilizing jars were shell-frozen and lyophilized. The total weight of dry $KL_4$ peptide at the end of the procedure was 40.25 g. Re-lyophilization. It has been found that different lyophilizing conditions (e.g. peptide concentration, composition of solvents to be lyophilized, length of the lyophilization step, shelf temperature, etc.) can result in dried preparations having differing solubility characteristics. It is desirable that the dry $KL_4$ peptide be soluble in a chloroform: methanol (1:1) solution at 1 mg/ml and $\geq 90\%$ soluble at 10 mg/ml. If these criteria are not met at the end of the lyophilization step noted above, the peptide can be re-lyophilized. A typical re-lyophilization is described as follows.

Approximately 5 g of peptide is slowly added to two liters of acetonitrile stirring in a glass flask. After approximately one minute, three liters of Milli-Q water is added, followed by 50 ml of acetic acid (final concentration of acetic acid= 1%). This is stirred for three days at 37° C., filtered through Whatman #1 filter paper in a buchner funnel, and placed into a lyophilization jar. It is then shell frozen using dry ice and isopropyl alcohol and placed on the lyophilizer. Lyophilization time may vary from three to seven days. The final dry product is then weighed, packaged, and aliquots taken for solubility and chemical analyses.

2. Pharmaceutical Formulations

Surfactant compositions are formulated to contain 40 mg/mL total phospholipid, with a composition based on the following formula:

PL$_T$=total phospholipid=DPPC+POPG
3 DPPC:1 POPG
1 PL$_T$:0.15 PA:0.03 peptide.

Using the foregoing formula, the preferred composition per mL of finished product is essentially as follows:

| Component | Amount per mL |
|---|---|
| DPPC | 30.0 mg |
| POPG | 10.0 mg |
| PA | 6.0 mg |
| Peptide | 1.2 mg |

In addition, with regard to the buffer system/suspension, the composition may further comprise, per mL of finished product:

| Component | Amount per mL |
|---|---|
| Tromethamine, USP | 2.42 mg |
| Glacial acetic acid or NaOH, NF | quantity sufficient to adjust tromethamine buffer to pH 7.7 |
| NaCl, USP | 7.6 mg |

Water for inject., USP quantity sufficient to 1.0 mL

A Tham buffer system is prepared essentially as follows. 0.37 ml of Tham solution (tromethamine injection, NDC 0074–1593–04, Abbott Laboratories, North Chicago, Ill.), pH adjusted with acetic acid (AR Select, ACS, Mallinckrodt, Paris, Ky.) to a pH of 7.2±0.5, is admixed with 0.33 ml saline (0.9% sodium chloride injection, USP, Abbott Laboratories) and 0.30 ml water (sterile water for injection, USP, Abbott Laboratories) and is sterile-filtered.

3. In Vitro Assessment of Polypeptide Surfactant Activity

Measurement of Surfactant Activity. Measurements of surface pressure across an air-liquid interface (expressed in negative cm of H$_2$O pressure) at minimal ($\gamma$ min) bubble radius were determined at various times using the pulsating bubble technique described by Enhorning, *J. Appl. Physiol.*, 43:198–203 (1977).

Briefly, the Enhorning Surfactometer (Surfactometer International, Toronto, Ontario) measures the pressure gradient ($\Delta P$) across a liquid-air interface of a bubble that pulsates at a rate of 20 cycles/min between a maximal (0.55 mm) and minimal (0.4 mm) radius. The bubble, formed in a 37° C., water-enclosed, 20-$\mu$l sample chamber, is monitored through a microscopic optic while the pressure changes are recorded on a strip chart recorder calibrated for 0 and –2 cm H$_2$O.

Determination of Composite Hydrophobicity Value. The composite hydrophobicity value of each peptide was determined by assigning to each amino acid residue in a peptide its corresponding hydrophilicity value as described in Table 1 of Hopp et al, *PNAS USA*, 78:3824–3829 (1981), which disclosure is incorporated herein by reference. For a given peptide, the hydrophilicity values were summed, the sum representing the composite hydrophobicity value.

Preparation of Surfactants. After admixture with solvent, each peptide was combined with phospholipids (DPPC:PG), 3:1 to form a surfactant according to one of the following methods.

Method A was accomplished by admixing 16 $\mu$l of peptide/solvent admixture (40 $\mu$g peptide) with 100 $\mu$l of chloroform containing 400 $\mu$g phospholipids, agitating the admixture for about 10 at 37° C. to form a peptide/phospholipid admixture. Chloroform was removed from the peptide/phospholipid admixture by drying under N$_2$. The surfactant thus formed was then admixed with 90 $\mu$l of H$_2$O and gently agitated for about 10 minutes at 37° C. Subsequently, 10 $\mu$l of 9% NaCl was admixed to the surfactant-containing solution.

Method B was accomplished by first placing 100 $\mu$l of chloroform containing 400 $\mu$g of phospholipids in a glass tube and removing the chloroform by drying under N$_2$ for about 10 minutes at 37° C. Sixteen $\mu$l of peptide/solvent admixture and 74 $\mu$l H$_2$O were admixed with the dried phospholipids, and then gently agitated for about 10 minutes at 37° C. To the surfactant thus formed was admixed 10 $\mu$l of 9% NaCl.

Method C was accomplished by first maintaining the polypeptide-PL admixture at 43° C. for 10 minutes, after which time the solvents were removed from the admixture by drying under N$_2$. When needed, admixtures were further dried by 15 minutes exposure to vacuum to form a dried polypeptide-PL admixture. Water was then admixed with each dried admixture in an amount calculated to equal 90% of the volume necessary to give a final PL concentration of either 4 or 10 mg/ml (as indicated in Table 4) to form a second admixture. This second admixture was maintained for one hour at 43° C. with agitation. Subsequently, a volume of 6% NaCl equal to 10% of the volume necessary to give the desired PL concentration was admixed with the second admixture and the resulting final admixture was maintained for 10 minutes at 43° C. In most cases, the final admixture was subjected to a last step of 3 cycles of freezing and thawing.

Results. The surfactants illustrated in Table 3 were prepared as indicated in the table.

TABLE 3

| Peptide/ SEQ ID NO[1] | Solvent | (2) Admixture Formed | (3) Phospholipid Admixture Method | (4) Composite Hydrophobicity Value |
|---|---|---|---|---|
| p1–15/12 | n-propyl alcohol | suspension | A | –16.7 |
| p11–25/12 | H$_2$O | solution | B | +1.7 |
| p21–35/12 | Chloroform | suspension | A | –9.2 |
| p31–45/12 | H$_2$O | solution | B | –9.9 |
| p41–55/12 | H$_2$O | solution | B | –5.4 |
| p51–65/12 | H$_2$O | suspension | B | –2.2 |
| p81–75/12 | methanol | suspension | A | –9.9 |
| p71–81/12 | H$_2$O | suspension | B | +3.9 |
| p74–81/12 | H$_2$O | solution | B | +3.7 |
| p86–81/12 | methanol:H$_2$O | suspension | A | –1.0 |
| p52–81/12 | methanol:H$_2$O | suspension | A | –6.2 |

[1]All the identified peptides have an amino acid residue sequence corresponding to a portion of SEQ ID NO 12; for example, peptide p1–15 comprises amino acid residue nos. 1–15 of SEQ ID NO 12.
[2]Each polypeptide was admixed with the indicated solvent to achieve a concentration of 2.5 $\mu$g of peptide per 31 of solvent.
[3]The letters indicate the surfactant preparation method used. Those methods are described above.
[4]The composite hydrophobicity value of each peptide was determined as described above.

Each of the surfactants identified in Table 3 was assayed for surfactant activity as evidenced by their ability to reduce surface tension in vitro using the "bubble assay" of Enhorning as described above.

The results of this study (data not shown) indicate that a subject polypeptide, when admixed with pharmaceutically acceptable phospholipids, forms a pulmonary surfactant that has greater surfactant activity than the phospholipids alone, as evidenced by the lower $\Delta P$ values. Typically 10% to 80% lower AP values were obtained using the polypeptides. It should be noted that the eight amino acid residue control peptide p74–81, which does not conform to the teachings of the present invention, did not form a PS having a greater activity than the phospholipid alone, thus indicating that amino acid residue length is a critical feature.

The surfactant activity of additional exemplary polypeptides of this invention was studied using the "bubble assay" as described above. The results of the study are illustrated below in Table 4.

Each polypeptide was admixed with the indicated solvent at a concentration of 2.5 mg of polypeptide per ml of solvent. The resulting admixture was observed to determine whether a solution or a suspension of insoluble polypeptide was formed. Those admixtures forming a suspension were further admixed by water bath sonication for 10 seconds to form a very fine suspension, sufficient for pipetting using glass pipettes.

After admixture with solvent, each peptide was admixed with phospholipids (PL), DPPC:PG, 3:1, in chloroform in a glass tube so that the amount of polypeptide added equaled one-tenth (10% by weight) of the amount of PL added, to form a surfactant according to either method A, B or C.

Each of the surfactants was then assayed for surfactant activity as evidenced by their ability to reduce surface tension in vitro in the bubble assay performed as described above. The pressure gradient ($\Delta P$) is a measure of surfactant activity in the polypeptide-PL third admixture which was determined using an Enhorning Surfactometer as described above. Measurements were obtained at time points of 15 seconds (15"), 1 minute (1') and 5 minutes (5') and are expressed as a mean of three independent measurements of the indicated polypeptide-PL admixture. Pressure gradient measurements for comparable samples of PL alone (PL) and natural human surfactants were determined as controls. The results of this study are shown in Table 4.

TABLE 4

| Peptide[1] | Solvent | (2) Admixture Formed | (3) Phospholipid Admixture Method | (4) Conc. of PL mg/ml | (5) Pressure Gradient | | |
|---|---|---|---|---|---|---|---|
| | | | | | 15" | 1' | 5' |
| p1–15 | N-propanol | suspension | A | 4 | 0.94 | 0.82 | 0.48 |
| p36–81 | 50% chloroform 0% methanol | suspension | C+ | 10 | 0.90 | 0.87 | 0.79 |
| p46–76 | 64% chloroform 36% methanol | solution | C+ | 10 | 0.90 | 0.80 | 0.62 |
| p51–72 | 75% chloroform 25% methanol | suspension | C+ | 10 | 1.15 | 0.76 | 0.33 |
| p51–76 | 37% chloroform 63% methanol | solution | C+ | 10 | 0.99 | 0.91 | 0.42 |
| p51–80 | 45% chloroform 55% methanol | solution | C+ | 10 | 0.92 | 0.89 | 0.48 |
| p51–81 | 50% chloroform 50% methanol | suspension | C+ | 10 | 0.94 | 0.86 | 0.64 |
| p52–81 | 67% DMF 33% chloroform | solution | A | 4 | 1.33 | 1.19 | 0.96 |
| p54–72 | 76% chloroform 24% methanol | suspension | C+ | 10 | 1.28 | 0.92 | 0.38 |
| p54–76 | 71% chloroform 24% methanol | suspension | C+ | 10 | 0.92 | 0.82 | 0.23 |
| p59–81 | 68% chloroform 32% methanol | solution | C– | 4 | 1.08 | 1.02 | 0.75 |
| p66–81 | 40% DMF 60% chloroform | suspension | A | 4 | 1.22 | 1.11 | 0.84 |
| p74–81 | water | solution | B | 4 | 2.37 | 2.32 | 2.31 |
| DL4 (31 mer) | 47% chloroform 53% methanol | solution | C– | 4 | 2.00 | 1.80 | 1.30 |
| RL4 | 32% chloroform 68% methanol | solution | C– | 4 | 0.58 | 0.65 | 0.33 |
| RL8 | 19% chloroform 81% methanol | suspension | C+ | 10 | 0.68 | 0.69 | 0.19 |
| RL7 | 49% chloroform 51% methanol | solution | C– | 4 | 1.65 | 1.25 | 1.00 |
| RCL-1 | 79% chloroform 21% methanol | suspension | C+ | 10 | 0.50 | 0.59 | 0.06 |
| RCL-2 | 67% chloroform 33% methanol | suspension | C+ | 10 | 0.00 | 0.00 | 0.00 |
| RCL-3 | 75% chloroform 25% methanol | suspension | C+ | 10 | 0.55 | 0.51 | 0.33 |
| PL | | | C+ | 10 | >2.50 | >2.50 | 2.33 |
| Natural Human Surfactant | | | | 10 | 1.06 | 0.89 | 0.79 |

[1]All the identified peptides have an amino acid residue sequence corresponding to a portion of SEQ ID NO 12; for example, peptide p1–15 comprises amino acid residue nos. 1–15 of SEQ ID NO 12.
(2) Whether the initial admixture of peptide was a solution or a suspension is indicated.
(3) The letters indicate the surfactant preparation method used. Those methods are described above. A "+" indicates that the final admixture was subjected to a last step of 3 cycles of freezing and thawing. A "–" indicates the step was not performed.
(4) Concentration ("Conc.") of phospholipid (PL) in the final third admixture is indicated in milligrams PL per milliliter admixture (mg/ml).

TABLE 4-continued

| Peptide[1] | (2) Admixture Solvent | (3) Phospholipid Admixture Formed | (4) Conc. of PL Method mg/ml | (5) Pressure Gradient 15" 1' 5' |
|---|---|---|---|---|

(5) The pressure gradient is a measure of surfactant activity in the polypeptide-PL final admixture as determined using an Enhorning Surfactometer as described in Example 3. Measurements were obtained at three points of 15 seconds (15"), 1 minute (1') and 5 minutes (5') and are expressed as a mean of 3 independent measurements of the indicated polypeptide-PL admixture. Pressure gradient measurements for comparable samples of PL alone (PL) and natural human surfactant are also shown.

These results indicate that a subject polypeptide, when admixed with pharmaceutically acceptable phospholipids, forms a pulmonary surfactant that has a greater surfactant activity than the phospholipids alone, as demonstrated by the lower surface pressures obtained.

4. In Vivo Assessment of Surfactant Activity in a Rabbit Model

Preparation of Surfactants. A subject polypeptide was first admixed with solvent as described in Example 3. The resulting admixture was further admixed with phospholipid (PL) so that the amount of polypeptide added was either 3%, 7% or 10% by weight of the amount of PL added as indicated below. The final polypeptide, PL admixture (surfactant) was formed according to method C using the final freeze thaw step as described in detail in the "Preparation of Surfactants" section in Example 3, except that the final admixture had a concentration of 20 mg phospholipid per ml of final admixture.

Instillation Protocols.

Protocol 1: Fetal rabbits were treated by injection into the trachea of a 0.1 ml solution that contained either a synthetic surfactant prepared in Example 4 or either 2 mg of native surfactant prepared as described in Example 1 of U.S. Pat. No. 5,260,273 (incorporated by reference herein) or 2 mg PL.

Protocol 2: surfactant was instilled in rabbit fetal lung by injection into the trachea from a single syringe of the following three components such that the components exit the syringe in the following order: (1) 0.05 ml air; (2) 0.1 ml of a synthetic surfactant prepared in Example 4 or either 2 mg of PL or 2 mg of native surfactant; and (3) 0.1 ml air.

Protocol 3: From one syringe, a 0.1 ml aliquot of synthetic surfactant prepared as described in Example 4 (or 2 mg of NS or of PL), was instilled into the rabbit trachea as described above, followed by injection of 0.05 ml lactated Ringer's Solution and 0.2 ml air from a second syringe.

Protocol 4: From one syringe, 0.1 ml of a synthetic surfactant prepared as described in Example 4 (or 2 mg of NS or of PL), 0.15 ml air, 0.1 ml saline, and 0.3 ml air were injected into the trachea as described above. Two subsequent aliquots of 0.3 ml air were given.

Protocol 5: Fetal rabbits were treated by injection into the trachea from a single syringe the following four components such that the four components exit the syringe upon injection in the order listed: (1) 0.2 ml solution that contains either a synthetic surfactant prepared in Example 4 or either 4 mg of native surfactant, or 4 mg PL; (2) a 0.15 ml volume of air; (3) a 0.1 ml normal saline solution; and (4) a 0.3 ml volume of air. The above injection was then repeated 15 minutes after the first injection.

Protocol 6: Rabbits were treated as described in Protocol 5, except that two subsequent aliquots of 0.3 ml air were given following the initial instillation and no additional instillation was given at 15 min.

Fetal Rabbit Model for Studying Surfactant Activity

The surfactant activity of exemplary polypeptides of this invention was studied using the methods described in detail previously by Revak et al, *Am. Rev. Respir. Dis.*, 134:1258–1256 (1986), with the exceptions noted hereinbelow.

Twenty-seven day gestation fetal rabbits were delivered by hysterotomy and immediately injected with 0.05 ml Norcuron (Organon, Inc., N.J.) to prevent spontaneous breathing. The fetal rabbits were then weighed and a small cannula was inserted into the trachea by tracheotomy. surfactant prepared as described above was then instilled into the fetal rabbit lung by one of the above instillation protocols.

Following instillation the rabbit was placed in a specially designed plethysmograph (containing a Celesco transducer) connected to a ventilator (Baby Bird, Baby Bird Corp., Palm Springs, Calif.) and the instilled lung was ventilated at a rate of 30 cycles per minute with a peak inspiratory pressure of 25 cm $H_2O$, a positive end expiratory pressure (PEEP) of 4 cm $H_2O$ and an inspiratory time of 0.5 seconds. In some studies, dynamic compliance measurements were made at various times throughout the ventilation procedure. In others, static compliance measurements were made following ventilation.

Static compliance measurements were made after 30 minutes of ventilation. The animals were removed from the ventilator and the lungs were degassed at −20 cm $H_2O$ in a bell jar under vacuum. Thereafter, the lungs were first inflated and then deflated through a T-connector attached to a tracheostomy tube. The volume of air required to reach static pressures of 5, 10, 15, 20, 25 and 30 cm $H_2O$ was measured during both inflation and deflation phases to generate static pressure to volume curves as a measure of static compliance.

Using the plethysmograph, dynamic compliance measurements were made at various times throughout a 60 minute ventilation period. Computer-assisted data analysis resulted in compliance data expressed as ml of air per cm $H_2O$ per gram of body weight at each time point. Compliance was calculated by the formula below.

$$\text{Compliance} = \frac{\Delta V}{\Delta P}$$

$\Delta P_{tp} = (C)^{-1} \cdot (\Delta V) + (R) \cdot (F)$ $P_{tp}$=transpulmonary pressure C=compliance (elastic component—relates change in volume to pressure)

R=resistance (relates flow to pressure)

F=flow

V=volume=the integral of flow with respect to time

The above equation was solved with a multiple linear regression for C and R. The compliance (C) represents the elastic nature of the lungs and the resistance (R) represents the pressure necessary to overcome the resistance to the flow of gas into and out of the lungs.

Results. Static compliance data was collected using instillation protocols 1 and 5. Improved lung compliance was seen in all lungs treated with natural surfactant or with the surfactants of the present invention tested as compared with those lungs treated with phospholipids (PL) alone, with one exception. The surfactant prepared using p1–15 did not produce improved lung compliance over PL alone when measured by static compliance.

The results of the dynamic compliance studies are illustrated in Table 5.

real improvement over therapies and compositions described in the art relating to MAS.

In models of MAS of human infants, adult rabbits and newborn rhesus monkeys received intratracheal instillation of human meconium to induce pulmonary injury. The results presented herein indicate that pulmonary function in two models of severe meconium injury respond rapidly to bronchoalveolar lavages (BAL) containing dilute $KL_4$-Surfactant when administered as described.

a. Materials and Methods

I. Animal Models

Adult NZW rabbits, approximately 2.5 kg in weight and rhesus monkeys (Macaca mulatta) delivered at full term by

TABLE 5

Dynamic Compliance in ml air/cm $H_2O$ (g body weight × $10^6$)

| | % Peptide Compound to PL | \multicolumn{6}{c}{Minutes after Surfactant Instillation} | Sample[1] Given Protocol # |
|---|---|---|---|---|---|---|---|---|
| | | 10 | 20 | 30 | 40 | 50 | 60 | |
| PL | | | | | | | | |
| | | 7 | 8 | 7 | 10 | 11 | 15 | 4 |
| | | 24 | 22 | 23 | 23 | 22 | 20 | 4 |
| | | 15 | 16 | 17 | 18 | 21 | 29 | 4 |
| NS | | | | | | | | |
| | | 265 | 251 | 168 | 186 | 173 | 147* | 4 |
| | | 418 | 388 | 405 | 288 | 237 | * | 4 |
| | | 155 | 176 | 172 | | 172 | 179 | 4 |
| P36–81 | | | | | | | | |
| | 5% | | | 255 | | | 146* | 3 |
| | 5% | | | 245 | | | 291 | 3 |
| | 10% | | | 154 | | | 1,162 | 2 |
| | 10% | | | 252 | | | 623 | 2 |
| p52–81 | | | | | | | | |
| | 5% | | | 517 | | | 226* | 3 |
| | 5% | | | 434 | | | 55* | 3 |
| | 10% | | | 195 | | | 1,243 | 2 |
| | 10% | | | 43 | | | 1,690 | 2 |
| p51–76 | | | | | | | | |
| | 10% | 33 | 22 | 56 | 87 | 124 | 85 | 4 |
| | 10% | 10 | 11 | 186 | 358 | 141 | 144* | 4 |
| | 10% | 15 | 36 | 109 | 241 | 264 | 301 | 4 |
| p51–80 | | | | | | | | |
| | 10% | 17 | 41 | 52 | 78 | 99 | 208 | 4 |
| | 10% | 76 | 94 | 149 | 149 | 217 | 308 | 4 |
| | 10% | 23 | 71 | 130 | 156 | 182 | 109* | 4 |

[1]Prior to instillation into the rabbits, these samples were filtered through a 25 micron filter.
*A decrease in compliance with time may indicate the development of pneumothorax.

As shown in Table 5, each of the surfactants of this invention and natural surfactant improved dynamic compliance values in comparison to phospholipid alone.

Discussion. The in vivo compliance studies demonstrate that the use of a number of exemplary surfactants of this invention resulted in enhanced compliance in comparison to phospholipid alone for each of the assayed surfactants. Thus, the proteins and polypeptides of this invention when admixed with pharmaceutically acceptable phospholipids form surfactants that have greater surfactant activity than phospholipid alone. Use of the surfactants is advantageous in producing improved compliance values in vivo.

5. Use of Pulmonary Surfactant as a Therapeutic Agent in Meconium Aspiration Syndrome In view of the variability in efficacy achieved by using exogenous surfactant given as a bolus in the treatment of experimental and clinical Meconium Aspiration Syndrome (MAS), and in view of the somewhat equivocal results achieved when standard lavage methods are used, alternative therapeutic modalities are clearly needed. Therefore, the compositions and methods disclosed herein provide a very Caesarean section and weighing approximately 520 gms were employed.

The rabbits were studied at The Scripps Research Institute (La Jolla, Calif.) and the rhesus monkeys were examined at the California Primate Research Center (Davis, Calif.). The studies were approved by the Animal Research Committee of The Scripps Research Institute, and the Animal Use and Care Committee, UC Davis. All studies conformed to the requirements of the Animal Welfare Act and National Institutes of Health Guidelines.

ii. Meconium Preparation

The first stool passed by human infants was collected and stored frozen until pools were made representing meconium from 5–11 infants. Sterile water was added until a stirrable slurry was achieved. After freezing, the mixture was lyophilized and a dry weight obtained. Sterile saline was added in amounts calculated to yield a concentration of 50 mg (dry weight)/ml. The stock solutions were homogenized in a blender, filtered through gauze to remove particulate material and stored frozen until diluted for use. For most samples, the dry weight was 25–30% of the original wet weight. Meconium quantities are expressed as dry weight.

iii. KL$_4$-Surfactant

KL$_4$-Surfactant, a synthetic peptide-containing surfactant consisting of dipalmitoyl-sn-glycero-3-phosphocholine (DPPC), 1-palmitoyl-2-oleoyl-sn-glycero-3-phosphoglycerol (POPG), palmitic acid (PA), and a synthetic peptide of the sequence KLLLLKLLLLKLLLLKLLLLK, was prepared as described previously (Cochrane et al, *Am J Resp & Crit Care Med*, 152:404–410, 1996; Revak et al, *Ped. Res.*, 39:715–724, 1996).

Briefly, synthetic peptides, including KL$_4$, were synthesized using a solid phase peptide synthesizer and provided by R. W. Johnson Pharmaceutical Research Institute (La Jolla, Calif.). DPPC, POPG and palmitic acid were obtained from Avanti Polar Lipids (Birmingham, Ala.). Peptide-containing surfactant was prepared by mixing DPPC and POPG in a 3:1 ratio by weight with PA in which PA is present at 15% w/w with the lipids, and dissolving the mixture in organic solvent. Thereafter, the peptide was dissolved in organic solvent, and admixed with the lipid mixture at a ratio of 3% w/w of peptide per phospholipid weight. Organic solvents were removed by evaporation under nitrogen. Tris buffer was then added to form a liposomal surfactant composition at pH 7.2–7.4 and 250–350 mosmol/kg. Dilutions with saline were made as needed from the stock solution.

iv. Biochemical Assays

Protein assays were performed using a BCA reagent kit (Pierce, Rockford, Ill.) according to the manufacturer's instructions. Myeloperoxidase (MPO) was measured using a modification of the o-dianisidine method described by Steinman and Cohn for the measurement of horseradish peroxidase (Steinman et al, *J. Cell Biol.*, 55:186–204, 1972). Typically, 200 $\mu$l of 125 $\mu$g/ml o-dianisidine in 100 mM citrate buffer pH 6.0 were added to 20 $\mu$l of sample.

The change in absorbance at 405 nm over a 10 min period following the addition of 20 $\mu$l of 2 mM H$_2$O$_2$ was proportional to the amount of MPO present. A standard reference solution which caused an absorbance change of approximately 0.072 units/$\mu$l/10 min was used. One unit of MPO activity was defined as the activity in 1 $\mu$l of the reference solution.

Rabbit and monkey IL-8 were quantitated in lavage washes by a previously described ELISA method (Schraufstatter et al, *J. Immunol.*, 151:6418–6428, 1993).

Surfactant was isolated from rabbit or monkey lung lavage fluids by taking the supernatant from a 5 minute, 1000 rpm spin (which removed cells and debris) and subjecting it to a 1 hour spin at 40,000 g at 4° C. The precipitate from this high-speed spin was resuspended in $\frac{1}{20}$ the original volume of normal saline and quantitated as to the amount of phospholipid present by a modification of the method of Rouser et al, *Lipids*, 5:494–496 (1970).

Meconium was quantitated spectrophotometrically. Samples were centrifuged at 40,000×g for 1 hour. The optical density (OD) of the supernatant (or dilutions in saline) was read at 260 and 300 nm and the following formula applied: $OD_{300}-(0.13)(OD_{260})$. This formula was derived empirically from spectral analyses of multiple rabbit and monkey lavage samples with and without meconium; it was found to yield values of approximately zero for samples not containing meconium and a linear relationship was found to exist for solutions containing from 1 to 1600 $\mu$g/ml meconium.

Lavage samples from animals with pulmonary inflammation, determined microscopically, were found to have a unique absorption peak at approximately 400–405 nm which was not present in lavage fluids of normal animals. Using this observation and correcting for absorption of proteins with peaks <300 nm, an arbitrary "Inflammatory Index" was defined as $OD_{400}-(0.45)(OD_{305})$.

Cells present in lavage wash samples were evaluated by standard cell staining and counting techniques to identify PMN's and RBC's (erythrocytes).

V. Surface tension-lowering assay

The ability of surfactant to lower surface tension at an air-liquid interface was measured using a pulsating bubble surfactometer as described previously (Revak et al, *Am. Rev. Respir. Dis.*, 134:1258–1265, 1986). Samples were diluted to 3 mg/ml phospholipid before assay.

vi. Compliance assays

Compliance assays were performed on abbits prior to instillation of meconium, at 0.9 hours after meconium, i.e., just prior to treatment, and at about 5 hours after meconium instillation. Rabbits were treated with vecuronium bromide (0.1 ml/kg IV), briefly removed from the ventilator, connected to a pressure/volume monitoring circuit, with recording of volumes of air corresponding to increments of 5 cm H$_2$O pressure up to and down from 35 cm H$_2$O.

vii. Postmortem Examination

Rabbits and rhesus monkeys were sacrificed with IV barbiturate. The thorax was opened and heart and lungs removed en bloc with the trachea clamped under 10 cm H$_2$O pressure. Gross examination was performed with the tracheal pressure at both 10 cm H$_2$O and atmospheric pressure. One lung was placed in 10% Zn- formalin following ipsilateral ligation of the bronchus at 10 cm H$_2$O pressure for microscopic examination. The other lung received two lavages of approximately 2 ml/kg sterile saline each, placed in the same segment.

After removal of 0.1 ml for cell counts, lavage fluids were centrifuged at 1000×g 5 min to remove cells, and then 40,000×g 60 min to isolate the surfactant and provide lavage fluid for biochemical studies. For counts of polymorphonuclear leukocytes (PMNs) in histologic sections of the lung, a straight line was drawn on the coverslip within 2 mm of the mainstem bronchus of the lower lobe, traversing the entire section as a cross-section of the lung. Microscopic counts were then performed along the line from one pleural edge to the other. This method was chosen in view of the consistent injury produced by meconium to this area of the lower lobe and the consistency of treatment with KL$_4$-Surfactant or saline to this region of the lung.

viii. Statistical Analyses

Groups were compared using a two group unpaired t test. Statistical difference was taken as p<0.05.

b. Adult Rabbit Lavage Model and Instillation Protocols

Rabbits were divided into 4 treatment groups, as follows. Group 1 rabbits received bronchoalveolar lavages (BAL) with dilute KL$_4$-Surfactant. Group 2 animals received lavages with equal volumes of sterile saline. Group 3 rabbits received a single intratracheal bolus of KL$_4$-Surfactant, 100 mg/kg. Group 4 animals received no treatment—i.e., no lavages or boluses—at all.

As described hereinbelow, the untreated rabbits developed atelectasis, a fall in compliance and in PaO$_2$ from approximately 500 to <100 mm Hg, and severe pulmonary inflammation between 3–5 hours after instillation of meconium. Rabbits treated by BAL with dilute KL$_4$-Surfactant showed rapid and sustained recovery of PaO$_2$ to approximately 400 mm Hg within minutes, a return toward normal compliance and diminished inflammation. Rabbits receiving BAL with saline failed to show recovery, and rabbits treated with a bolus of surfactant intratracheally exhibited a transient response by 1–2 hours after treatment, but then returned to the initial atelectatic collapse.

Rabbits were anesthetized with intramuscular (IM) Xylazine and Ketamine. Tracheostomy was performed and a 3.0 mm internal diameter endotracheal tube inserted to a position at least 1 cm above the carina. An arterial line for blood samples was placed in the auricular artery. All animals were then placed on a pressure-cycled ventilator (Bird; 3M, St. Paul, Minn.). To induce pulmonary injury, meconium was instilled intratracheally. The appropriate volume of meconium was divided into two equal portions, one given with the rabbit held at 45° C. with its head up and the right side of the animal down, and the second half as before, but with the left side down.

Meconium was instilled through a cannula threaded through the endotracheal tube and reaching <0.5 cm beyond the tip of the endotracheal tube. Rabbits were placed on 100% $O_2$ for 10–15 min before instillation of meconium and received 100% $O_2$ for the duration of the study. After the meconium instillation, mechanical ventilation was begun with peak inspiratory pressure (PIP) of 25 cm $H_2O$, generally, and positive end expiratory pressure (PEEP) of 2 cm $H_2O$ and ventilatory rate of 20 breaths per minute. Blood gas determinations were performed approximately 10, 30 and 50 minutes after meconium instillation. After 1 hour, the rabbits were placed into one of four treatment groups, as follows.

Group 1 rabbits received bronchoalveolar lavage with $KL_4$-Surfactant diluted to 2–5 mg/ml, receiving 20 ml/kg divided into two equal portions, one lavaged into the right lung, and the second half into the left lung. The rabbit was given intravenous (IV) vecuronium bromide 0.1 ml/kg to induce paralysis, found to be essential for appropriate drainage in the lavage procedure. The $KL_4$-Surfactant was instilled with the ventilator on PEEP alone, at a pressure of 8 cm $H_2O$, i.e. without air movement. The animal was held head up at approximately 45° with, first, the right side down in order to instill surfactant into the right lung. Immediately after instillation of the dilute surfactant, intermittent ventilation (IMV) was re-started with PIP of 25 cm $H_2O$ and PEEP of 5 cm $H_2O$ for five breaths.

The rabbit was then disconnected from the ventilator and the lavage-surfactant and meconium were drained by tipping the rabbit head down at 30–45°. All lavage volumes were recorded along with the time required for the procedure. Drainage was continued with gentle massage of the chest until flow slowed considerably. The total time required for the lavage procedure was approximately 90 seconds. The rabbit was immediately placed back on IMV with the same settings (PIP, 25; and PEEP, 5) for 2–5 minutes. The lavage procedure was then repeated with the left side of the rabbit held down in order to lavage the left lung. This constituted the first lavage. Repeated lavages were performed similarly, each divided between right and left lungs. As noted in the text, a final lavage was performed with $KL_4$-Surfactant using a concentration of $KL_4$-Surfactant of 10 or 15 mg/ml; alternatively, in some animals, a bolus of $KL_4$-Surfactant was given at 30 mg/ml, (100–150 mg/kg) in order to provide sufficient levels of retained surfactant to maintain good pulmonary function.

Group 2 rabbits received bronchoalveolar lavage with sterile saline, performed as in (1), but using equal volumes of sterile saline.

Group 3 rabbits received instillation of a bolus of $KL_4$-Surfactant (i.e., without lavage) at a concentration of 30 mg/ml, using 100 mg/kg divided equally between right and left lungs.

Group 4 rabbits received no treatment of the meconium injury.

I. Response of adult rabbits to intratracheal administration of varying doses of human meconium Initial studies were performed to determine the response of adult rabbits to varying doses of a slurry of human meconium given intratracheally. Rabbits received the following doses of meconium (mg/kg in 5 to 7.5 ml/kg): 93.8 (n=3); 125 (n=4); 187.5 (n=7); 281.3 (n=2); 375 (n=1). While doses of 93.8 and 125 mg/kg produced a fall in $PaO_2$ and partial atelectasis in the lung, the effect was not consistent, and 71% of the rabbits showed signs of spontaneous recovery of $PaO_2$ by five (5) hours after instillation of the meconium.

At the dose of 187.5 mg/kg, a consistent fall in $PaO_2$ occurred within 1 hour of instillation of meconium and spontaneous recovery of $PaO_2$ by 5 hours was not observed (FIG. 3). Doses higher than 187.5 mg/kg also induced a fall in $PaO_2$, but with death occurring in 2 of the 3 rabbits.

The dose of 187.5 mg/kg in 7.5 ml/kg was selected for further study. In these rabbits, autopsies at 5–6 hours after instillation of meconium revealed marked atelectasis of the lungs (not shown), with dark red, non-expanded areas in at least 80% of the lung. Small rims or caps of expanded lung existed in the apical region of the upper lobes and in some instances, the lower lobes, presumably due to a failure of the meconium to reach these areas. Histologically, at 1–2 hours after administration of meconium, the alveoli were collapsed, but little evidence of inflammation was observed. With PAS stain, the meconium could be detected by its bright violet color, forming fine, amorphous clumps in the alveolar spaces, generally abutting the septae. There were no obstructive plugs of meconium observed in the bronchi, presumably as a result of filtration of the meconium preparation. At 5–6 hours after meconium was administered, the lungs revealed widespread atelectasis, with dense infiltration of edema and inflammatory cells, primarily, polymorphonuclear leukocytes (PMNs), together with red blood cells (RBCs) (not shown).

The gross and microscopic appearance of rabbit lungs was analyzed after the lungs were injured with meconium and treated as follows: A. no treatment; B. $KL_4$-Surfactant lavage; C. sterile saline lavage; D. $KL_4$-Surfactant bolus. Dark red atelectatic collapse was seen in groups in A, C and D, but generalized expansion was seen in B (not shown). The light regions of the upper lobes in A, C and D were devoid of meconium and were not injured. Microscopic sections were also taken, midway up the lower lobe. While most of the alveoli in the $KL_4$-Surfactant-lavaged lung showed gas expansion with a minimum of edema and PMNs, alveoli in lungs receiving no treatment, sterile saline lavage, or a bolus of surfactant contained abundant edema, PMNs and RBCs (not shown). Some alveoli in lung tissue receiving a surfactant bolus only contained gas bubbles, presumed to be retained from the bolus treatment with $KL_4$-Surfactant (not shown).

Figure 4A:
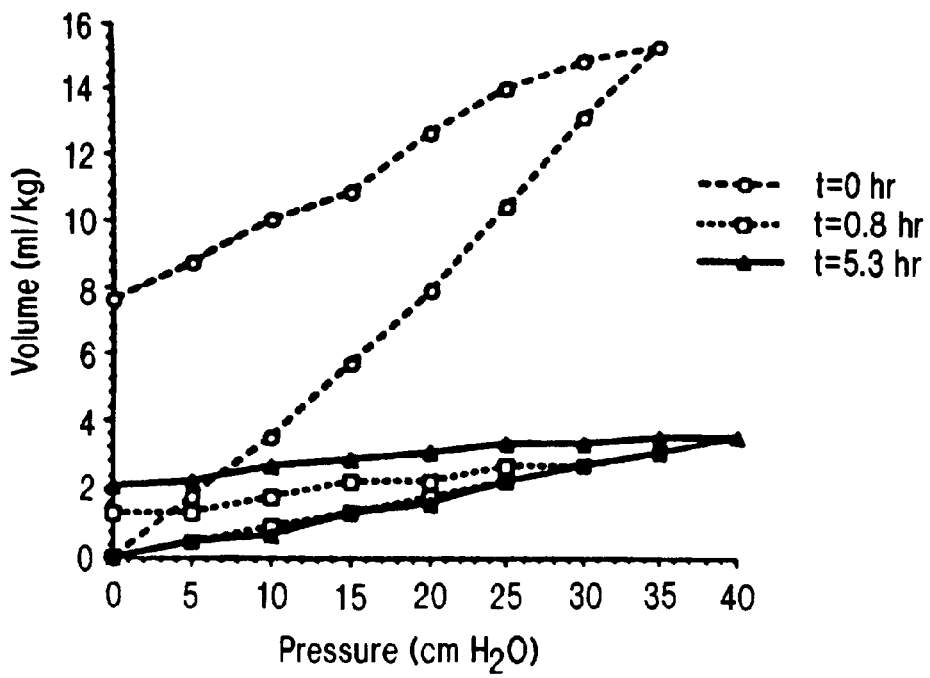
Figure 4B:
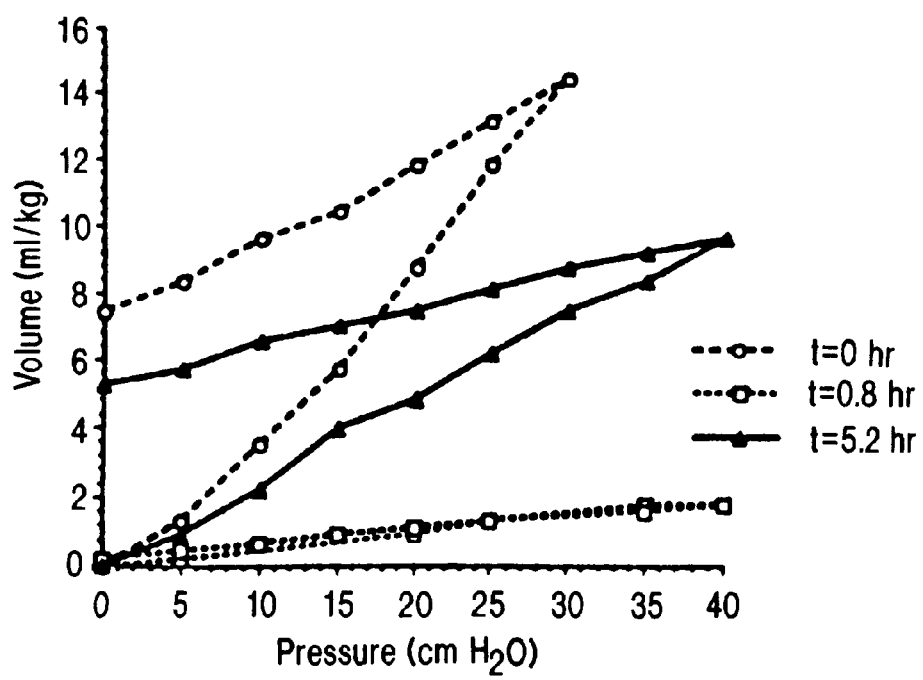
Figure 4C:
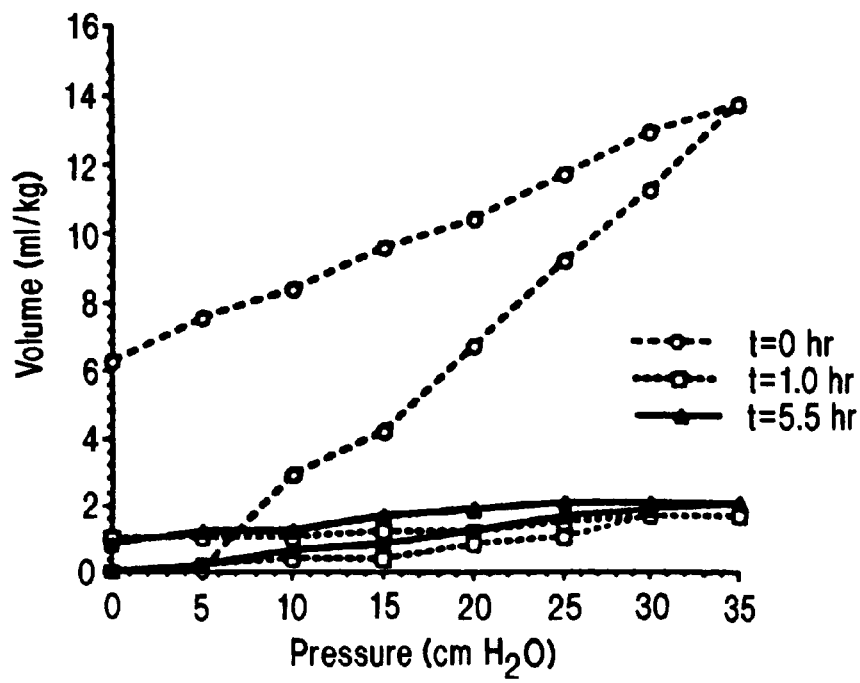
Figure 4D:
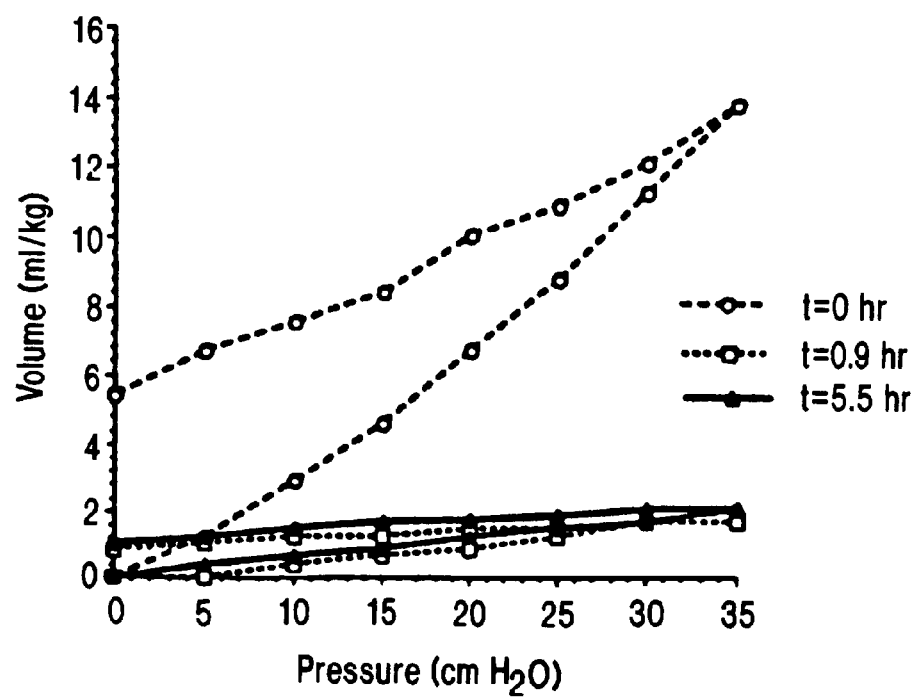

Static compliance assays were performed prior to, and one and 4–5 hours after, instillation of meconium. As shown in FIG. 4A and Table 6, the normal compliance curve, observed before instillation of meconium, was converted to a flat curve one hour after, and remained flat through 5 hours.

Experiments resulting in the data presented in Table 6 were performed essentially as described herein and more particularly as follows. Adult rabbits were injured with 187.5 mg/kg meconium (7.5 ml/kg of meconium at 25 mg/ml). Static compliance measurements were made prior to injury and at 0.9 hours after injury. Treatment was at approximately 1.1 hours post injury with KL$_4$-Surfactant lavage (2–4 lavages with KL$_4$-Surfactant at a concentration of 2–5 mg/ml followed by a lavage with surfactant at a concentration of 10–15 mg/ml), a single bolus of 100 mg/kg KL$_4$-surfactant, or saline lavage.

Static compliance was measured again at 5.1 hours post injury (i.e., 4 hours after treatment was begun). Compliance values are the mean±SEM of measurements made at 30 cm H$_2$O pressure during the inflation portion of the measurement and are expressed as ml air/30 cm H$_2$O/kg. There was no statistical difference between the groups in the pre-injury or 0.9 hour post injury values. Only the KL$_4$-surfactant lavage group was significantly different from the untreated control group at 5.1 hours post injury.

TABLE 6

Compliance Values of Lungs of Rabbits Injured With Meconium Followed by Various Forms of Treatment

| Treatment: | None | KL$_4$-Surfactant Lavage | KL$_4$-Surfactant Bolus | Saline Lavage |
|---|---|---|---|---|
| n | 7 | 11 | 5 | 5 |
| pre-injury | 12.3 ± 1.0 | 11.9 ± 0.5 | 11.4 ± 0.5 | 10.8 ± 0.5 |
| post injury (0.9 hr.) | 1.9 ± 0.4 | 2.0 ± 0.5 | 2.6 ± 0.5 | 1.3 ± 0.2 |
| post injury (5.1 hrs) | 3.1 ± 0.8 | 6.2 ± 0.9 | 1.7 ± 0.1 | 2.3 ± 0.6 |

To test the effect of meconium in vivo on the rabbit surfactant, additional rabbits receiving 187.5 mg/kg human meconium, underwent bronchoalveolar lavage after 1 hour with saline to obtain the surfactant. The surfactant was isolated by high speed centrifugation as described above, and the activity of the residual native surfactant was determined using the pulsating bubble surfactometer at 3 mg/ml phospholipid. As shown in Table 7, the activity of surfactant was greatly diminished.

TABLE 7

Inhibition of Intrinsic Surfactant Activity Following Instillation of Meconium Into Adult Rabbit Lungs

| | Surface Tension | |
|---|---|---|
| | Minimal | Maximal |
| Lavage – meconium | 2.9 ± 0.9 | 33.5 ± 0.6 |
| Lavage + meconium | 22.4 ± 1.3 | 56.5 ± 2.5 |

Each value represents the mean±SEM of six determinations of surface tension obtained with surfactant at a concentration of 3 mg/ml isolated from lavage fluids recovered from two rabbits. Saline lavage was performed one hour after 187.5 mg/Kg of meconium was instilled into the lungs. Surface tensions are expressed in dynes/cm and were measured one minute after bubble formation in a pulsating bubble surfactometer.

As controls, three rabbits received equal volumes (5–7.5 ml/kg) of sterile saline intratracheally instead of meconium. The effect on PaO$_2$ levels is shown in FIG. 3. The average PaO$_2$ remained between 400 and 550 mm Hg over the 5 hour period, although one rabbit showed a gradual fall in PaO$_2$ to 249 mm Hg by 5.5 hours. Statistical difference in PaO$_2$ values (p<0.05) was seen between the saline control and meconium-treated rabbits for all time points≧1.0 hr. Compliance measurements of these rabbits fell from 14.2 to 8.0 at 0.9 hours and then recovered partially by 5.1 hours. At autopsy the lungs were diffusely expanded with 2–5 small (<0.5 cm) zones of atelectasis in the lower lobes, and with two larger zones of atelectasis, 1–2 cm in size, in the rabbit showing a gradual fall in PaO$_2$. Microscopically, >90% of the lung showed expanded alveoli, but atelectatic zones were observed containing collapsed alveoli and a mild infiltration of inflammatory cells.

ii. The effect of bronchoalveolar lavage with dilute KL$_4$-Surfactant on lung expansion, gas exchange and pulmonary inflammatory response in meconium-iniured adult rabbits Seventeen rabbits were given meconium at 187.5 mg/kg to induce (a) loss of surfactant activity in the lungs with associated collapse of the alveoli, and (b) development of inflammation at 3–5 hours after meconium instillation. Twelve of the rabbits were lavaged with KL$_4$-Surfactant as follows: 2–4 times with the KL$_4$-Surfactant diluted to 2–5 mg/ml and once at 10- 15 mg/kg using 20 ml/kg divided equally between right and left sides as described above. The remaining 5 rabbits were similarly lavaged with equal volumes of sterile saline, rather than with KL$_4$-Surfactant. The recovered volumes of the sequential lavages were measured and the individual lavage fluids saved for assays of meconium content. The FiO$_2$ was maintained at 1.0 and the ventilators adjusted to PIP of 25–28 and PEEP of 2–10, with a ventilatory rate of 20–32/min as required to maintain adequate ventilation.

The removal of meconium by 3 sequential lavages with dilute KL$_4$-Surfactant is shown in FIG. 5. As noted, about 29% of the instilled meconium was removed by the first lavage, 7.5% more in the second lavage, and less than 5% in the third lavage. As will be noted below, this correlated with diminished meconium observed microscopically in lung sections taken at necropsy than was observed in rabbits not lavaged. Following lavage with dilute KL$_4$-Surfactant, a single divided lavage using KL$_4$-Surfactant at 10–15 mg/ml was performed in order to assure that sufficient functional surfactant was present in the lungs. The calculated average amount of KL$_4$-Surfactant remaining in the lungs after this final lavage was 77±12 mg/kg.

The response in PaO$_2$ of the rabbits to the bronchoalveolar lavage with KL$_4$-Surfactant occurred rapidly, most often within 2 minutes after the first lavage (FIG. 6). The PaO$_2$ rose from <100 mm Hg to approximately 400 mm Hg with the rabbit ventilated at FiO$_2$ of 1.0. The PaO$_2$ remained elevated through 5 hours although a drop to a mean of about 300 mm Hg was seen 3–5 hours after instillation of the meconium.

Rabbits receiving lavage with saline instead of dilute KL$_4$-Surfactant failed to show improvement in gas exchange (FIG. 6) although comparable amounts of meconium were removed. Increases in PEEP did not increase appreciably the PaO$_2$ in saline-lavaged animals. The difference in PaO$_2$ values between rabbits treated with KL$_4$-Surfactant lavage and those lavaged with saline was statistically significant at all time points following treatment.

Static compliance assays, performed at time 0, 0.9 hours after instillation of meconium, (immediately before lavage treatment), and at approximately 5 hours after injury with meconium, (i.e., approximately 4 hours after lavage treatment), are shown in FIG. 4 and Table 6. As noted previously, the compliance values fell after instillation of meconium. Lavage treatment with KL$_4$-Surfactant (FIG. 4B) resulted in a significant improvement in compliance at the 5 hour time point as shown, while lavage with saline (FIG. 4C) failed to restore compliance changes above those of rabbits receiving meconium alone. Compliance analyses performed in 4 rabbits at an intermediate time point, (2.6 hours after surfactant lavage), revealed values increased to an average of 5.3 ml/kg at 30 cm $H_2O$ pressure, up from an average of 2.4 ml/kg 0.9 hours after meconium injury. At 5 hours, the average value for these 4 rabbits was 7.1 ml/kg.

Autopsies of $KL_4$-Surfactant-lavaged rabbits, performed between 5 and 6 hours after instillation of meconium, showed generalized expansion of the lungs, with patchy zones of partial atelectasis generally in the lower lobes (not shown). These atelectatic zones nevertheless contained regions of fine air expansion. Microscopically, the lungs exhibited clear, expanded alveoli, although the partially atelectatic areas revealed the presence of pink-stained alveolar fluid, containing moderate numbers of PMNs, but few red cells. The expanded alveoli contained less protein-rich fluid and strikingly fewer PMNs than the atelectatic alveoli (Table 8). Although not quantitated at the microscopic level, there appeared to be distinctly less meconium in the alveoli than in non-lavaged rabbits.

iii. The efficacy of treatment of meconium-iniured rabbit lungs with bolus instillation of $KL_4$-Surfactant (without lavage).

Five rabbits were given 187.5 mg meconium intratracheally as before, and after 1 hour, each received a 100 mg/kg bolus of $KL_4$-Surfactant at 30 mg/ml. The results are shown in FIG. 7.

There was a moderate rise in $PaO_2$ from 56 mm Hg to approximately 200 mm Hg between 1 and 2 hours after instillation of the $KL_4$-Surfactant. After this time period, however, the $PaO_2$ gradually subsided, falling below 100 mm Hg by 3 hours after treatment. Compliance values at 5.1 hours after meconium injury were nearly the same as those 0.9 hours after meconium injury, i.e., before treatment with $KL_4$-Surfactant bolus (Table 6). At autopsy, the lungs were almost completely collapsed, except for the small caps of uninvolved, expanded lung on the apices of the upper lobes that were apparently not exposed to meconium (not shown).

TABLE 8

The Effect of $KL_4$-Surfactant Treatment on the Development of Inflammation in Meconium-Injured Rabbits

| | Meconium left in lungs (mg/kg)[a] | PMNs/12 HPF[b] | Protein (mg/ml) | RBCs (cells/μl × $10^3$) | PMNs (cells/μl × $10^3$) | MPO (units/ml) | IL-8 (ng/ml) | Inflammatory Index (units/ml) |
|---|---|---|---|---|---|---|---|---|
| $KL_4$-surfactant lavage (n = 9) | 122.4 ± 4.41 | 132 ± 21 | 3.3 ± 0.6 | 7.9 ± 2.3 | 7.4 ± 1.9 | 1016 ± 315 | 12.4 ± 3.6 | 1.00 ± 0.31 |
| Saline lavage (n = 5) | 100.8 ± 9.7 | 595 ± 73 | 4.1 ± 0.4 | 22.0 ± 4.1 | 4.3 ± 1.2 | 1755 ± 132 | 4.9 ± 2.2 | 1.88 ± 0.18 |
| $KL_4$-surfactant bolus (n = 5) | 187.5 ± 0 | 216 ± 30 | 5.7 ± 0.3 | 23.6 ± 8.5 | 16.1 ± 2.0 | 1374 ± 145 | 24.3 ± 8.2 | 1.98 ± 0.24 |
| No treatment (n = 5) | 187.5 ± 0 | 431 ± 24 | 6.0 ± 0.9 | 58.3 ± 20.7 | 5.1 ± 1.3 | 1490 ± 537 | 37.9 ± 21.8 | 2.01 ± 0.58 |

Note: all values represent the mean ± SEM.
[a]Calculated by substracting the amount of meconium recovered in the lavages from the amount instilled into the animal.
[b]The number of polymorphonuclear cells detected histologically in 12 high power fields.

Seven rabbits receiving 2 lavages with $KL_4$-Surfactant (2 mg/ml) followed by a bolus of 100–150 mg (at a concentration of 30 mg/ml) showed responses in $PaO_2$ comparable to those of the previous $KL_4$-Surfactant lavage group. Compliance values and pathologic findings were also similar (data not shown).

The lungs of rabbits receiving lavage with saline, rather than $KL_4$-Surfactant, were totally atelectatic, except for small caps of expanded lung on the apical portions of the upper lobe (not shown). Microscopically, the alveoli were densely packed, and no air expansion was present. The alveolar spaces contained protein-rich fluid and an abundance of PMNs and red cells (Table 8). Small amounts of meconium, similar to those seen in surfactant-lavaged rabbits, were found.

As recorded in Table 8, analysis of bronchoalveolar lavage fluids, taken at the time of autopsy from rabbits lavaged with $KL_4$-Surfactant, revealed lower levels of protein, myeloperoxidase and red cells and a lower inflammatory index than fluids from rabbits not receiving lavage. These values in $KL_4$-Surfactant-lavaged rabbits were also lower, except for IL-8 levels, than those in saline-lavaged rabbits.

Seven additional meconium-injured rabbits received 2 lavages with $KL_4$-Surfactant at 2 mg/ml as above, but followed by bolus administration of $KL_4$-Surfactant of 100 or 150 mg/kg at 30 mg/ml concentration. The improvement in $PaO_2$, compliance and autopsy findings were similar to those in the $KL_4$-Surfactant-lavage group (data not shown).

Microscopically, approximately 80% of alveoli were filled with proteinaceous fluid and leukocytes (Table 8), and abundant meconium, but with scattered groups of alveoli showing expansion. Analysis of terminal bronchoalveolar lavage fluid revealed a marked inflammatory response (Table 8).

Therefore, measurements of the efficacy of treatment with $KL_4$-Surfactant by lavage as opposed to bolus instillation revealed that the method of lavage was superior both from the standpoint of improved gas exchange, and also the lessened inflammatory response. The data showed that while bolus instillation, without lavage, resulted in a modest increase in $PaO_2$ over the first two hours, the effect was ephemeral, with $PaO_2$ values returning to levels at or below 100 mm Hg within about 2 hours. This transient effect may be explained by the continued presence of meconium in the lungs which may have directly inactivated the instilled $KL_4$-Surfactant (and native surfactant) in the lung. Additionally, bolus treatment with $KL_4$-Surfactant failed to reduce the inflammatory response to meconium at 3–5 hours, allowing the inflammation to inactivate further the surfactant and also impede pulmonary function independently of its action on surfactant.

c. Primate Lavage Model and Instillation Protocol

In this model, newborn rhesus monkeys, after receiving human meconium intratracheally before their first breath, developed severe loss of pulmonary function. Treatment of these monkeys 1–5 hours after birth with BAL including lavage with dilute $KL_4$-Surfactant, produced clearing of chest radiographs and a rapid improvement in pulmonary function, with a/A ratios rising into the normal range, where they remained through the study period.

The primate studies were limited to 10 newborn rhesus monkeys. Rhesus monkeys were delivered by Caesarean section at the time of full-term gestation (157–160 days), performed by the veterinary staff of the Primate Center of the University of California, Davis. After delivery of the head and neck, vecuronium bromide was injected IM, and tracheotomy was performed with placement of a 2.0 mm internal diameter endotracheal tube with the distal tip being 0.5 to 1 cm above the carina prior to delivery of the body and clamping of the umbilical cord. The endotracheal tube was clamped to prevent gasping, and delivery was completed.

Each newborn rhesus was weighed and placed under a radiant warmer and meconium was instilled through the endotracheal tube, into the fluid-filled lungs prior to the first breath. Each animal was then placed on a mechanical ventilator set on IMV: $FiO_2$ of 0.8–1.0, PIP of 30–35 cm $H_2O$, PEEP of 4 cm $H_2O$, and 40 breaths/min with inspiratory time of 0.4 s.

A 3.5 French umbilical artery catheter was inserted into the aorta (to L4) to obtain arterial blood samples and for administration of fluids. The monkey received 5–8.3 ml/kg/hr of 5% dextrose in water with 0.5 U/ml heparin throughout the study.

Continuous measurements of heart rate, arterial blood pressure, arterial blood oxygen saturation and rectal temperature were maintained through the study. Arterial blood samples were obtained every 20–60 min for blood gas and pH analyses. Mechanical ventilation and $FiO_2$ were adjusted to maintain $PaO_2$ of 50–70 mm Hg, $PaCO_2$ of 40–50 mm Hg and pH>7.25. Chest radiographs were obtained within 1 hour of birth and meconium administration, within 1 hour of surfactant treatment and at various intervals thereafter as noted. Paralysis was maintained throughout the study with vecuronium bromide.

Lavage with dilute $KL_4$-Surfactant was performed through a 3.5 French umbilical catheter inserted through the endotracheal tube and cut so the tip was just distal to the tip of the tube. The monkeys received 100% $O_2$ throughout the procedure. Lavage was performed with $KL_4$-Surfactant diluted to 2 mg/ml, using 10–20 ml/kg, divided equally between right side and left side and administered as described for rabbits (above). Monkeys received 1–3 subsequent lavages using $KL_4$-Surfactant at 2 mg/ml and either a final lavage at 15 mg/ml or a bolus of 100 mg at 30 mg/ml. Cutaneous saturation of the blood was monitored throughout the procedure.

In 5 animals, a second instillation of meconium was given. Increasing doses of meconium were given: 2 monkeys receiving 187.5 mg/kg, 5 receiving 563 mg/kg, 2 receiving 750 mg/kg, and one receiving 843.8 mg/kg (mean=553.1 mg/kg). The a/A ratio in all meconium-treated monkeys within 1 hour after instillation of the full dose of meconium fell to approximately 0.20 or less. Chest radiographs showed diffuse opacity, characteristic of MAS. Noteworthy was a marked sensitivity of the monkeys to handling, with sharp decrements in oxygen saturation occurring that lasted 2–10 min. Seven of the monkeys were treated by lavage with dilute $KL_4$-Surfactant at times ranging from 1.6 to 5.4 hours after birth and instillation of meconium. The other three monkeys served as controls and were maintained for 20–24 hours with ventilatory support. The control animal treated with the lowest dose of meconium (187.5 mg/kg), given in two doses, recovered with a rise in a/A into the normal range (>0.4) noted about 2 hours after the second instillation of meconium. The dose of meconium used in this animal and in a lavage-treated animal receiving the same dose was, therefore, considered insufficient to elicit and maintain severe pulmonary deficiency over a 20-hour period; data from these two monkeys were not included in the results discussed below.

FIG. 8 shows the mean a/A ratio over time for the 6 monkeys receiving ≧563 mg/kg (mean=656 mg/kg) of meconium and treated with lavage with dilute $KL_4$-Surfactant. Of the two control animals treated with a comparable amount of meconium, a/A ratios were not obtainable for one due to an inability to establish an arterial line. The a/A ratio in the other control animal remained at approximately 0.1 over an 18 hour period (FIG. 8). In addition, three monkeys, receiving 563, 750 and 843.8 mg meconium/kg were monitored for 2.6, 3.2 and 5.4 hours, respectively, before treatment with surfactant lavage. a/A ratios remained at approximately 0.1 to 0.25 until initiation of surfactant-lavage treatment.

In the treatment group receiving lavage with dilute $KL_4$-Surfactant, an abrupt rise in a/A ratio was observed immediately following the lavage (FIG. 8). The $FiO_2$ was maintained at 1.0 during the period of lavages with $PaO_2$ values after treatment typically being >300 mm Hg. This resulted in aberrantly high a/A ratios and when the $FiO_2$ was lowered to the point that $PaO_2$ was in the range of 50–70 mm Hg, the a/A ratios decreased as shown one hour after surfactant lavage in FIG. 8. In a few monkeys the a/A ratio fell transiently to <0.2 even in the presence of clearing chest radiographs (see below). By approximately 4–8 hours after lavage-treatment with $KL_4$-Surfactant, the a/A ratios rose into the normal range. All treated animals were breathing room air by the termination of the study period (mean time to $FiO_2$=0.21 was 11.2 hours).

An appreciable clearing of the chest radiographs could be seen within 30 min after the start of surfactant lavage (not shown). Nearly complete clearing was observed within 18–20 hours. Generalized opacity of the chest radiographs remained in the two control animals over the 18 hour period with some evidence of peripheral clearing after approximately 10 hours.

At 18–24 hours of age, the animals were euthanized. Gross inspection of the meconium-injured lungs of monkeys that were lavaged with $KL_4$-Surfactant revealed generalized expansion, with scattered small zones of dark red atelectasis, mostly in the dorsal (dependent) regions of the lower lobes. Cut sections of these atelectatic zones showed that they involved 1–2 mm of the surface, with light-pink, expanded lung beneath. By contrast, lungs of the two monkeys receiving meconium, but without $KL_4$-Surfactant treatment, were >80% atelectatic. Microscopically, the lungs of monkeys treated with $KL_4$-Surfactant-lavage were expanded with clear alveoli and a small amount of meconium, edema and leukocytes. In the zones of atelectasis, meconium was present in large quantities along with PMNs and modest amounts of edema fluid. The lungs of monkeys not treated with surfactant were collapsed and filled with meconium, neutrophils and some edema. There was little to no expansion. The lobes of the lung not taken for microscopic analysis were lavaged twice with saline for analysis of the inflammatory reaction. The results of these analyses are shown in Table 9. The data show a diminution in the markers of inflammation in $KL_4$-Surfactant-lavaged animals.

TABLE 9

The Effect of KL$_4$-Surfactant Lavage on the
Development of Inflammation in Meconium-Injured Monkeys

|  | KL$_4$-Surfactant Lavage (n = 6) | No Treatment (n = 2) |
| --- | --- | --- |
| Protein (mg/ml) | 1.07 ± 0.2 | 4.4 |
| RBCs (cells/mm$^3$) | 2598 ± 1110 | 26800 |
| PMNs (cells/mm$^3$) | 1589 ± 445 | 2339 |
| MPO (units/ml) | 252 ± 54 | 1099 |
| IL-8 (ng/ml) | 1.35 ± 0.5 | 6.8 |
| Inflammatory Index (units/ml) | 0.17 ± 0.5 | 2.6 |

Note: values for the animals receiving KL$_4$-Surfactant are the mean ± SEM for the 6 treated animals; because n = 2 in the control group, SEM was not calculated.

d. The Effect of Lavage Treatment of Meconium-injured Lungs using KL$_4$-Surfactant The data in this study indicate that in models of meconium aspiration syndrome (MAS) in rabbit and newborn monkeys pulmonary function can be greatly improved within minutes by lavage of the lungs with dilute KL$_4$-Surfactant followed by instillation of a sustaining dose. PaO$_2$, a/A ratio, pulmonary compliance and chest radiographs all revealed rapid improvement.

Two species were employed: adult rabbits that exhibit a brisk and marked inflammatory response to instillation of human meconium; and newborn primates (*Macaca mulatta*) that were given human meconium intratracheally in the amniotic fluid of the lung at the time of Caesarean delivery and before the first breath.

The primate model mimics closely the situation in human infants who aspirate meconium in utero shortly before birth. Of particular interest, the improvement in pulmonary function in rhesus monkeys persisted and the clearing of chest radiographs continued over the course of the study, approximately 20 hours. The monkeys were breathing room air at approximately 11 hours after receiving KL$_4$-Surfactant lavage.

In both rabbits and rhesus monkeys, the instilled meconium induced a rapid fall in gas exchange (FIGS. 3, 8) and lung compliance (FIG. 4) associated with the development of atelectasis.

Three mechanisms have been proposed to explain the meconium-induced decrement in pulmonary function: 1) particles of meconium may obstruct small bronchioles in the lung; 2) meconium may inhibit surfactant directly; and 3) meconium-induced inflammation may serve to inhibit surfactant. The current studies support the theory that meconium-induced dysfunction of surfactant is a major factor in the loss of pulmonary function in MAS. The decrement in lung function in rabbits was associated with a loss of surfactant activity as evidenced by atelectasis associated with dysfunction of surfactant removed from the lung (Table 7). These data are consistent with previous in vitro data showing that mixing meconium, or organic and aqueous extracts of meconium with surfactant leads to surfactant dysfunction. The mechanism of the inactivation and the constituents of the meconium responsible remain unknown. By contrast, loss of pulmonary function owing to particulate meconium appears unlikely in the present study, given that the meconium was filtered, plugs were not observed microscopically in bronchi and lavage with saline alone failed to expand the alveoli and improve lung function.

The present data indicate that lavage with dilute KL$_4$-Surfactant removed sufficient amounts of meconium in both rabbits and monkeys to allow the KL$_4$-Surfactant, possibly coupled with residual native surfactant, to expand the alveoli, improve pulmonary function and compliance and diminish the development of inflammation. Newborn rhesus monkeys, after receiving human meconium intratracheally before their first breath, developed severe loss of pulmonary function. Treatment of these monkeys 1–5 hours after birth with BAL including lavage with dilute KL$_4$-Surfactant, produced clearing of chest radiographs and a rapid improvement in pulmonary function, with a/A ratios rising into the normal range, where they remained through the study period.

In contrast, lavage of the lungs with saline, rather than surfactant, failed to improve pulmonary function and, in fact, resulted in a greater inflammatory reaction in the lung. The detrimental effect of saline lavage or bolus instillation of saline has been reported.

e. The Effect of KL$_4$-Surfactant Lavage on the Development of Inflammation in Meconium-Injured Lungs The amount of pulmonary inflammation in meconium-injured adult rabbits was compared in four treatment groups: KL$_4$-Surfactant-lavaged rabbits, saline-lavaged rabbits, rabbits treated with KL$_4$-Surfactant by bolus instillation, and rabbits receiving meconium alone (Table 8). The data indicate that meconium-injured rabbits receiving lavage treatment with KL$_4$-Surfactant exhibited less pulmonary inflammation than untreated controls, saline-lavaged rabbits or bolus-surfactant-treated rabbits. This was observed both in the terminal lavage fluids and microscopic sections of the lungs. The diminution of inflammation was striking in microscopic sections of lung of KL$_4$-Surfactant-lavaged rabbits in which small zones of atelectasis contained abundant edema and PMNs and RBCs, while the neighboring expanded lung was nearly devoid of each. Comparison of the amount of inflammation in the surfactant-lavaged and saline-lavaged rabbits suggests that the KL$_4$-Surfactant lavage reduced the inflammatory reaction even though nearly equal amounts of residual meconium were present in lungs in the two groups.

The mechanism of the inhibitory effect on inflammation by surfactant is unclear. One possible explanation is that surfactants, including KL$_4$-Surfactant, have been found to inhibit the function of inflammatory cells, which may diminish their contribution to the inflammatory reaction. (See Hayakawa et al, *Am. Rev. Respir. Dis.*, 140:1390–1397, 1989; Geertsma et al, *J. Immunol.*, 150:2391–2400, 1993; Suziki et al, *Am. Rev. Respir. Dis.*, 145: A876 (Abstr.), 1992; Yoshida et al, *Life Sci.*, 49:1359–1365, 1991; Chao et al, *J. Clin. Invest.*, 96:2654–2660, 1995; and Ahuja et al, *Am. J. Respir. Cell. Mol. Biol.*, 14:496–503, 1996). Similarly, expansion of the alveoli and restoration of lung function by the KL$_4$-Surfactant lavage may diminish the formation of edema, thus reducing the amount of potential substrate for mediators of inflammation.

6. Premature Infant Rhesus Monkey Model for Evaluating Surfactant Activity

A preterm infant monkey model was also used to evaluate the efficacy of surfactants to treat lung function deficiencies.

Rhesus monkeys (*Macaca mulatta*) were delivered by cesarian section at 127–131 days gestation, and are known to be deficient in natural pulmonary surfactant. The monkeys were prepared as described in Example 5 for tracheotomy, connected to a ventilator and maintained with mechanical ventilation as described.

Respiratory distress was then diagnosed by observing clinical and radiographic criteria of a ratio of arterial to alveolar oxygen tension (a/A) of less than 0.22 and diffuse granular pulmonary radiopacity on chest radiographs. Thereafter, each monkey was dosed with a test composition intratracheally through the umbilical catheter in the endotracheal tube in which one half of the dose was administered with the animal in the right lateral decubitus position and half in the left lateral decubitus position and with the ventilation transiently paused for about 10–30 seconds for dose instillation.

$KL_4$-Surfactant prepared as described in Example 4 was instilled at about 5.0 to 5.7 ml per kg. A non-peptide containing surfactant, Exosurf Neonatal (Burroghs Wellcome Co., Research Triangle Park, N.C.) was reconstituted with water to contain per ml: 13.5 mg DPPC, 1.5 mg cetyl alcohol and 1.0 mg tyloxapol in 0.1 N NaCl, and instilled at the dosage of 5.0 ml per kg. Thirty monkeys received $KL_4$-Surfactant at a dosage of 100 mg per kg (24 monkeys) or 99 mg per kg (6 monkeys) at a mean age of 1.45 hour, and nine monkeys received Exosurf at a mean age of 2.2 hour, and a/A lung function measurements were calculated at various times as listed in FIG. 2. Lungs of monkeys receiving $KL_4$-Surfactant (solid bars) functioned dramatically better than lungs of monkeys treated with Exosurf (hatched bars).

7. Use of Pulmonary Surfactant as a Lavage Agent to Remove Inflammatory Mediators and Restore Pulmonary Function in a Rabbit Inflammation Model Direct instillation of lipopolysaccharide (LPS) into the adult rabbit lungs was used as a model for respiratory distress accompanied by inflammatory mediators. This model was evaluated using the dilute surfactant lavage method.

Thirteen adult rabbits were partially depleted of intrinsic lung surfactant and given intratracheal instillation of a bolus of bacterial LPS at 0.75 micrograms (ug) per kg in a total volume of 3 mls per kg. The rabbits were then maintained on the ventilator apparatus as described in Example 5 for about 3 hours to allow an inflammatory response to develop.

After 3–4 hours, six rabbits received three lavage washes of 20 ml per kg were given over a 30 minute time period, with ten minutes per cycle, using $KL_4$-Surfactant prepared as described in Example 5 at 5 mg/ml. 100% $O_2$ was administered through the ventilator throughout the procedure. Seven remained untreated as controls.

FIG. 9 illustrates the pulmonary function in rabbits using pulmonary lavage following LPS injury. The $PaO_2$ levels fall as the lungs are injured by the LPS within minutes after LPS is instilled. Lavage with the pulmonary surfactant composition dramatically improved lung function and $PaO_2$ levels, whereas untreated controls did not show improvement of lung function.

To determine the effect on inflammatory components in the present LPS-injury model, the lavage wash was collected from the rabbits in each of the above three wash cycles and the collected wash was evaluated for the presence of components for the inflammatory process by measuring total protein, myeloperoxidase, polymorphonuclear cells (PMN's) and erythrocytes, as described in Example 5. As shown in FIG. 10, the levels of all four components progressively decreased with each successive lavage indicating that the lavage method was effective at removing components of inflammation.

To evaluate the long term effect of the dilute surfactant lavage therapy on pulmonary inflammation, the same rabbits were also analyzed for the content of inflammatory components about four hours after the treatment. To that end, rabbits were monitored for about 3.5 hours after the beginning of the surfactant lavage and it was observed that the $PaO_2$ levels did not improve with the control rabbits, but the levels did improve for the surfactant lavaged animals. Thereafter, the animals were sacrificed, the lungs were recovered and the lower lung lobe was washed ex vivo by adding 10 mls of normal saline to one lobe and aspirating the wash to collect alveolar contents. The aspirated wash was assayed as described for FIG. 10, and the results are shown in FIG. 11. The reduction in inflammatory components was long-term, i.e., the wash was effective at reducing the ongoing inflammatory response because there was little return of the inflammatory reaction 3.5 hours after treatment with $KL_4$-Surfactant.

These results indicate that various inflammatory components and mediators are removed using a dilute surfactant lavage according to the present invention, and that the treatment reduces ongoing inflammation. Thus, the invention can be used in any condition of respiratory distress involving inflammatory mediators present in the form of protein, enzymes, cells and the like mediators.

8. Porcine Lavage Model and Instillation Protocol

Piglets were also evaluated as a model for repair of pulmonary function following meconium aspiration.

Four-day old piglets were obtained, and attached to mechanical ventilators as described in Example 7. Human meconium prepared as described in Example 5 was administered in three bolus installations over 1 hour, each bolus containing 30% (w/v) meconium and administered in a dose of 3 ml per kg. $FiO_2$ was maintained at 1.0 and continuously applied throughout the procedure. PEEP was maintained at 6 cm water in one group of piglets throughout (FIG. 12B) and in a second group of piglets, the PEEP was maintained at 6 cm water during meconium instillation, but was increased to 8 cm water 30 minutes before the first dilute surfactant lavage, and maintained at 8 cm water for about 2 hours after the last lavage (FIG. 12A). $PaO_2$ was monitored throughout the procedure, and the results are shown as $PaO_2$ over time (FIG. 12). Dilute surfactant lavage used was $KL_4$-Surfactant prepared as described in Example 7, and administered at 8 ml per kg per instillation in a series of installations at dosages as follows: first instillation (arrows, 1A and 1B) at 2.5 mg/ml; second instillation for FIG. 12B (arrows, 2A and 2B) at 2.5 mg/ml; second instillation for FIG. 12A (arrows, 2A and 2B) at 10 mg/ml; and third instillation for FIG. 12B (arrows, 3A and 3B) 10 mg/ml, where the timing of the installations is indicated by the position of the arrows in the Figures, and A indicates instillation into either the piglet's right or left lung, and B indicates instillation into the piglet's other lung. Removal of pulmonary fluid after each lavage was accomplished by two or more suctions using timed short (10 second) bursts of negative pressure (80 mm Hg) suction separated by one to five minute periods without suction to allow for equilibration of the $PaO_2$.

The use of elevated PEEP at 8 cm water produced a striking increase in the rate of recovery of arterial oxygen following dilute surfactant lavage in the meconium-injured lung model. Whereas, the use of 6 cm water PEEP in combination with the lavage washes produced a slow but gradual increase in $PaO_2$, the use of 8 cm water PEEP produced a rapid and greater increase in $PaO_2$, indicating a quicker recovery from meconium-induced respiratory distress.

These same piglets were also monitored for peripheral blood oxygen saturation using a pulsating oxymeter. As seen in FIG. 13, the piglet receiving lavages with 8 cm PEEP maintained healthy levels of peripheral oxygen, whereas the piglet receiving lavages with 6 cm PEEP experienced dramatic drops in the levels of peripheral oxygen.

To further characterize the preferred dilute lavage procedure in cases of respiratory distress, the duration of suction for removal of the pulmonary fluids following lavage installations was evaluated. In the same piglet model, piglets were fitted with a ventilator apparatus as described and were similarly treated with meconium. $FiO_2$ was maintained at 1.0 and PEEP was maintained at 8 cm water throughout the procedure. Peripheral blood oxygen saturation was monitored using a pulsating oxymeter throughout the procedure and expressed as $SaO_2$. A lavage instillation of $KL_4$-Surfactant was given at 2.5 mg/ml, and a suction at 80 mm Hg negative pressure was performed to remove pulmonary fluids shortly after terminating the lavage installations. Either 10 seconds (FIG. 14A) or about 60 seconds (FIG. 14B) of suction was applied to remove the pulmonary fluid.

The effect of suction duration on oxygen saturation in arterial blood was dramatic, indicating that extended suctioning lowers blood oxygen levels. Thus, in preferred embodiments, the suction duration should be less than 30 seconds, preferably not exceed 20 seconds, and more preferably be less than 10 seconds. If multiple sequential suctions are to be applied, they should be separated by brief recovery periods of sufficient time (20 to 20 minutes) to optimize blood oxygen levels.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method for pulmonary lavage of a mammal comprising:
   a) applying gas positive end-expiratory pressure (PEEP) with a ventilator into a lung section of said mammal at a pressure of from about 4 to 16 cm water;
   b) instilling a lavage composition containing dilute surfactant in a pharmaceutically acceptable aqueous medium into said lung; and
   c) removing pulmonary fluid from said lung using short intervals of tracheo-bronchial suction at a negative pressure of about 20 to 100 mm mercury.

2. The method of claim 1 wherein said ventilator PEEP is applied for a preselected time period prior to instilling step (b).

3. The method of claim 2 wherein said time period is up to about 30 minutes.

4. The method of claim 1 wherein said ventilator PEEP is applied continuously during steps (b) and (c).

5. The method of claim 1 wherein said ventilator PEEP is applied for a preselected time period after removing step (c).

6. The method of claim 5 wherein said time period is up to about 24 hours.

7. The method of claim 6 wherein said time period is from about 0.5 to 6 hours.

8. The method of claim 1 wherein said ventilator PEEP is administered for up to about 30 minutes prior to instillation step (b), continuously throughout steps (b) and (c), and for up to about 24 hours after the completion of step (c).

9. The method of claim 1 wherein said mammal is a newborn infant and wherein said ventilator PEEP levels are 4–15 cm water.

10. The method of claim 9 wherein said ventilator PEEP levels are 6–9 cm water.

11. The method of claim 9 wherein said ventilator PEEP levels are 8 cm water.

12. The method of claim 1 wherein said mammal is an adult, a juvenile or infant.

13. The method of claim 12 wherein said ventilator PEEP levels are 6–12 cm water.

14. The method of claim 12 wherein said ventilator PEEP levels are 8–10 cm water.

15. The method of claim 1 wherein said gas contains 21 to 100% oxygen.

16. The method of claim 15 wherein said gas contains 50 to 100% oxygen.

17. The method of claim 1 wherein said dilute surfactant is present in said composition at 0.1–50 mg per ml.

18. The method of claim 17 wherein said dilute surfactant is present in said composition at 0.5–20 mg per ml.

19. The method of claim 17 wherein said dilute surfactant is present in said composition at 2–10 mg per ml.

20. The method of claim 1 wherein said lavage composition is instilled in a volume of 4–60 ml per kilogram.

21. The method of claim 20 wherein said lavage composition is instilled in a volume of 8–30 ml per kilogram per lung section.

22. The method of claim 1 wherein said removing step interval is about 2 to 120 seconds.

23. The method of claim 22 wherein said removing step interval is about 5 to 20 seconds.

24. The method of claim 1 wherein said instilling and removing steps are repeated in sequence 1 to 5 times.

25. The method of claim 1 wherein said composition is instilled in a first and second series, wherein said first series comprises from 1 to 3 cycles of steps (b) and (c) using dilute surfactant in said composition at 0.1 to 10 mg per ml, and wherein said second series comprises from 1 to 5 cycles of steps (b) and (c) using dilute surfactant in said composition at 10 to 50 mg per ml.

26. The method of claim 1 further comprising after step (c):
   (d) instilling a composition containing surfactant in a pharmaceutically acceptable aqueous medium into said lung, wherein said surfactant is present in said composition at 15 to 100 milligrams per ml of composition and wherein from 10 to 300 mg of surfactant is instilled per kilogram.

27. The method of claim 1 wherein said lavage is conducted to treat respiratory distress syndrome (RDS) in said mammal.

28. The method of claim 27 wherein said RDS is caused by meconium aspiration.

29. The method of claim 27 wherein said RDS is associated with pulmonary inflammation.

30. The method of claim 27 wherein said RDS is associated with pulmonary infection.

31. The method of claim 27 wherein said RDS is associated with acute hypoxemia.

32. The method of claim 27 wherein said RDS is associated with persistant fetal circulation.

33. The method of claim 27 wherein said RDS is associated with congenital diaphramatic hernia.

34. The method of claim 27 wherein said RDS is associated with sepsis, pulmonary trauma, cranial or body trauma, pancreatitis, aspiration of gastric contents, heated vapor inhalation, noxious vapor inhalation, pneumonia or multiple transfusions.

35. The method of claim 1 wherein said mammal is a human.

36. The method of claim 1 wherein said lavage composition contains a natural pulmonary surfactant isolated from a mammal, or fragment thereof.

37. The method of claim 36 wherein said mammal is selected from the group consisting of bovine, porcine and human.

38. The method of claim 36 wherein said natural pulmonary surfactant is selected from the group consisting of surfactant proteins SP-B and SP-C.

39. The method of claim 36 wherein said natural pulmonary surfactant is substantially isolated human pulmonary surfactant (SP) protein.

40. The method of claim 1 wherein said lavage composition comprises one or more phospholipids and is polypeptide-free.

41. The method of claim 1 wherein said surfactant is a synthetic pulmonary surfactant.

42. The method of claim 41 wherein said synthetic pulmonary surfactant comprises one or more phospholipids and a polypeptide, said polypeptide, when admixed with said phospholipid, forms a synthetic pulmonary surfactant having a surfactant activity greater than the surfactant activity of the phospholipid alone.

43. The method of claim 41 wherein said synthetic pulmonary surfactant comprises one or more pharmaceutically acceptable phospholipids admixed with a polypeptide comprising at least 10 amino acid residues and no more than about 60 amino acid residues, said polypeptide including a sequence having alternating hydrophobic and hydrophilic amino acid residue regions represented by the formula $(Z_a U_b)_c Z_d$, wherein:

Z is a hydrophilic amino acid residue independently selected from the group consisting of R, D, E and K;

U is a hydrophobic amino acid residue independently selected from the group consisting of V, I, L, C and F;

a has an average value of about 1 to about 5;

b has an average value of about 3 to about 20;

c is 1 to 10; and d is 0 to 3.

44. The method of claim 43, wherein said polypeptide has an amino acid residue sequence represented by the formula:

KLLLLKLLLLKLLLLKLLLLK.

45. The method of claim 43 wherein said polypeptide has an amino acid residue sequence selected from the group consisting of:

KLLLLKLLLLKLLLLKLLLLK,

KLLLLLLLLKLLLLLLLLKLL, and

KKLLLLLLLKKLLLLLLLKKL.

46. The method of claim 41 wherein said synthetic pulmonary surfactant comprises one or more pharmaceutically acceptable phospholipids admixed with a polypeptide having an amino acid residue sequence selected from the group consisting of:

DLLLLDLLLLDLLLLDLLLLD,

RLLLLRLLLLRLLLLRLLLLR,

RLLLLLLLLRLLLLLLLLRLL,

RRLLLLLLLRRLLLLLLLRRL,

RLLLLCLLLRLLLLCLLLR,

RLLLLCLLLRLLLLCLLLRLL, and

RLLLLCLLLRLLLLCLLLRLLLLCLLLR.

47. The method of claim 41 wherein said synthetic pulmonary surfactant comprises:

a) a polypeptide comprising at least 10 amino acid residues and no more than about 60 amino acid residues and constituted by alternating groupings of charged amino acid residues and uncharged amino acid residues, and b) one or more pharmaceutically acceptable phospholipids, wherein said polypeptide is present in an amount sufficient to increase the surfactant activity of the composition above that of said phospholipid.

48. The method of claim 42, wherein said phospholipid is present in a polypeptide: phospholipid weight ratio in the range of about 1:7 to about 1:1,000.

49. The method of claim 42, wherein said phospholipid is selected from the group consisting of:

1,2-dipalmitoyl-sn-glycero-3-phosphocholine (dipalmitoylphosphatidylcholine, DPPC);

phosphatidyl glycerol (PG); and an admixture of DPPC and PG in a weight ratio of about 3:1.

50. The method of claim 42, further comprising palmitic acid.

51. The method of claim 42 wherein said polypeptide comprises at least 10 amino acid residues and no more than about 60 amino acid residues and constituted by alternating groupings of charged amino acid residues and uncharged amino acid residues.

52. The method of claim 51 wherein said alternating groupings of amino acid residues represented by the formula $(Z_a J_b)_c Z_d$, wherein:

Z is an amino acid residue independently selected from the group consisting of R, D, E, and K;

J is an α-aminoaliphatic carboxylic acid;

a has an average value of about 1 to about 5;

b has an average value of about 3 to about 20;

c is 1 to 10; and d is 0 to 3.

53. The method of claim 51 wherein said alternating groupings of amino acids residue regions represented by the formula $(B_a U_b)_c B_d$, wherein:

B is an amino acid residue independently selected from the group consisting of H, 5-hydroxylysine, 4-hydroxyproline, and 3-hydroxyproline;

U is an amino acid residue independently selected from the group consisting of V, I, L, C, Y, and F;

a has an average value of about 1 to about 5;

b has an average value of about 3 to about 20;

c is 1 to 10; and d is 0 to 3.

54. The method of claim 51 wherein said alternating groupings of amino acid residues represented by the formula $(B_a J_b)_c B_d$, wherein:

B is an amino acid residue independently selected from the group consisting of H, 5-hydroxylysine, 4-hydroxyproline, and 3-hydroxyproline;

J is an α-aminoaliphatic carboxylic acid;

a has an average value of about 1 to about 5;

b has an average value of about 3 to about 20;

c is 1 to 10; and d is 0 to 3.

55. The method of claim 54 wherein said J is an α-aminoaliphatic carboxylic acid having four to six carbons, inclusive.

56. The method of claim 54 wherein said J is selected from the group consisting of α-aminobutanoic acid, α-aminopentanoic acid, α-amino-2-methylpropanoic acid, and α-aminohexanoic acid.

57. The method of claim 42 wherein said polypeptide comprises at least 10 amino acid residues and no more than about 60 amino acid residues and constituted by alternating groupings of charged amino acid residues and uncharged amino acid residues as represented by the formula $\{(\text{Charged})_a(\text{Uncharged})_b\}_c(\text{Charged})_d$, wherein:

a has an average value of about 1 to about 5;

b has an average value of about 3 to about 20;

c is 1 to 10; and d is 0 to 3.

* * * * *

UNITED STATES PATENT AND TRADEMARK OFFICE
CERTIFICATE OF CORRECTION

PATENT NO. : 6,013,619
DATED : January 11, 2000
INVENTOR(S) : Cochrane et al.

Page 1 of 1

It is certified that error appears in the above-identified patent and that said Letters Patent is hereby corrected as shown below:

<u>Column 1,</u>
Line 4, insert:

-- This invention was made with government support under Grant Nos. HL 23584 and GM 37696 from the National Institutes of Health and Grant No. N00014 from the Office of Naval Research. The U.S. government may have certain rights in the invention. --

Signed and Sealed this

Thirteenth Day of April, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,013,619 |
| DATED | : January 11, 2000 |
| INVENTOR(S) | : Charles G. Cochrane and Susan D. Revak |

It is certified that error appears in the above-identified patent and that said Letters Patent is hereby corrected as shown below:

<u>Title page,</u>
Item [63], Related U.S. Application Data, should be deleted as follows:
"CROSS REFERENCE TO RELATED APPLICATIONS This is a continuation-in-part of application Ser. No. 08/488,123, filed Jun. 7, 1995, which is a continuation-in-part of application Ser. No. 08/419,824, filed Apr. 11, 1995, (now U.S. Pat. No. 5,789,381 which is a continuation of application Ser. No. 08/060,833, filed May 12, 1993 (now U.S. Pat. No. 5,407,914), which is a continuation-in-part of application Ser. No. 07/715,397, filed Jun. 14, 1991 (now U.S. Pat. No. 5,260,273), which is a continuation-in-part of application Ser. No. 07/293,201, filed Jan. 4, 1989 (now U.S. Pat. No. 5,164,369), which is a continuation-in-part of application Ser. No. 07/141,200, filed Jan. 6, 1988 (now abandoned). The disclosures of the foregoing applications are hereby incorporated by reference herein."

<u>Column 1,</u>
Lines 5-20, the section "CROSS REFERENCE TO RELATED APPLICATIONS" should be deleted as follows:
"CROSS REFERENCE TO RELATED APPLICATIONS This is a continuation-in-part of application Ser. No. 08/488,123, filed Jun. 7, 1995, which is a continuation-in-part of application Ser. No. 08/419,824, filed Apr. 11, 1995, (now U.S. Pat. No. 5,789,381 which is a continuation of application Ser. No. 08/060,833, filed May 12, 1993 (now U.S. Pat. No. 5,407,914), which is a continuation-in-part of application Ser. No. 07/715,397, filed Jun. 14, 1991 (now U.S. Pat. No. 5,260,273), which is a continuation-in-part of application Ser. No. 07/293,201, filed Jan. 4, 1989 (now U.S. Pat. No. 5,164,369), which is a continuation-in-part of application

UNITED STATES PATENT AND TRADEMARK OFFICE
CERTIFICATE OF CORRECTION

PATENT NO. : 6,013,619
DATED : January 11, 2000
INVENTOR(S) : Charles G. Cochrane and Susan D. Revak It is certified that error appears in the above-identified patent and that said Letters Patent is hereby corrected as shown below:

<u>Title page (cont'd)</u>,
Ser. No. 07/141,200, filed Jan. 6, 1988 (now abandoned). The disclosures of the foregoing applications are hereby incorporated by reference herein."

Signed and Sealed this

Thirtieth Day of August, 2005

JON W. DUDAS
*Director of the United States Patent and Trademark Office*

```
                          SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:1:

Lys Leu Leu Leu Leu Lys Leu Leu Leu Leu Lys Leu Leu Leu Leu Lys
1               5                  10                  15

Leu Leu Leu Leu Lys
            20

(2) INFORMATION FOR SEQ ID NO:2:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:2:

Lys Leu Leu Leu Leu Leu Leu Leu Leu Lys Leu Leu Leu Leu Leu Leu
1               5                  10                  15

Leu Leu Lys Leu Leu
            20

(2) INFORMATION FOR SEQ ID NO:3:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:3:

Lys Lys Leu Leu Leu Leu Leu Leu Leu Lys Lys Leu Leu Leu Leu Leu
1               5                  10                  15

Leu Leu Lys Lys Leu
            20
```

(2) INFORMATION FOR SEQ ID NO:4:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:4:

Asp Leu Leu Leu Leu Asp Leu Leu Leu Leu Asp Leu Leu Leu Leu Asp
1               5                   10                  15

Leu Leu Leu Leu Asp
            20

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:5:

Arg Leu Leu Leu Leu Arg Leu Leu Leu Leu Arg Leu Leu Leu Leu Arg
1               5                   10                  15

Leu Leu Leu Leu Arg
            20

(2) INFORMATION FOR SEQ ID NO:6:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:6:

Arg Leu Leu Leu Leu Leu Leu Leu Leu Arg Leu Leu Leu Leu Leu Leu
1               5                   10                  15

Leu Leu Arg Leu Leu
            20

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:7:

Arg Arg Leu Leu Leu Leu Leu Leu Leu Arg Arg Leu Leu Leu Leu Leu
1               5                   10                  15

Leu Leu Arg Arg Leu
            20

(2) INFORMATION FOR SEQ ID NO:8:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:8:

Arg Leu Leu Leu Leu Cys Leu Leu Arg Leu Leu Leu Leu Cys Leu
1               5                   10                  15

Leu Leu Arg (2) INFORMATION FOR SEQ ID NO:9:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (xi) SEQUENCE DESCRIPTION: SEQ ID NO:9:

Arg Leu Leu Leu Leu Cys Leu Leu Arg Leu Leu Leu Leu Cys Leu
1               5                   10                  15

Leu Leu Arg Leu Leu
            20

(2) INFORMATION FOR SEQ ID NO:10:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (xi) SEQUENCE DESCRIPTION: SEQ ID NO:10:

Arg Leu Leu Leu Leu Cys Leu Leu Arg Leu Leu Leu Leu Cys Leu
1               5                   10                  15

Leu Leu Arg Leu Leu Leu Leu Cys Leu Leu Leu Arg
            20                  25

(2) INFORMATION FOR SEQ ID NO:11:

(i) SEQUENCE CHARACTERISTICS:
            (A) LENGTH: 750 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: sig_peptide
            (B) LOCATION: 1..186

(ix) FEATURE:
            (A) NAME/KEY: CDS
            (B) LOCATION: 187..729

(xi) SEQUENCE DESCRIPTION: SEQ ID NO:11:

CACCTGGGCC TGTGCAAATC CCGGCAGCCA GAGCCAGAGC AGGAGCCAGG GATGTCAGAC      60

CCCCTGCCCA AACCTCTGCG GGACCCTCTG CCAGACCCTC TGCTGGACAA GCTCGTCGTC     120

CCTGTGCTGC CCGGGGCCCT CCAGGCGAGG CCTGGGCCTC ACACACAGGA TCTCTCCGAG     180

CAGCAA TTC CCC ATT CCT CTC CCC TAT TGC TGG CTC TGC AGG GCT CTG        228
       Phe Pro Ile Pro Leu Pro Tyr Cys Trp Leu Cys Arg Ala Leu
       1               5                   10

ATC AAG CGG ATC CAA GCC ATG ATT CCC AAG GGT GCG CTA GCT GTG GCA       276
Ile Lys Arg Ile Gln Ala Met Ile Pro Lys Gly Ala Leu Ala Val Ala
15              20                  25                  30

```
GTG GCC CAG GTG TGC CGC GTG GTA CCT CTG GTG GCG GGC GGC ATC TGC          324
Val Ala Gln Val Cys Arg Val Val Pro Leu Val Ala Gly Gly Ile Cys
                 35                  40                  45

CAG TGC CTG GCT GAG CGC TAC TCC GTC ATC CTG CTC GAC ACG CTG CTG          372
Gln Cys Leu Ala Glu Arg Tyr Ser Val Ile Leu Leu Asp Thr Leu Leu
                 50                  55                  60

GGC CGC ATG CTG CCC CAG CTG GTC TGC CGC CTC GTC CTC CGG TGC TCC          420
Gly Arg Met Leu Pro Gln Leu Val Cys Arg Leu Val Leu Arg Cys Ser
                 65                  70                  75

ATG GAT GAC AGC GCT GGC CCA AGG TCG CCG ACA GGA GAA TGG CTG CCG          468
Met Asp Asp Ser Ala Gly Pro Arg Ser Pro Thr Gly Glu Trp Leu Pro
     80                  85                  90

CGA GAC TCT GAG TGC CAC CTC TGC ATG TCC GTG ACC ACC CAG GCC GGG          516
Arg Asp Ser Glu Cys His Leu Cys Met Ser Val Thr Thr Gln Ala Gly
 95                 100                 105                 110

AAC AGC AGC GAG CAG GCC ATA CCA CAG GCA ATG CTC CAG GCC TGT GTT          564
Asn Ser Ser Glu Gln Ala Ile Pro Gln Ala Met Leu Gln Ala Cys Val
                115                 120                 125

GGC TCC TGG CTG GAC AGG GAA AAG TGC AAG CAA TTT GTG GAG CAG CAC          612
Gly Ser Trp Leu Asp Arg Glu Lys Cys Lys Gln Phe Val Glu Gln His
                130                 135                 140

ACG CCC CAG CTG CTG ACC CTG GTG CCC AGG GGC TGG GAT GCC CAC ACC          660
Thr Pro Gln Leu Leu Thr Leu Val Pro Arg Gly Trp Asp Ala His Thr
                145                 150                 155

ACC TGC CAG GCC CTC GGA GTG TGT GGG ACC ATG TCC AGC CCT CTC CAG          708
Thr Cys Gln Ala Leu Gly Val Cys Gly Thr Met Ser Ser Pro Leu Gln
    160                 165                 170

TGT ATC CAC AGC CCC GAC CTT TGATGAGAAC TCAGCTGTCC A                      750
Cys Ile His Ser Pro Asp Leu
175                 180

(2) INFORMATION FOR SEQ ID NO:12:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:12:

Phe Pro Ile Pro Leu Pro Tyr Cys Trp Leu Cys Arg Ala Leu Ile Lys
 1               5                  10                  15

Arg Ile Gln Ala Met Ile Pro Lys Gly Ala Leu Ala Val Ala Val Ala
                 20                  25                  30

Gln Val Cys Arg Val Val Pro Leu Val Ala Gly Gly Ile Cys Gln Cys
                 35                  40                  45

Leu Ala Glu Arg Tyr Ser Val Ile Leu Leu Asp Thr Leu Leu Gly Arg
                 50                  55                  60

Met Leu Pro Gln Leu Val Cys Arg Leu Val Leu Arg Cys Ser Met Asp
 65                  70                  75                  80

Asp Ser Ala Gly Pro Arg Ser Pro Thr Gly Glu Trp Leu Pro Arg Asp
                 85                  90                  95

Ser Glu Cys His Leu Cys Met Ser Val Thr Thr Gln Ala Gly Asn Ser
                100                 105                 110

Ser Glu Gln Ala Ile Pro Gln Ala Met Leu Gln Ala Cys Val Gly Ser
                115                 120                 125

Trp Leu Asp Arg Glu Lys Cys Lys Gln Phe Val Glu Gln His Thr Pro
                130                 135                 140
```

```
-continued

Gln Leu Leu Thr Leu Val Pro Arg Gly Trp Asp Ala His Thr Thr Cys
145                 150                 155                 160

Gln Ala Leu Gly Val Cys Gly Thr Met Ser Ser Pro Leu Gln Cys Ile
                165                 170                 175

His Ser Pro Asp Leu
            180

(2) INFORMATION FOR SEQ ID NO:13:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:13:

His Leu Leu Leu Leu His Leu Leu Leu Leu His Leu Leu Leu Leu His
1               5                   10                  15

Leu Leu Leu Leu His
            20
```